(12) United States Patent
He et al.

(10) Patent No.: US 9,051,332 B1
(45) Date of Patent: Jun. 9, 2015

(54) PHOTOCHROMIC INDENO-FUSED RING PYRAN COMPOUNDS

(71) Applicant: Transitions Optical, Inc., Pinellas Park, FL (US)

(72) Inventors: Meng He, Murrysville, PA (US); Massimiliano Tomasulo, Monroeville, PA (US); Anil Kumar, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 14/084,891

(22) Filed: Nov. 20, 2013

(51) Int. Cl.
*C07D 491/052* (2006.01)
*C07D 493/04* (2006.01)

(52) U.S. Cl.
CPC .......... *C07D 493/04* (2013.01); *C07D 491/052* (2013.01)

(58) Field of Classification Search
CPC ..................... C07D 491/052; C07D 493/04
USPC ..................... 549/234, 297, 381; 548/416
See application file for complete search history.

(56) References Cited

U.S. PATENT DOCUMENTS

| | | |
|---|---|---|
| 2007/0155964 A1 | 7/2007 | Walters et al. |
| 2012/0157677 A1 | 6/2012 | He et al. |
| 2012/0157696 A1 | 6/2012 | Chopra et al. |

*Primary Examiner* — Shawquia Jackson
(74) *Attorney, Agent, or Firm* — The Webb Law Firm

(57) ABSTRACT

The present invention relates to photochromic indeno-fused ring pyran compounds represented by the following Formula (I-A):

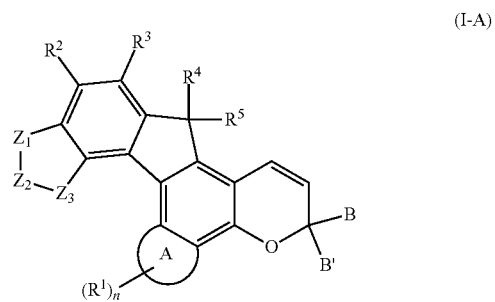

(I-A)

The present invention also relates to photochromic dichroic compounds, such as represented by Formula (I-A), in which (i) $Z_2$ is a group $N-R_{13}$ in which $R_{13}$ is a group L, and (ii) optionally at least one $R^1$ independently for each n is selected from a group L, in which the group L independently in each case is a lengthening group that provides the photochromic compound with dichroic properties, in accordance with some embodiments. The present invention also relates to photochromic articles, such as photochromic ophthalmic articles, that include one or more photochromic compounds according to the present invention, such as represented by Formula (I-A).

15 Claims, 6 Drawing Sheets

Scheme-(1)

Scheme-(2)

Scheme-(3)

Scheme-(4)

Scheme-(5)

Scheme-(6)

PHOTOCHROMIC INDENO-FUSED RING PYRAN COMPOUNDS

FIELD

The present invention relates to photochromic indeno-fused ring pyran compounds, which include a further fused ring attached to the indeno portion thereof, and to photochromic articles that include one or more such indeno-fused ring pyran photochromic compounds.

BACKGROUND

Indeno-fused ring pyran compounds, such as indeno-fused naphthopyrans are useful as photochromic compounds. Photochromic compounds and materials, such as indeno-fused naphthopyrans, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, or substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (such as in form of a photochromic coating composition) typically display colorless (or clear) and colored states that correspond to the colorless and colored states of the photochromic materials contained therein and/or applied thereto.

The properties, such as photochromic properties, of indeno-fused ring pyran compounds, such as indeno-fused naphthopyrans, can be modified by covalently bonding various groups, such as electron withdrawing and electron donating groups, at one or more ring positions on the fused-ring structure. Examples of properties of photochromic indeno-fused ring pyran compounds that can be modified by various groups being covalently bonded to one or more ring positions thereof include, but are not limited to, fade rate, change in optical density, and dichroic properties. With present indeno-fused ring pyran compounds, such as indeno-fused naphthopyrans, there are a limited number of ring positions to which various property-modifying groups can be covalently bonded.

It would be desirable to develop new photochromic indeno-fused ring pyran compounds that have additional and/or new ring-positions to which various property-modifying groups can be covalently bonded. It would be further desirable that such newly developed photochromic indeno-fused ring pyran compounds have photochromic properties that are at least the same as those of presently available photochromic indeno-fused ring pyran compounds.

SUMMARY

In accordance with the present invention, there is provided a photochromic compound represented by the following Formula (I-A),

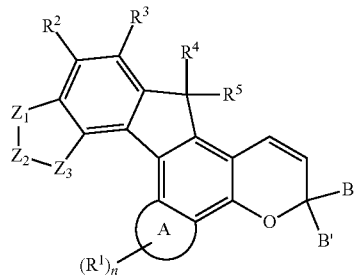

(I-A)

With reference to Formula (I-A), Ring-A is selected from aryl and fused ring aryl, and n is selected from 1 to 8.

With further reference to Formula (I-A), $R^1$, for each n, is in each case independently selected from hydrogen, hydrocarbyl and substituted hydrocarbyl each optionally and independently interrupted with at least one of —O—, —S—, —C(O)—, —C(O)O—, —S(O)—, —SO$_2$—, —N=N—, —N(R$_{11}$')— where R$_{11}$' is selected from hydrogen, hydrocarbyl or substituted hydrocarbyl, —Si(OR$_8$')$_w$(R$_8$')$_t$—, where w and t are each independently selected from 0 to 2, provided that the sum of w and t is 2, and each R$_8$' is independently selected from hydrogen, hydrocarbyl and substituted hydrocarbyl, and combinations of two or more thereof; halogen; cyano; —O—R$_{10}$' or —S—R$_{10}$' or —C(O)—R$_{10}$' or —C(O)—OR$_{10}$', wherein each R$_{10}$' is independently selected from hydrogen, hydrocarbyl or substituted hydrocarbyl; perhalohydrocarbyl; and —C(O)—N(R$_{11}$')(R$_{12}$') or —N(R$_{11}$')R$_{12}$', wherein R$_{11}$' and R$_{12}$' are each independently selected from hydrogen, hydrocarbyl or substituted hydrocarbyl, or R$_{11}$' and R$_{12}$' together form a ring structure optionally including at least one heteroatom.

With additional reference to Formula (I-A), $R^2$ and $R^3$ are each independently selected from hydrogen, hydrocarbyl, substituted hydrocarbyl, halogen, —C(O)—N(R$_{14}$)(R$_{15}$), —N(R$_{14}$)(R$_{15}$), —SR$_{16}$, and —OR$_{16}$, where R$_{14}$ and R$_{15}$ are each independently selected from hydrogen, hydrocarbyl, and substituted hydrocarbyl, or R$_{14}$ and R$_{15}$ together form a ring, and each R$_{16}$ is independently selected from hydrocarbyl and substituted hydrocarbyl.

With further additional reference to Formula (I-A), $R^4$ and $R^5$ are each independently selected from hydrogen, hydrocarbyl, and substituted hydrocarbyl, each optionally and independently interrupted with —O—, —S—, —N(R$_{11}$')—, where R$_{11}$' is selected from hydrogen, hydrocarbyl or substituted hydrocarbyl.

With additional further reference to Formula (I-A), $Z_1$ and $Z_3$ are each independently selected from O, C(O) and C(R$_a$)(R$_b$), where R$_a$ and R$_b$ are each independently selected from hydrogen, hydroxyl, and C$_1$-C$_{20}$ linear or branched alkyl, provided that at least one of $Z_1$ and $Z_3$ is C(O).

With still further reference to Formula (I-A), $Z_2$ is selected from O, S, divalent hydrocarbyl, and N—R$_{13}$, where R$_{13}$ is selected from hydrogen, hydrocarbyl and substituted hydrocarbyl each optionally and independently interrupted with at least one of —O—, —S—, —C(O)—, —C(O)O—, —S(O)—, —SO$_2$—, —N=N—, —N(R$_{11}$')— where R$_{11}$' is selected from hydrogen, hydrocarbyl or substituted hydrocarbyl, —Si(OR$_8$')$_w$(R$_8$')$_t$—, where w and t are each independently selected from 0 to 2, provided that the sum of w and t is 2, and each R$_8$' is independently selected from hydrogen, hydrocarbyl and substituted hydrocarbyl, and combinations of two or more thereof, or $Z_2$ defines an optionally substituted fused ring.

With still further additional reference to Formula (I-A), B and B' are each independently selected from, hydrogen, hydrocarbyl and substituted hydrocarbyl each optionally and independently interrupted with at least one of —O—, —S—, —C(O)—, C(O)O—, —S(O)—, —SO$_2$—, —N═N—, —N(R$_{11}$')— where R$_{11}$' is selected from hydrogen, hydrocarbyl or substituted hydrocarbyl, —Si(OR$_8$')$_w$(R$_8$')$_t$—, where w and t are each independently selected from 0 to 2, provided that the sum of w and t is 2, and each R$_8$' is independently selected from hydrogen, hydrocarbyl and substituted hydrocarbyl, and combinations of two or more thereof.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1-6 like characters refer to the same compounds, reactants, and/or groups as the case may be, unless otherwise stated.

DETAILED DESCRIPTION

Figure 1:
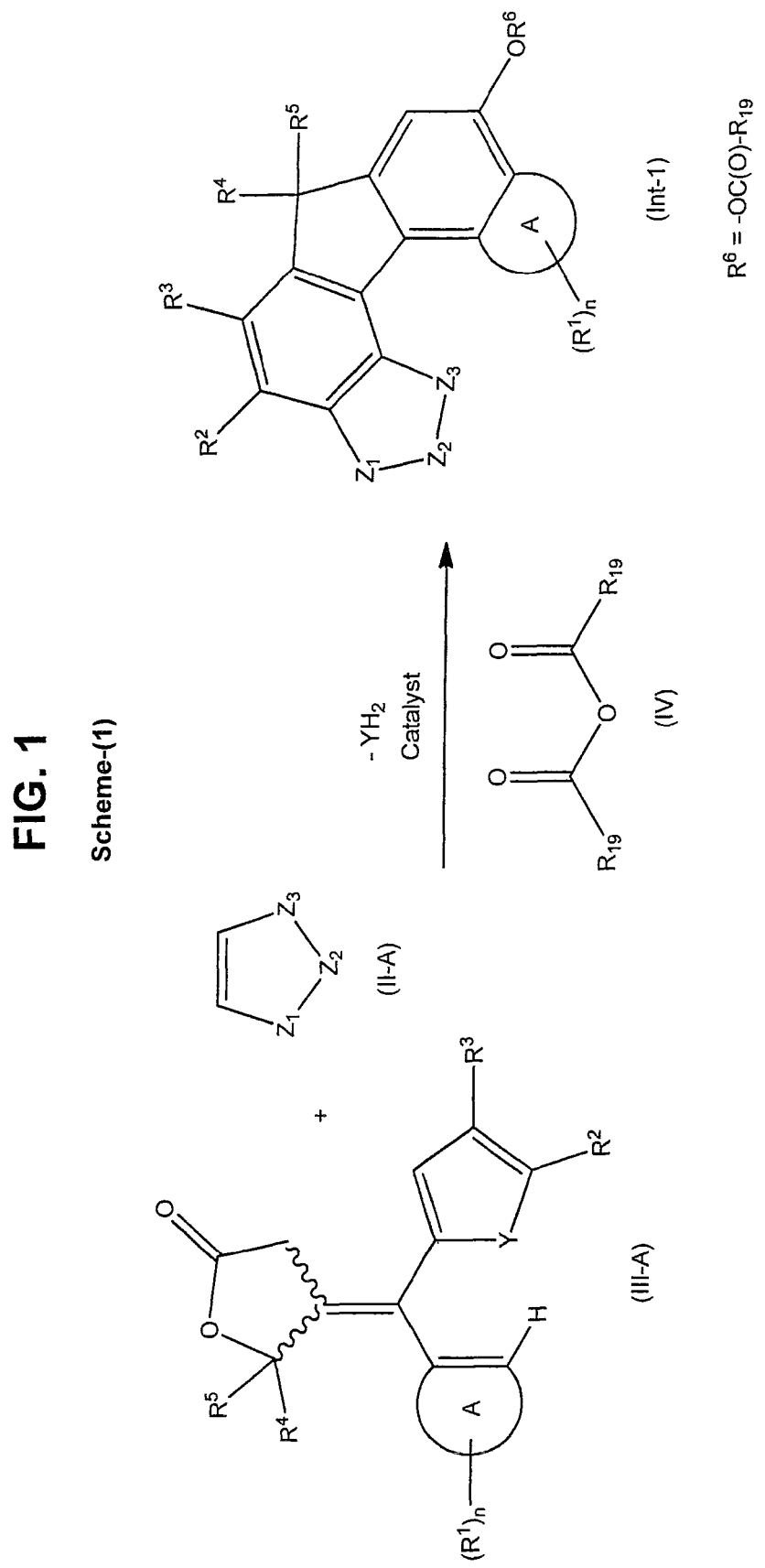
FIG. 1 is an illustrative representative general scheme, Scheme-(1), of a method for preparing an intermediate compound from which the photochromic indeno-fused ring pyran compounds of the present invention can be prepared, with some embodiments.

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

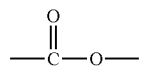

or equivalently —C(O)O—, is inclusive of the right-to-left representation thereof,

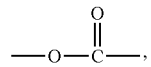

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

The photochromic compounds of the present invention are also referred to herein as photochromic indeno-fused ring pyran compounds.

The photochromic compounds of the present invention, as described herein, including, but not limited to, photochromic compounds represented by Formula (I-A) and Formula (I-B), and Formulas (I-B)-(1) through (I-B)-(17), in each case optionally further include one or more coproducts, resulting from the synthesis of such compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound prepared from the fused ring indeno compounds prepared by the method of the present invention can be clear in the first state and colored in the second state. Alternatively, a photochromic compound prepared from the fused ring indeno compounds prepared by the method of the present invention can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation there-through. Non-limiting examples of windows include automotive and aircraft transparencies, windshields, filters, shutters, and optical switches.

As used herein the term "mirror" means a surface that specularly reflects a large fraction of incident light.

As used herein the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, the term "Ring Position" means a particular position in the ring structure, such as the fused ring structure, of a chemical compound, such as the photochromic indeno-fused ring pyran compounds of the present invention, and which are depicted herein in accordance with some embodiments by numbers within the ring structures of representative chemical formulas.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R_{11}'$)($R_{12}'$) where $R_{11}'$ and $R_{12}'$ are each independently selected, with some embodiments, from hydrogen, linear or branched $C_1$-$C_{20}$ alkyl, $C_3$-$C_{12}$ cycloakyl, $C_3$-$C_{12}$ heterocycloalkyl, aryl, and heteroaryl.

As used herein, recitations of "halo substituted" and related terms (such as, but not limited to, haloalkyl groups, haloalkenyl groups, haloalkynyl groups, haloaryl groups and haloheteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F.

The photochromic indeno-fused ring pyran compounds of the present invention, such as but not limited to those represented by Formulas (I-A) and (I-B), include groups and subgroups that can in each case be independently selected from hydrocarbyl and/or substituted hydrocarbyl. As used herein the term "hydrocarbyl" and similar terms, such as "hydrocarbyl substituent," means: linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to imidazolyl, tetrahydrofuranyl, tetrahydropyranyl and piperidinyl. Representative aryl groups include but are not limited to phenyl, naphthyl, anthracynyl and triptycenyl. Representative heteroaryl groups include but are not limited to furanyl, pyranyl, pyridinyl, isoquinoline, and pyrimidinyl. Representative aralkyl groups include but are not limited to benzyl, and phenethyl.

The term "substituted hydrocarbyl" as used herein means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —$N(R_{11}')(R_{12}')$ where $R_{11}'$ and $R_{12}'$ are each independently selected from hydrogen, hydrocarbyl and substituted hydrocarbyl.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can each be independently selected, in some instances and with some embodiments, can in each case be independently and optionally interrupted with at least one of —O—, —S—, —C(O)—, —C(O)O—, —S(O)—, —SO$_2$—, —N=N—, —N($R_{11}'$)— where $R_{11}'$ is selected from hydrogen, hydrocarbyl or substituted hydrocarbyl, —Si(O$R_8'$)$_w$(R$_8'$)$_t$—, where w and t are each independently selected from 0 to 2, provided that the sum of w and t is 2, and each $R_8'$ is independently selected from hydrogen, hydrocarbyl and substituted hydrocarbyl, and combinations of two or more thereof. As used herein, by interrupted with at least one of —O—, —S—, —C(O)—, —C(O)O—, —OC(O)O—, —S(O)—, —SO$_2$—, —N=N—, —N($R_{11}'$)—, and —Si(O$R_8'$)$_w$(R$_8'$)$_t$—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two or more of the above recited linking groups, which can be adjacent to each other or separated by one or more carbons. For purposes of non-limiting illustration, a combination of adjacent —C(O)— and —N($R_{11}'$)— can provide a divalent amide linking or interrupting group, —C(O)—N($R_{11}'$)—. For purposes of further non-limiting illustration, a combination of adjacent —N($R_{11}'$)—, —C(O)— and —O— can provide a divalent carbamate (or urethane) linking or interrupting group, —N($R_{11}'$)—C(O)—O—, where $R_{11}'$ is hydrogen.

The term "alkyl" as used herein, in accordance with some embodiments, means linear or branched alkyl, such as but not limited to, linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, those recited previously herein. Alkyl groups of the various compounds of the present invention can, with some embodiments, include one or more unsaturated linkages selected from —CH=CH— groups and/or one or more —C≡C— groups, provided the alkyl group is free of two or more conjugated unsaturated linkages. With some embodiments, the alkyl groups are free of unsaturated linkages, such as —CH=CH— groups and —C≡C— groups.

The term "cycloalkl" as used herein, in accordance with some embodiments, means groups that are appropriately cyclic, such as but not limited to, $C_3$-$C_{12}$ cycloalkyl (including, but not limited to, cyclic $C_5$-$C_7$ alkyl) groups. Examples of cycloalkyl groups include, but are not limited to, those recited previously herein. The term "cycloalkyl" as used herein in accordance with some embodiments also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, in accordance with some embodiments, means groups that are appropriately cyclic, such as but not limited to, $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, those recited previously herein. The term "heterocycloalkyl" as used herein, in accordance with some embodiments, also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

The term "heteroaryl," as used herein, in accordance with some embodiments, includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, those recited previously herein.

As used herein, the term "fused ring polycyclic-aryl-alkyl group" and similar terms such as, fused ring polycyclic-alkylaryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl," as used herein, and in accordance with some embodiments, includes but is not limited to $C_6$-$C_{24}$ aralkyl, such as but not limited to $C_6$-$C_{10}$ aralkyl, and means an aryl group substituted with an alkyl group. Examples of aralkyl groups include, but are not limited to, those recited previously herein.

The photochromic indeno-fused ring pyran compounds according to the present invention, such as, but not limited to those represented by Formulas (I-A) and (I-B), and the various groups thereof are described in further detail herein as follows.

With some alternative embodiments, $Z_2$ of Formula (I-A) defines an optionally substituted fused ring. As used herein, the term "$Z_2$ defines an optionally substituted fused ring," means that $Z_2$ defines an optionally substituted fused ring that is bonded to both $Z_1$ and $Z_3$. In accordance with some further embodiments, the term "$Z_2$ defines an optionally substituted fused ring," does not include spiro compounds. For purposes of non-limiting illustration, and in accordance with some embodiments, when $Z_2$ defines an optionally substituted fused ring, the photochromic indeno-fused ring pyran compound represented by Formula (I-A) is represented by the following Formula (I-A'),

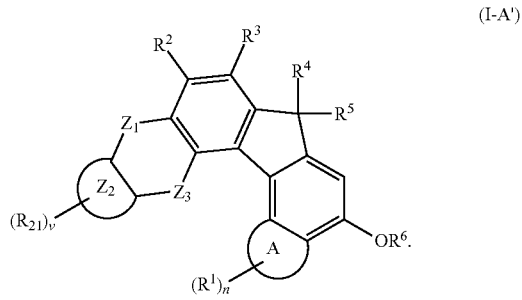

(I-A')

With reference to Formula (I-A'): Ring-$Z_2$ is selected from cyclocalkyl, heterocycloalkyl, aryl, and heteroaryl; v is selected from 1 to 8; and $R_{21}$ for each v is independently selected from hydrogen, cyano, nitro, halogen (such as, F, Cl, Br, and I), hydrocarbyl, substituted hydrocarbyl, and perhalohydrocarbyl. With some embodiments, Ring-$Z_2$ is selected from $C_6$-cycloalkyl (having 6 carbon atoms in the cycloalkyl ring) and $C_6$-aryl (having 6 carbon atoms in the aryl ring).

With reference to the photochromic indeno-fused ring pyran compound represented by Formula (I-A), Ring-A is selected from aryl.

With some embodiments of the present invention, $R^1$, for the photochromic indeno-fused ring pyran compounds represented by Formula (I-A), for each n, is independently selected from: hydrogen; halogen selected from fluoro, bromo, iodo, and chloro; $C_1$-$C_{20}$ linear or branched alkyl; $C_3$-$C_{10}$ cycloalkyl; substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy; —O—$R_{10}$' or —S—$R_{10}$', wherein each $R_{10}$' independently is hydrogen, $C_1$-$C_{20}$ alkyl, phenyl($C_1$-$C_{20}$)alkyl, mono($C_1$-$C_{20}$)alkyl substituted phenyl ($C_1$-$C_{20}$)alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl.

With some further embodiments, $R^1$, for Formula (I-A), for each n is independently selected from, —N($R_{11}$')$R_{12}$' or —C(O)—N($R_{11}$')($R_{12}$'), wherein $R_{11}$' and $R_{12}$' are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein the aryl group is phenyl or naphthyl, or $R_{11}$' and $R_{12}$' come together with the nitrogen atom to form a $C_3$-$C_{20}$ hetero-bicycloalkyl ring or a $C_4$-$C_{20}$ hetero-tricycloalkyl ring.

With some additional embodiments, $R^1$, for Formula (I-A), for each n is independently selected from, a nitrogen containing ring represented by the following graphic formula XIIA,

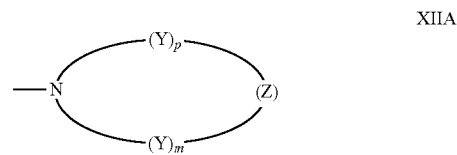

XIIA

With reference to Formula (XIIA), each —Y— is independently chosen for each occurrence from —$CH_2$—, —CH($R_{13}$')—, —C($R_{13}$)$_2$—, —CH(aryl)-, —C(aryl)$_2$-, and —C($R_{13}$')(aryl)-, and Z is —Y—, —O—, —S—, —S(O)—, —$SO_2$—, —NH—, —N($R_{13}$')—, or —N(aryl)-, wherein each $R_{13}$' is independently $C_1$-$C_{20}$ alkyl, each aryl is independently phenyl or naphthyl, m is an integer 1, 2 or 3, and p is an integer 0, 1, 2, or 3 and provided that when p is 0, Z is —Y—.

In accordance with some further embodiments, $R^1$, for Formula (I-A), for each n is independently selected from, a group represented by one of the following graphic formulas XIIB or XIIC,

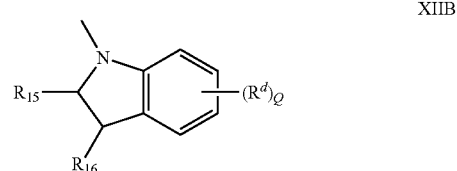

XIIB

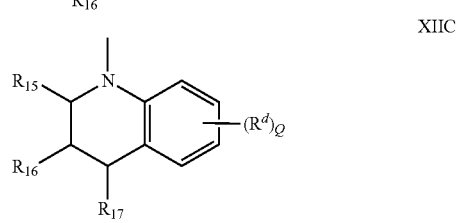

XIIC

With reference to Formulas (XIIB) and (XIIC), $R_{15}$, $R_{16}$, and $R_{17}$ are each independently hydrogen, $C_1$-$C_{20}$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3.

In accordance with some further embodiments, $R^1$, for Formula (I-A), for each n is independently selected from, unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_{20}$ alkyl, $C_1$-$C_{20}$ alkoxy, or phenyl($C_1$-$C_{20}$) alkyl.

With further reference to Formula (I-A), and in accordance with some embodiments, $R^2$ and $R^3$ are each independently selected from: hydrogen; halogen selected from F, Cl, Br, and I; $C_1$-$C_{20}$ linear or branched alkyl; $C_3$-$C_{10}$ cycloalkyl; and substituted or unsubstituted phenyl, in which the phenyl substituents are selected from hydroxyl, halogen, carbonyl, $C_1$-$C_{20}$ alkoxycarbonyl, cyano, halo($C_1$-$C_{20}$)alkyl, $C_1$-$C_{20}$ alkyl or $C_1$-$C_{20}$ alkoxy.

With some embodiments, $R^2$ and $R^3$ of Formula (I-A) are each independently selected from, —C(O)N($R_{14}$)($R_{15}$) or —N($R_{14}$)($R_{15}$), where $R_{14}$ and $R_{15}$ are each independently selected from: hydrogen; $C_1$-$C_{20}$ linear or branched alkyl; $C_3$-$C_{10}$ cycloalkyl; and substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy; or $R_{14}$ and $R_{15}$ together form a ring.

With some further embodiments, $R^2$ and $R^3$ of Formula (I-A) are each independently selected from, —O$R_{16}$ or —S$R_{16}$, where each $R_{16}$ is independently selected from: $C_1$-$C_{20}$ linear or branched alkyl; $C_3$-$C_{10}$ cycloalkyl; and substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy.

In accordance with some embodiments, $R^4$ and $R^5$ of Formula (I-A) are each independently selected from: (i) hydrogen, $C_1$-$C_{20}$ alkyl, $C_1$-$C_{20}$ haloalkyl, $C_3$-$C_{10}$ cycloalkyl, allyl, benzyl, or mono-substituted benzyl, said benzyl substituents being chosen from halogen, $C_1$-$C_{20}$ alkyl or $C_1$-$C_{20}$ alkoxy; (ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, $C_1$-$C_{20}$ alkyl or $C_1$-$C_{20}$ alkoxy; (iii) mono-substituted phenyl, said substituent located at the para position being —(CH$_2$)$_t$— or —O—(CH$_2$)$_t$—, wherein t is the integer 1, 2, 3, 4, 5 or 6, said substituent being connected to an aryl group which is a member of a photochromic material; and (iv) the group —CH($R^{10}$)G, wherein $R^{10}$ is hydrogen, $C_1$-$C_6$ alkyl or the unsubstituted, mono- or di-substituted aryl groups phenyl or naphthyl, and G is —CH$_2$O$R^{11}$, wherein $R^{11}$ is hydrogen, $C_1$-$C_{20}$ alkyl, $C_1$-$C_{20}$ alkoxy($C_1$-$C_{20}$)alkyl, phenyl($C_1$-$C_{20}$)alkyl, mono($C_1$-$C_{20}$)alkoxy substituted phenyl($C_1$-$C_{20}$)alkyl, or the unsubstituted, mono- or di-substituted aryl groups phenyl or naphthyl, each of said phenyl and naphthyl group substituents being $C_1$-$C_{20}$ alkyl or $C_1$-$C_{20}$ alkoxy.

With some alternative embodiments, (v) $R^4$ and $R^5$, of Formula (I-A), together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom, said spiro-carbocyclic ring and spiro-heterocyclic ring being annellated with 0, 1 or 2 benzene rings, said substituents being hydrogen or $C_1$-$C_{20}$ alkyl.

In accordance with some embodiments and with reference to Formula (I-A), B and B' are each independently selected from, hydrogen, unsubstituted aryl, substituted aryl, unsubstituted heteroaryl, and substituted heteroaryl, or B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

With further reference to Formula (I-A), and in accordance with some embodiments, B and B' are each independently an aryl group that is mono-substituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl. With some further embodiments, each of the phenyl, aryl and heteroaromatic substituents are each independently selected from: hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, $C_1$-$C_{20}$ alkyl, phenyl, mono($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and said halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$ cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$)alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$)alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen.

With some additional embodiments, B and B' of Formula (I-A) are each independently, an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{20}$ alkyl, $C_1$-$C_{20}$ alkoxy, phenyl, or halogen.

With some additional embodiments, B and B' of Formula (I-A) are each independently, a group represented by one of the following Formulas (XIVA) or (XIVB):

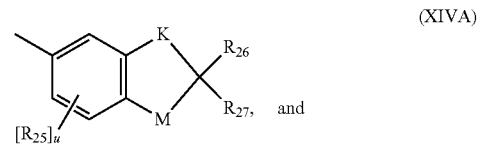

(XIVA)

and

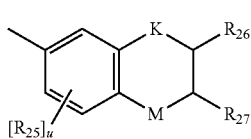

(XIVB)

Independently for Formulas (XIVA) and (XIVB), K is —CH$_2$— or —O—, and M is —O— or substituted nitrogen, provided that when M is substituted nitrogen, K is —CH$_2$—, the substituted nitrogen substituents being hydrogen, C$_1$-C$_{20}$ alkyl, or C$_1$-C$_{20}$ acyl, each R$_{25}$ being independently chosen for each occurrence from C$_1$-C$_{20}$ alkyl, C$_1$-C$_{20}$ alkoxy, hydroxy, and halogen, R$_{26}$ and R$_{27}$ each being independently hydrogen or C$_1$-C$_{20}$ alkyl, and u is an integer ranging from 0 to 2.

With some additional embodiments, B and B' of Formula (I-A) are each independently selected from a group represented by the following Formula (XV):

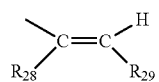

(XV)

With reference to Formula (XV), R$_{28}$ is hydrogen or C$_1$-C$_{20}$ alkyl, and R$_{29}$ is an unsubstituted, mono-, or di-substituted group chosen from naphthyl, phenyl, furanyl, and thienyl, wherein the substituents are C$_1$-C$_{20}$ alkyl, C$_1$-C$_{20}$ alkoxy, or halogen.

In accordance with some alternative embodiments, B and B' of Formula (I-A) taken together form one of a fluoren-9-ylidene, mono-, or di-substituted fluoren-9-ylidene, each of said fluoren-9-ylidene substituents being independently chosen from C$_1$-C$_{20}$ alkyl, C$_1$-C$_{20}$ alkoxy, and halogen.

With some embodiments of the present invention, the photochromic indeno-fused ring pyran, such as represented by Formula (I-A), Ring-A is C$_6$-aryl.

With some further embodiments, R$^1$, of the photochromic indeno-fused ring pyran represented by Formula (I-A), for each n is independently selected from hydrogen, C$_1$-C$_6$ linear or branched alkyl, C$_3$-C$_7$ cycloalkyl, C$_1$-C$_8$ haloalkyl, fluoro, chloro, bromo, iodo, and —O—R$^{10'}$.

With additional reference to Formula (I-A) and with some embodiments, R$^2$ and R$^3$ are each independently selected from: hydrogen; C$_1$-C$_6$ linear or branched alkyl; C$_3$-C$_7$ cycloalkyl; and substituted or unsubstituted phenyl, in which the phenyl substituents are in each case independently selected from halogen, halo(C$_1$-C$_6$)alkyl, C$_1$-C$_6$ alkyl or C$_1$-C$_6$ alkoxy.

With further reference to Formula (I-A) and with some further embodiments, R$^4$ and R$^5$ are each independently selected from hydrogen, C$_1$-C$_8$ alkyl, C$_1$-C$_8$ haloalkyl, and C$_3$-C$_7$ cycloalkyl, or R$^4$ and R$^5$ together form a spiro substituent selected from a substituted or unsubstituted spiro-carbocyclic ring containing 3 to 6 carbon atoms.

In accordance with some further embodiments, B and B' of Formula (I-A) are each independently selected from phenyl, and phenyl substituted with at least one of fluoro, C$_1$-C$_6$ alkyl, C$_1$-C$_6$ alkoxy, morpholino, piperidino, and pyrrolidino.

With reference to the photochromic compound represented by Formula (I-A), and in accordance with some embodiments, Z$_2$ is N—R$_{13}$, and R$_{13}$ is a group L represented by the following Formula (II), and optionally at least one R$^1$ independently for each n, is selected from the group L represented by the following Formula (II),

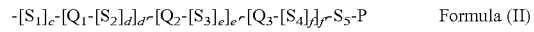

-[S$_1$]$_c$-[Q$_1$-[S$_2$]$_d$]$_{d'}$-[Q$_2$-[S$_3$]$_e$]$_{e'}$-[Q$_3$-[S$_4$]$_f$]$_{f'}$-S$_5$-P        Formula (II)

With reference to Formula (II), and in accordance with some embodiments, (a) Q$_1$, Q$_2$, and Q$_3$ for each occurrence, are independently selected from a divalent group selected from optionally substituted aryl, optionally substituted heteroaryl, optionally substituted cycloalkyl, and optionally substituted heterocycloalkyl. The aryl substituents, heteroaryl substituents, cycloalkyl substituents, and heterocycloalkyl substituents are, with some embodiments, each independently selected from P (as described in further detail below), liquid crystal mesogens, halogen, poly(C$_1$-C$_{18}$ alkoxy), C$_1$-C$_{18}$ alkoxycarbonyl, C$_1$-C$_{18}$ alkylcarbonyl, C$_1$-C$_{18}$ alkoxycarbonyloxy, aryloxycarbonyloxy, perfluoro(C$_1$-C$_{18}$) alkoxy, perfluoro(C$_1$-C$_{18}$)alkoxycarbonyl, perfluoro(C$_1$-C$_{18}$)alkylcarbonyl, perfluoro(C$_1$-C$_{18}$)alkylamino, di-(perfluoro(C$_1$-C$_{18}$)alkyl)amino, perfluoro(C$_1$-C$_{18}$)alkylthio, C$_1$-C$_{18}$ alkylthio, C$_1$-C$_{18}$ acetyl, C$_3$-C$_{10}$ cycloalkyl, C$_3$-C$_{10}$ cycloalkoxy, straight-chain C$_1$-C$_{18}$ alkyl, and branched C$_1$-C$_{18}$ alkyl. The straight-chain C$_1$-C$_{18}$ alkyl and branched C$_1$-C$_{18}$ alkyl, with some embodiments, are mono-substituted with a group selected from cyano, halogen, and C$_1$-C$_{18}$ alkoxy. Alternatively, and with some embodiments, the straight-chain C$_1$-C$_{18}$ alkyl and branched C$_1$-C$_{18}$ alkyl are poly-substituted with at least two groups independently selected from halogen, -M(T)$_{(v-1)}$ and -M(OT)$_{(v-1)}$, in which M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M.

With further reference to Formula (II), and in accordance with some further embodiments, (b) c, d, e, and f are each independently chosen from an integer of 1 to 20; and each S$_1$, S$_2$, S$_3$, S$_4$, and S$_5$ is independently chosen for each occurrence from a spacer unit selected from (i), (ii), and (iii) as described as follows. With some embodiments, each S$_1$, S$_2$, S$_3$, S$_4$ and S$_5$ is independently chosen for each occurrence from a spacer unit selected from (i) optionally substituted alkylene, optionally substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from C$_1$-C$_{18}$ alkyl, C$_3$-C$_{10}$ cycloalkyl and aryl. With some further embodiments, each S$_1$, S$_2$, S$_3$, S$_4$, and S$_5$ is independently chosen for each occurrence from a spacer unit selected from (ii) —N(Z)—, —C(Z)=C(Z)—, —C(Z)=N—, —C(Z')$_2$—C(Z')$_2$—, and a single bond, wherein Z for each occurrence is independently selected from hydrogen, C$_1$-C$_{18}$ alkyl, C$_3$-C$_{10}$ cycloalkyl and aryl, and Z' for each occurrence is independently selected from C$_1$-C$_{18}$ alkyl, C$_3$-C$_{10}$ cycloalkyl and aryl. With some additional embodiments, each S$_1$, S$_2$, S$_3$, S$_4$, and S$_5$ is independently chosen for each occurrence from a spacer unit selected from (iii) —O—, —C(=O)—, —C≡C—, —N=N—, —S—, —S(=O)—, —(O=)S(=O)—, —(O=)S(=O)O—, —O(O=)S(=O) O— and straight-chain or branched C$_1$-C$_{24}$ alkylene residue, said C$_1$-C$_{24}$ alkylene residue being unsubstituted, mono-substituted by cyano or halogen, or poly-substituted by halogen. With further reference to each of S$_1$, S$_2$, S$_3$, S$_4$, and S$_5$, and with some embodiments, there is the proviso that when two spacer units comprising heteroatoms are linked together the spacer units are linked so that heteroatoms are not directly linked to each other. There is a further proviso, with some embodiments, that each bond between $S_1$ and the nitrogen atom of N—$R_{13}$ of the photochromic compound represented by Formula (I-A) is in each case free of two heteroatoms linked together, and the bond between $S_5$ and P is free of two heteroatoms linked to each other.

With further reference to Formula (II), and in accordance with some further embodiments, (c) P for each occurrence is independently selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_8$)alkyl, polyethyleneoxy, polypropyleneoxy, ethylene, acryloyl, acryloyloxy($C_1$-$C_{18}$)alkyl, methacryloyl, methacryloyloxy ($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$) alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$) alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound.

With additional reference to Formula (II), and in accordance with some further embodiments, (d) d', e' and f' are each independently chosen from 0, 1, 2, 3, and 4, provided that the sum of d'+e'+f' is at least 1.

In accordance with some embodiments, for the group L represented by Formula (II), (a) $Q_1$, $Q_2$, and $Q_3$ for each occurrence, are independently selected from optionally substituted aryl and optionally substituted cycloalkyl.

With further reference to Formula (II), and in accordance with some further embodiments, (b) each $S_1$, $S_2$, $S_3$, $S_4$, and $S_5$ of Formula (VII) is independently chosen for each occurrence from a spacer unit selected from (ii) and (iii) as described as follows. Each $S_1$, $S_2$, $S_3$, $S_4$, and $S_5$ of Formula (VII), with some embodiments, is independently chosen for each occurrence from a spacer unit selected from (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl. Each $S_1$, $S_2$, $S_3$, $S_4$, and $S_5$ of Formula (VII), with some further embodiments, is independently chosen for each occurrence from a spacer unit selected from (iii) —O—, —C(=O)—, —C≡C—, —N=N—, —S—, —S(=O)—, and straight-chain or branched $C_1$-$C_{12}$ alkylene residue, said $C_1$-$C_{12}$ alkylene residue being unsubstituted, mono-substituted by cyano or halogen, or poly-substituted by halogen.

In accordance with some additional embodiments, for the group L represented by Formula (II), (c) P for each occurrence is independently selected from hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$-$C_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$) alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$) alkoxy, $C_1$-$C_8$ alkoxy($C_1$-$C_8$)alkoxy, nitro, poly($C_1$-$C_8$)alkyl ether, ($C_1$-$C_8$)alkyl($C_1$-$C_8$)alkoxy($C_1$-$C_8$)alkyl, polyethyleneoxy, polypropyleneoxy, ethylene, acryloyl, acryloyloxy ($C_1$-$C_{18}$)alkyl, methacryloyl, methacryloyloxy($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, and vinyl ester.

In accordance with some further additional embodiments, for the group L represented by Formula (II), (b) each $S_1$, $S_2$, $S_3$, $S_4$, and $S_5$ is independently chosen for each occurrence from a spacer unit selected from: (ii) —N(Z)—, —C(Z)=C(Z)—, and a single bond, wherein Z for each occurrence is independently selected from hydrogen, $C_1$-$C_8$ alkyl, $C_3$-$C_6$ cycloalkyl and aryl; and (iii) —O—, —C(=O)—, —C≡C—, and straight-chain or branched $C_1$-$C_6$ alkylene residue, said $C_1$-$C_6$ alkylene residue being unsubstituted, mono-substituted by cyano or halogen, or poly-substituted by halogen.

In accordance with some additional further embodiments, for the group L represented by Formula (II), (c) P for each occurrence is independently selected from hydrogen, hydroxy, amino, $C_2$-$C_8$ alkenyl, $C_2$-$C_8$ alkynyl, and aryl.

In accordance with some embodiments of the present invention, each group L as represented by Formula (II) is independently selected from the following non-limiting groups:

L(1) 4-[4-(4-butyl-cyclohexyl)-phenyl]-cyclohexyloxy

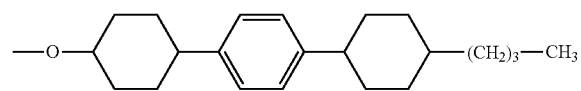

L(2) 4"-butyl-[1,1';4',1"]tercyclohexan-4-yloxy

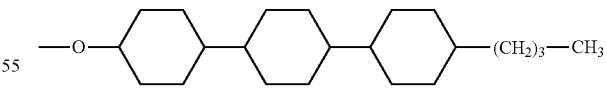

L(3) 4-[4-(4-butyl-phenyl)-cyclohexyloxycarbonyl]-phenoxy

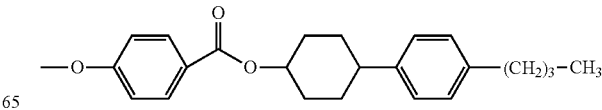

L(4) 4'-(4-butyl-benzoyloxy)-biphenyl-4-carbonyloxy

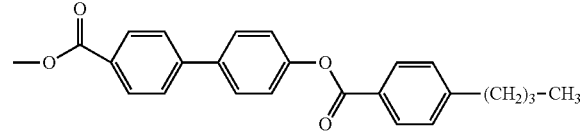

L(5) 4-(4-pentyl-phenylazo)-phenylcarbamoyl

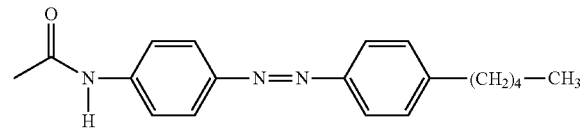

L(6) 4-(4-dimethylamino-phenylazo)-phenylcarbamoyl

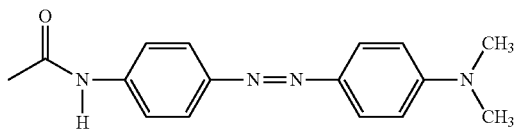 [SMILES: CC(=O)Nc1ccc(N=Nc2ccc(N(C)C)cc2)cc1]

L(7) {4-[5-(4-propyl-benzoyloxy)-pyrimidin-2-yl]-phenyl}ester

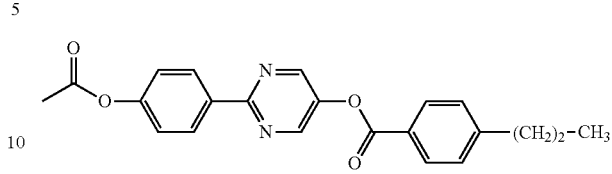

L(8) {4-[2-(4'-methyl-biphenyl-4-carbonyloxy)-1,2-diphenyl-ethoxycarbonyl]-phenyl}ester

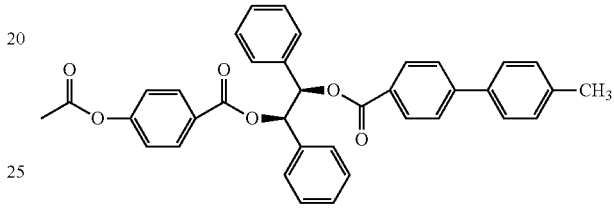

L(9) [4-(1,2-diphenyl-2-{3-[4-(4-propyl-benzoyloxy)-phenyl]-acryloyloxy}-ethoxycarbonyl)-phenyl]ester

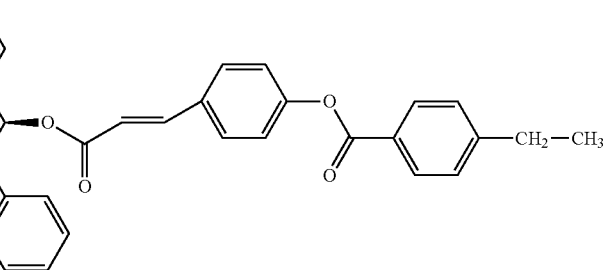

L(10) 4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl-piperazin-1-yl

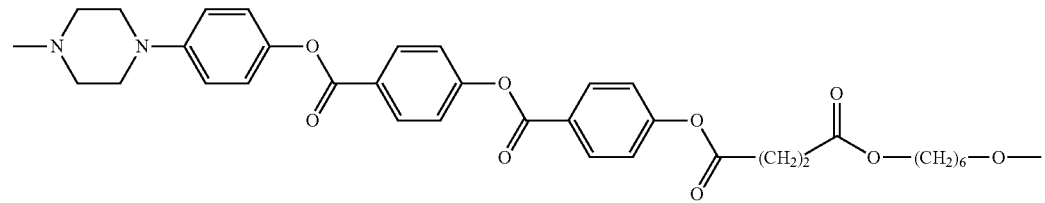

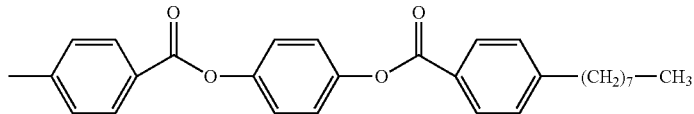

L(11) {4-[4-(4-{4-[4-(4-nonyl-benzoyloxy)-benzoyloxy]-benzoyloxy}-benzoyloxy)-phenyl]-piperazin-1-yl}

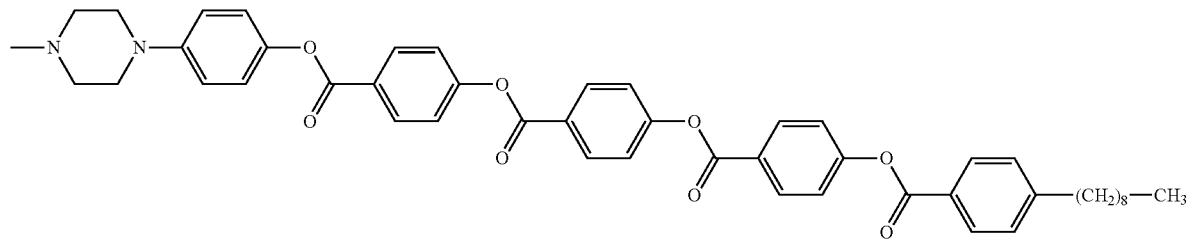

L(12) 4-(4'-propyl-biphenyl-4-ylethynyl)-phenyl

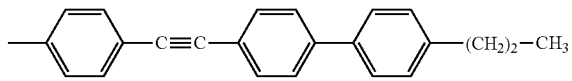

L(13) 4-(4-fluoro-phenoxycarbonyloxy)-piperidin-1-yl

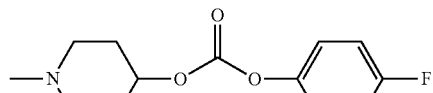

L(14) 2-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-indan-5-yl

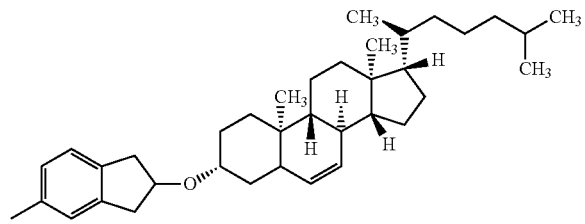

L(15) 4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl

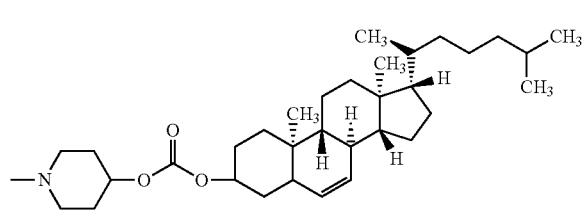

L(16) 4-(biphenyl-4-carbonyloxy)-piperidin-1-yl

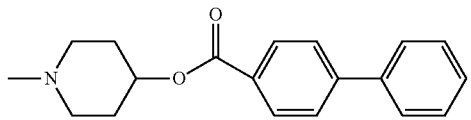 [SMILES: CN1CCC(OC(=O)c2ccc(-c3ccccc3)cc2)CC1]

L(17) 4-(naphthalene-2-carbonyloxy)-piperidin-1-yl

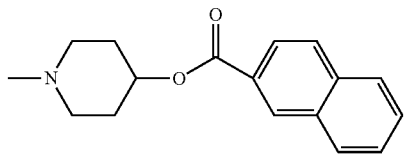 [SMILES: CN1CCC(OC(=O)c2ccc3ccccc3c2)CC1]

L(18) 4-hydroxy-piperidin-1-yl

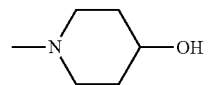

L(19) 4-(4-phenylcarbamoyl-phenylcarbamoyl)-piperidin-1-yl

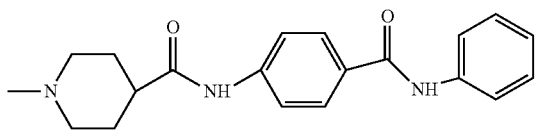 [SMILES: CN1CCC(C(=O)Nc2ccc(C(=O)Nc3ccccc3)cc2)CC1]

L(20) 4-(4-(4-phenylpiperidin-1-yl)-benzoyloxy)-piperidin-1-yl

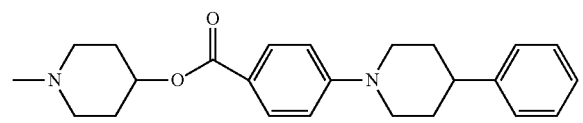 [SMILES: CN1CCC(OC(=O)c2ccc(N3CCC(c4ccccc4)CC3)cc2)CC1]

L(21) 4-butyl-[1,1';4',1'']terphenyl-4-yl

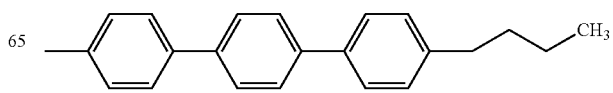

L(22) 4-(4-pentadecafluoroheptyloxy-phenylcarbamoyl)-benzyloxy

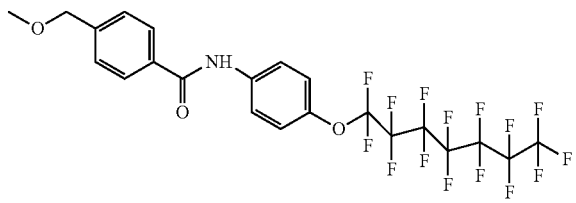 [SMILES: COCc1ccc(C(=O)Nc2ccc(OC(F)(F)C(F)(F)C(F)(F)C(F)(F)C(F)(F)C(F)(F)C(F)(F)F)cc2)cc1]

L(23) 4-(3-piperidin-4-yl-propyl)-piperidin-1-yl

L(24) 4-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-benzoyloxy}-phenoxycarbonyl)-phenoxymethyl L(25) 4-[4-(4-cyclohexyl-phenylcarbamoyl)-benzyloxy]-piperidin-1-yl L(26) 4-[4-(4-cyclohexyl-phenylcarbamoyl)-benzoyloxy]-piperidin-1-yl

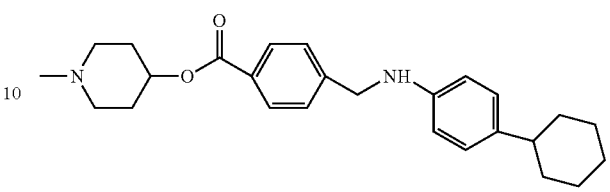

L(27) N-{4-[(4-pentyl-benzylidene)-amino]-phenyl}-acetamidyl

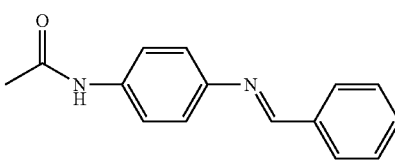

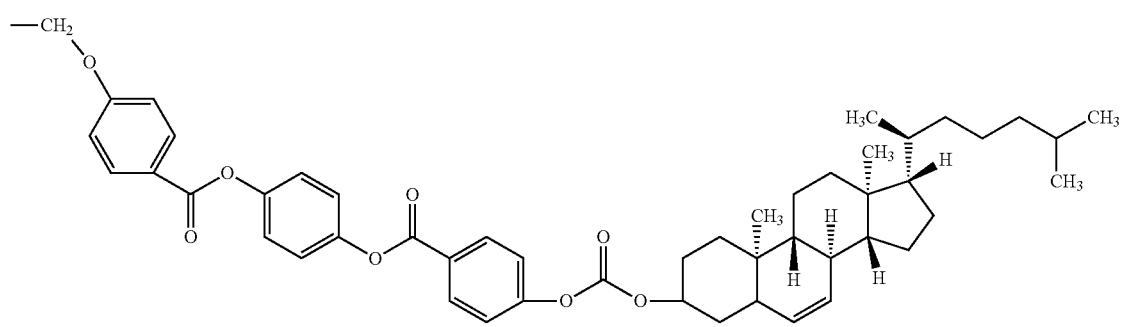

L(28) 4-(3-piperidin-4-yl-propyl)-piperidin-1-yl

L(29) 4-(4-hexyloxy-benzoyloxy)-piperidin-1-yl]

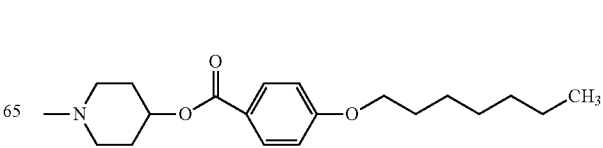

L(30) 4-(4'-hexyloxy-biphenyl-4-carbonyloxy)-piperidin-1-yl

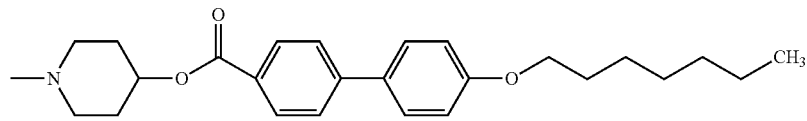

L(31) 4-(4-butyl-phenylcarbamoyl)-piperidin-1-yl

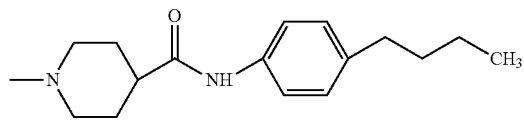 [SMILES: CCCCc1ccc(NC(=O)C2CCN(C)CC2)cc1]

L(32a) 1-methyl-4-((4'-(((1-methylpiperidin-4-yl)oxy)carbonyl)-[1,1'-biphenyl]-4-carbonyl)oxy)piperidin-1-yl

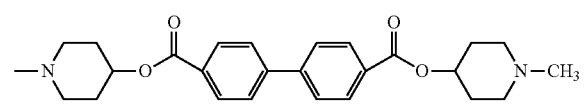

L(32b) bis(1-yl-piperidin-4-yl) [1,1'-biphenyl]-4,4'-dicarboxylate (which links two separate photochromic PC groups)

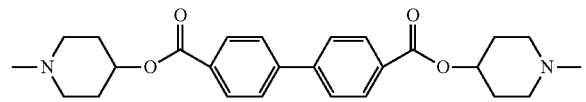

L(33) 4-(4-(9-(4-butylphenyl)-2,4,8,10-tetraoxaspiro[5.5]undec-3-yl)phenyl)piperazin-1-yl

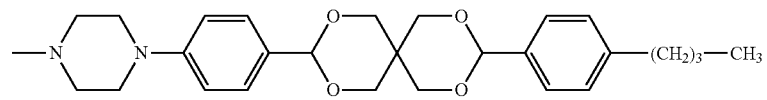

L(34) 4-(6-(4-butylphenyl)carbonyloxy-(4,8-dioxabicyclo[3.3.0]oct-2-yl))oxycarbonyl)pheny

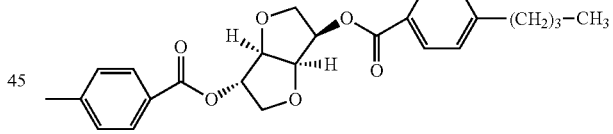

L(35) 1-{4-[5-(4-butyl-phenyl)-[1,3]dioxan-2-yl]-phenyl}-4-methyl-piperazin-1-yl

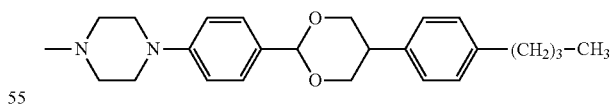

L(36) 4-(7-(4-propylphenylcarbonyloxy)bicyclo[3.3.0]oct-2-yl)oxycarbonyl)phenyl

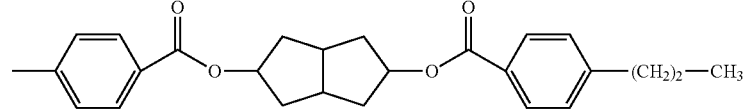

L(37) 4-[17-(1,5-dimethyl-hexyl)-10,13-dimethyl-2,3,4,7,8,
9,10,11,12,13,14,15,16,17-tetradecahydro-1H-cyclopenta
[a]phenanthren-3-yloxycarbonyloxy
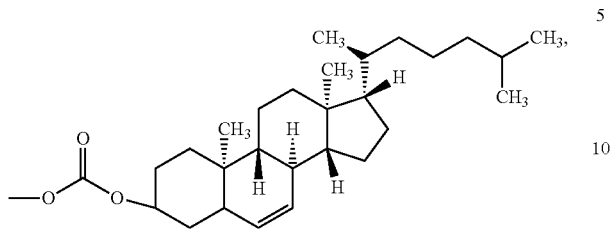
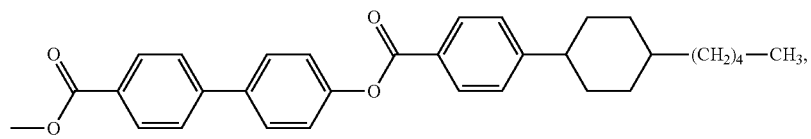
L(a)
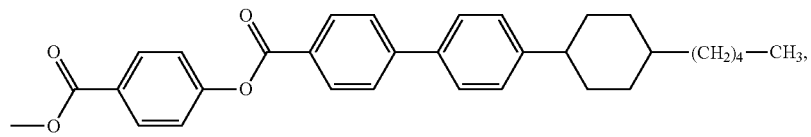
L(b)
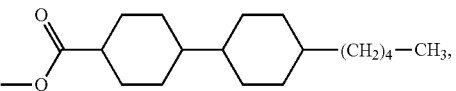
L(c)
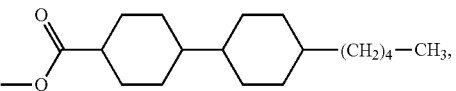
L(d)
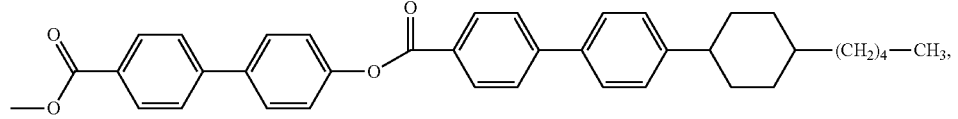
L(e)
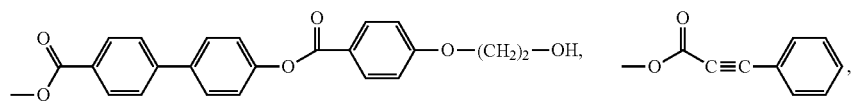
L(f)                                L(g)
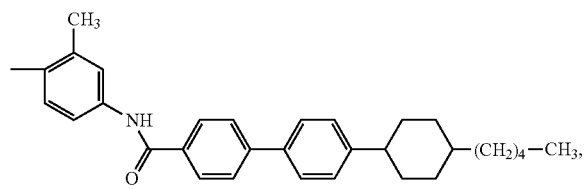
L(h)
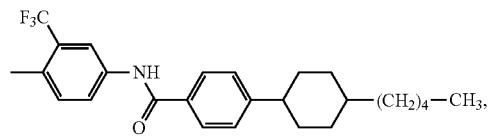
L(i)                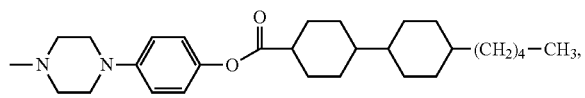
L(j)
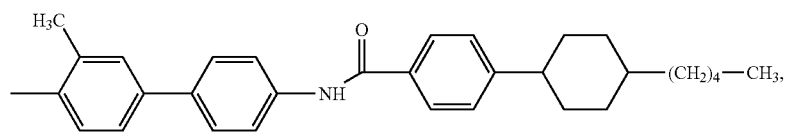
L(k)
L(l)

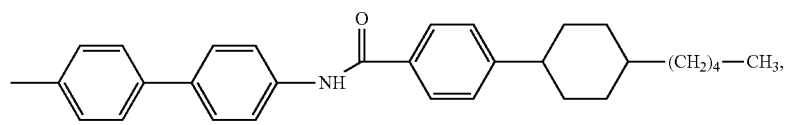
L(m)
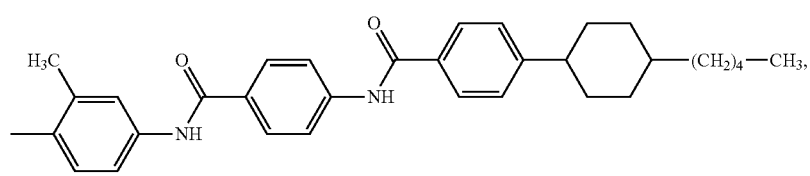
L(n)
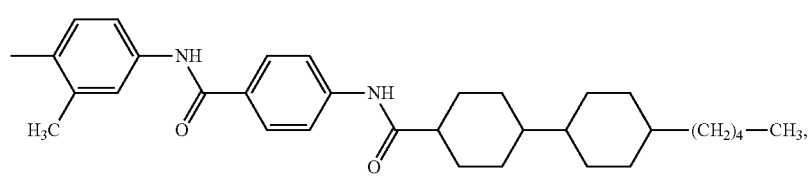
L(o)
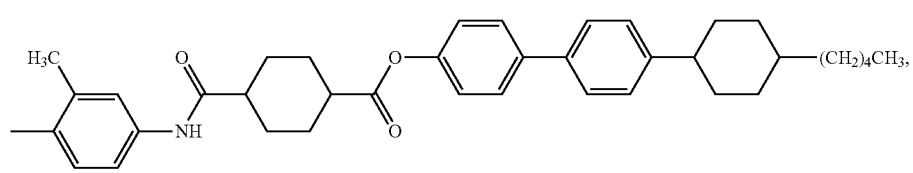
L(p)
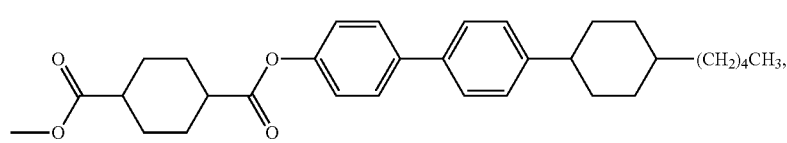
L(q)
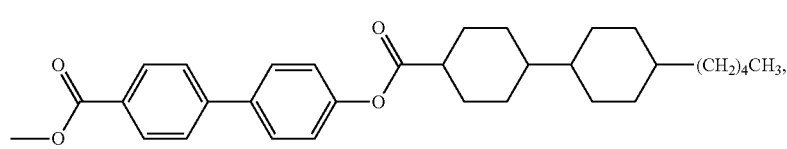
L(r)
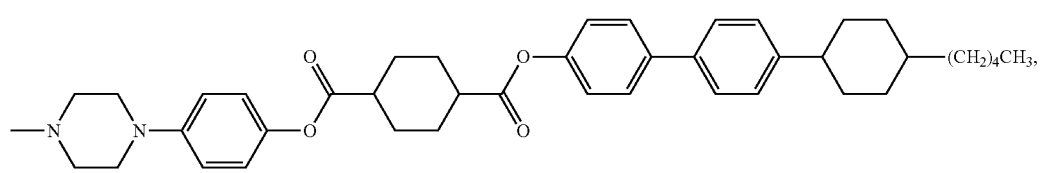
L(s)
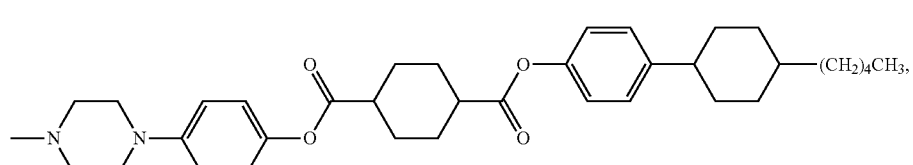
L(t)
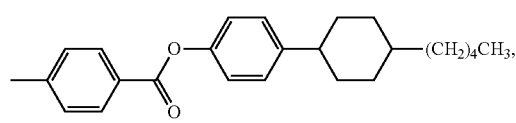
L(u)
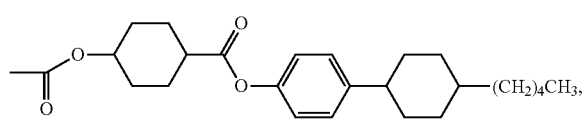
L(v)
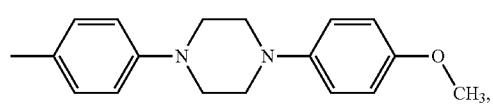
L(w)

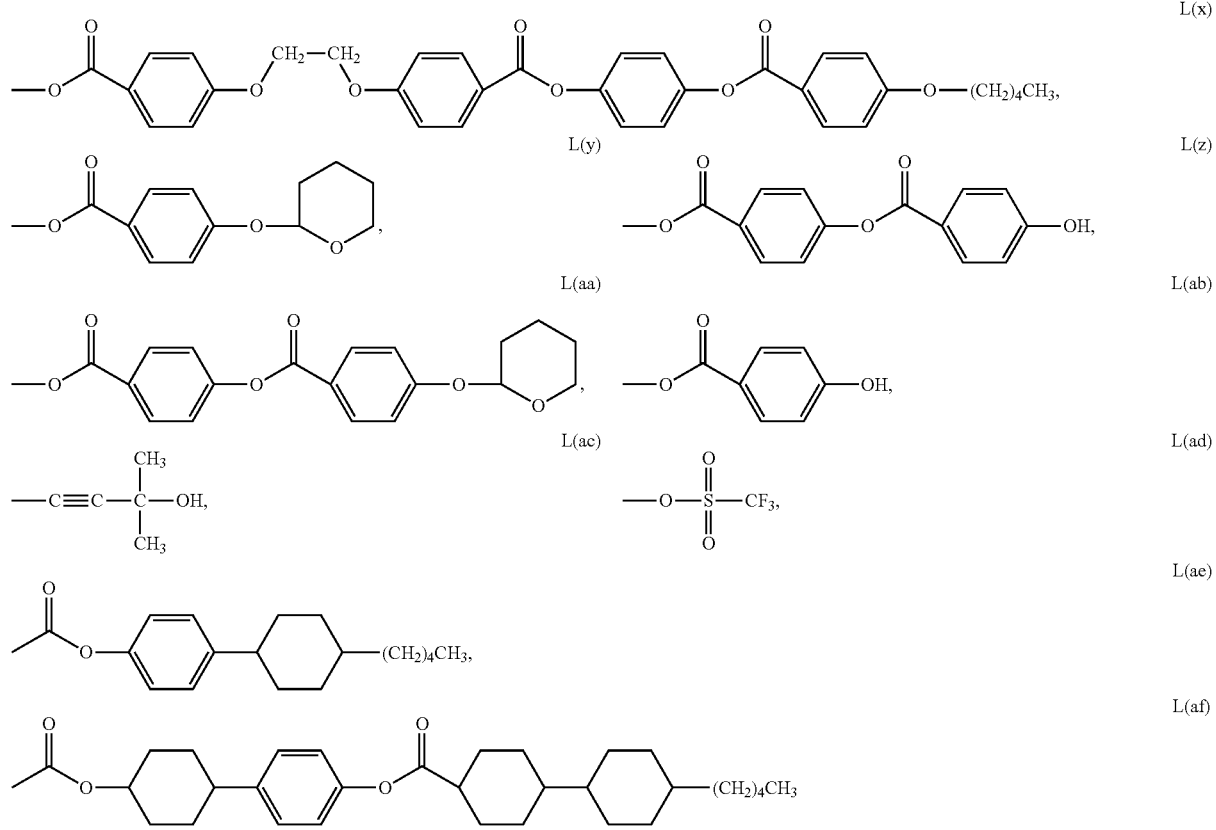

L-DC-(a) (4-trans-(4-pentylcyclohexyl)benzamido)phenyl,
L-DC-(b) (4-(4-trans-(4-pentylcyclohexyl)phenoxy)carbonyl)phenyl,
L-DC-(c) 4-(4-(4-trans-(4-pentylcyclohexyl)phenyl)benzamido) phenyl,
L-DC-(d) 4-((trans-(4'-pentyl-[1,1'-bi(cyclohexan)]-4-yl)oxy)carbonyl)phenyl,
L-DC-(e) 4-(4'-(4-pentylcyclohexyl)-[, 1'-biphenyl]-4-ylcarboxamido)phenyl,
L-DC-(f) 4-((4'-(4-pentylcyclohexyl)-[1,1'-biphenyl]-4-carbonyl)oxy)benzamido,
L-DC-(g) 4-(4'-(4-pentylcyclohexyl)-[, 1'-biphenyl]-4-carbonyl)piperazin-1-yl,
L-DC-(h) 4-(4-(4-trans-(4-pentylcyclohexyl)phenyl)benzamido)-2-(trifluoromethyl)phenyl,
L-DC-(i) 2-methyl-4-trans-(4-((4'-trans-(4-pentylcyclohexyl)biphenyl-4-yloxy)carbonyl)cyclohexanecarboxamido)phenyl,
L-DC-(j) 4'-(4'-pentylbi(cyclohexane-4-)carbonyloxy)biphenylcarbonyloxy,
L-DC-(k) 4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl, and
L-DC-(l) 4-((S)-2-methylbutoxy)phenyl)-10-(4-(((3R,3aS,6S,6aS)-6-(4'-trans-(4-pentylcyclohexyl)biphenylcarbonyloxy)hexahydrofuro[3,2-b]furan-3-yloxy)carbonyl)phenyl, With regard to the above non-limiting examples of L groups, there is the proviso that that $R_{13}$ of $N-R_{13}$ is only selected from L(5), L(6), L(7), L(8), L(9), L(12), L(14), L(21), L(24), L(27), L(34), L(36), L(h), L(i), L(j), L(l), L(m), L(n), L(ñ), L(o), L(p), L(u), L(v), L(w), L(ac), L(ae), L(af), L-DC-(a), L-DC-(b), L-DC-(c), L-DC-(d), L-DC-(e), L-DC-(h), L-DC-(i), and L-DC-(l).

In accordance with some embodiments, the photochromic compound represented by Formula (I-A), after formation thereof, can be subjected to one or more additional chemical reactions for purposes of modifying $R_{13}$ (when group $Z_2$ is $N-R_{13}$), such that $R_{13}$ is, or is converted to, an L group (or group L) as described previously herein with reference to Formula (II). Examples of additional chemical reactions that the photochromic compound represented by Formula (I-A) can be subjected to include, but are not limited to, palladium-catalyzed cross couplings, etherifications, esterifications, amidations, and condensations.

In accordance with some embodiments of the present invention, $Z_1$ and $Z_3$ of Formula (I-A) are each C(O).

The photochromic indeno-fused ring pyran compound of the present invention, such as represented by Formula (I-A), is, with some embodiments, a photochromic-dichroic compound. With the photochromic-dichroic compounds of the present invention, such as represented by Formula (I-A), and in accordance with some embodiments, $Z_2$ is $N-R_{13}$, and $R_{13}$ is a group L represented by Formula (II), and optionally at least one $R^1$ independently for each n, is selected from a group L represented by Formula (II), as described previously herein. With some embodiments, the photochromic-dichroic compounds of the present invention include one or more non-limiting examples of L groups as described previously herein, such as L(1) through L-DC-(l).

The photochromic indeno-fused ring pyran compounds of the present invention, such as represented by Formula (I-A), are, with some embodiments, represented by the following Formula (I-B):

(I-B)

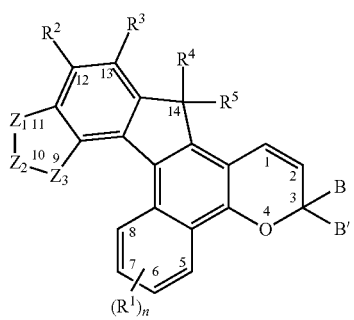

With reference to Formula (I-B), n is selected from 1 to 4, and $R^1$-$R^5$, $Z_1$-$Z_3$, B, and B' are each as described herein with regard to Formula (I-A). With further reference to Formula (I-B), the ring that includes $Z_1$-$Z_3$ is bonded to both ring positions of the indeno portion of the structure as depicted in Formula (I-B).

Examples of photochromic compounds according to the present invention, based on Formula (I-B), include, but are not limited to, those represented by the following Formulas (I-B)-(1) through (I-B)-(17):

(I-B)-(1) 3-(4-methoxyphenyl)-12,14,14-trimethyl-9,11-dioxo-3-phenyl-3,9,11,14-tetrahydrofuro[3',4':4,5]indeno[2',3':3,4]naphtho[1,2-b]pyran

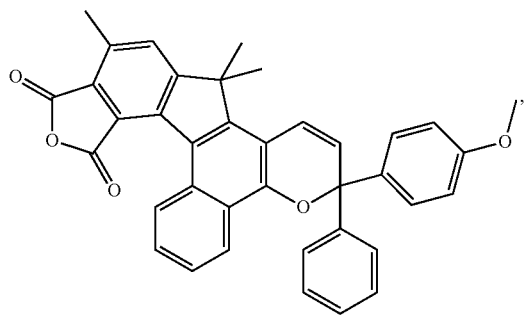 [SMILES: COc1ccc(C2(c3ccccc3)C=Cc3c4c(c5ccccc5c3O2)-c2c(cc(C)c3c2C(=O)OC3=O)C4(C)C)cc1]

(I-B)-(2) 3-(4-butoxyphenyl)-6-fluoro-3-(4-fluorophenyl)-14,14-dimethyl-9,11-dioxo-3,9,11,14-tetrahydrofuro[3',4':4,5]indeno[2',3':3,4]naphtho[1,2-b]pyran

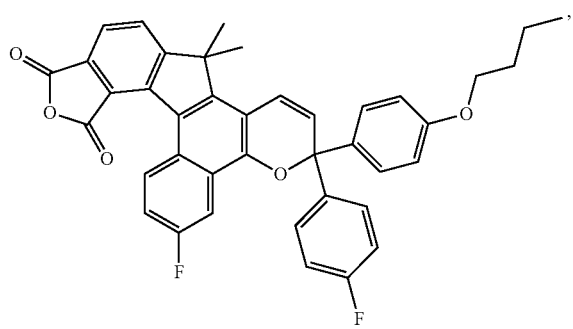 [SMILES: CCCCOc1ccc(C2(c3ccc(F)cc3)C=Cc3c4c(c5ccc(F)cc5c3O2)-c2c(ccc3c2C(=O)OC3=O)C4(C)C)cc1]

(I-B)-(3) 3-(4-methoxyphenyl)-14,14-dimethyl-9,11-dioxo-3-phenyl-12-(2-(2-phenylpropan-2-yl))-3,9,11,14-tetrahydrofuro[3',4':4,5]indeno[2',3':3,4]naphtho[1,2-b]pyran

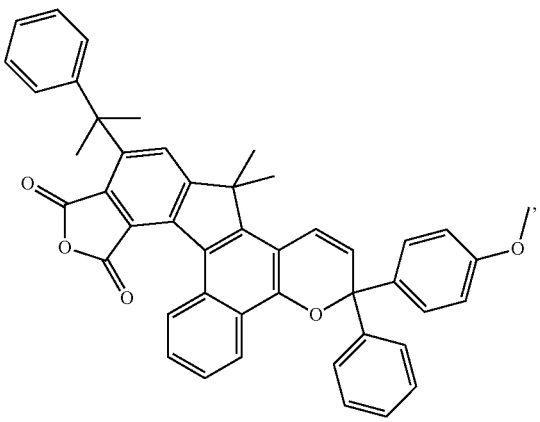 [SMILES: COc1ccc(C2(c3ccccc3)C=Cc3c4c(c5ccccc5c3O2)-c2c(cc(C(C)(C)c3ccccc3)c3c2C(=O)OC3=O)C4(C)C)cc1]

(I-B)-(4) 3-(4-methoxyphenyl)-14,14-dimethyl-11-oxo-3-phenyl-12-(2-(2-phenylpropan-2-yl))-3,9,11,14-tetrahydrofuro[3',4':4,5]indeno[2',3':3,4]naphtho[1,2-b]pyran

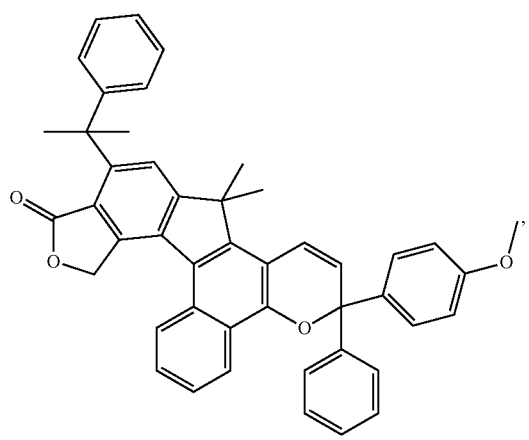 [SMILES: COc1ccc(C2(c3ccccc3)C=Cc3c4c(c5ccccc5c3O2)-c2c(cc(C(C)(C)c3ccccc3)c3c2COC3=O)C4(C)C)cc1]

(I-B)-(5) 10-(4-bromophenyl)-3-(4-methoxyphenyl)-12,14,14-trimethyl-9,11-dioxo-3-phenyl-3,9,11,14-tetrahydropyrrolo[3',4':4,5]indeno[2',3':3,4]naphtho[1,2-b]pyran

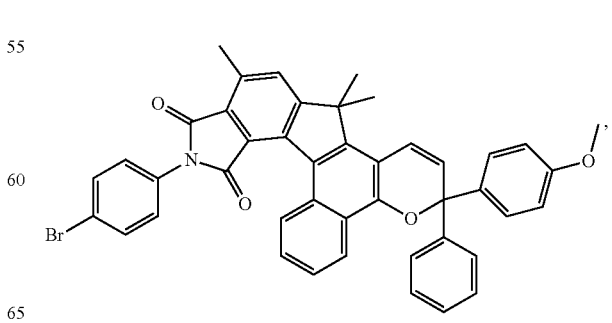

(I-B)-(6)  10-(4-bromophenyl)-3-(4-butoxyphenyl)-3-(4-methoxyphenyl)-12,14,14-trimethyl-9,11-dioxo-3-phenyl-3,9,11,14-tetrahydropyrrolo[3',4':4,5]indeno[2',3':3,4]naphtho[1,2-b]pyran

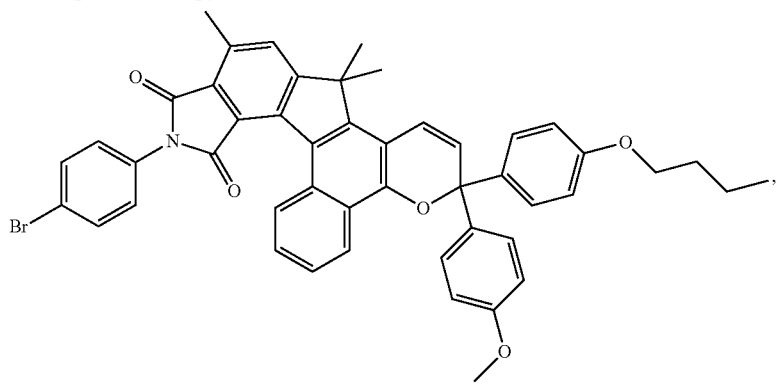 [SMILES: CCCCOc1ccc(C2(c3ccc(OC)cc3)C=Cc3c4c(c5ccccc5c3O2)-c2c(cc(C)c3c2C(=O)N(c2ccc(Br)cc2)C3=O)C4(C)C)cc1]

(I-B)-(7): 10-(4-bromophenyl)-3-(4-methoxyphenyl)-14,14-dimethyl-9,11-dioxo-3-phenyl-12-(2-(2-phenylpropan-2-yl))-3,9,11,14-tetrahydropyrrolo[3',4':4,5]indeno[2',3':3,4]naphtho[1,2-b]pyran

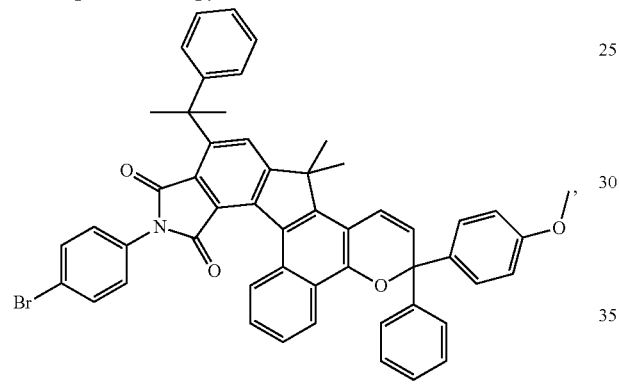

(I-B)-(8) 10-(4-bromophenyl)-9-hydroxy-3-(4-methoxyphenyl)-12,14,14-trimethyl-11-oxo-3-phenyl-3,9,11,14-tetrahydropyrrolo[3',4':4,5]indeno[2',3':3,4]naphtho[1,2-b]pyran

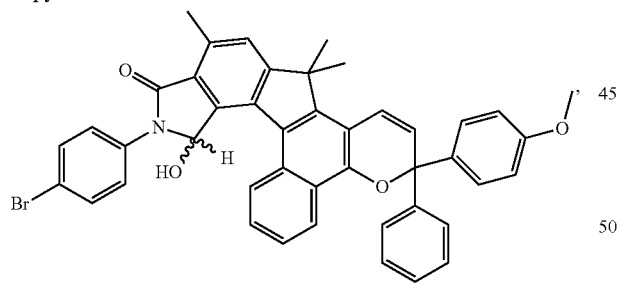

(I-B)-(9)  10-(4-bromophenyl)-3-(4-methoxyphenyl)-12,14,14-trimethyl-11-oxo-3-phenyl-3,9,11,14-tetrahydropyrrolo[3',4':4,5]indeno[2',3':3,4]naphtho[1,2-b]pyran

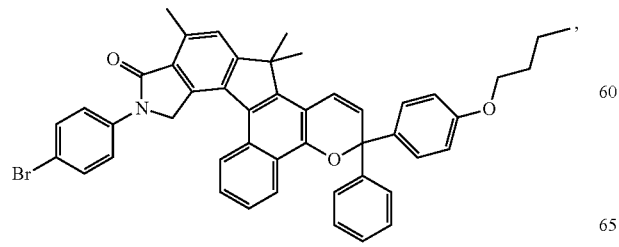

(I-B)-(10) 3-(4-methoxyphenyl)-10-(4'-(4-(trans-4-pentyl-cyclohexyl)benzamido)-[1,1'-biphenyl])-12,14,14-trimethyl-9,11-dioxo-3-phenyl-3,9,11,14-tetrahydropyrrolo[3',4':4,5]indeno[2',3':3,4]naphtho[1,2-b]pyran

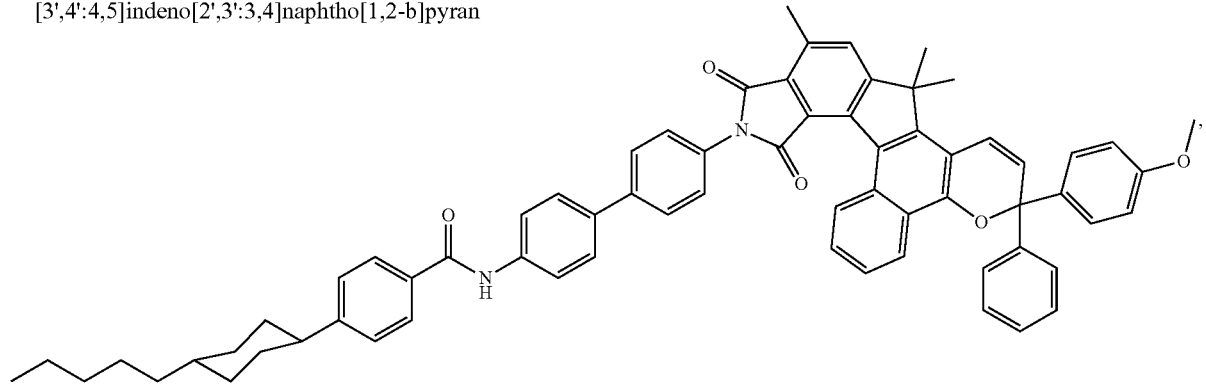

(I-B)-(11) 3-(4-butoxyphenyl)-9-hydroxy-3-(4-methoxyphenyl)-10-(4'-(4-(trans-4-pentylcyclohexyl)benzamido)-[1,1'-biphenyl])-12,14,14-trimethyl-11-oxo-3,9,11,14-tetrahydropyrrolo[3',4':4,5]indeno[2',3':3,4]naphtho[1,2-b]pyran

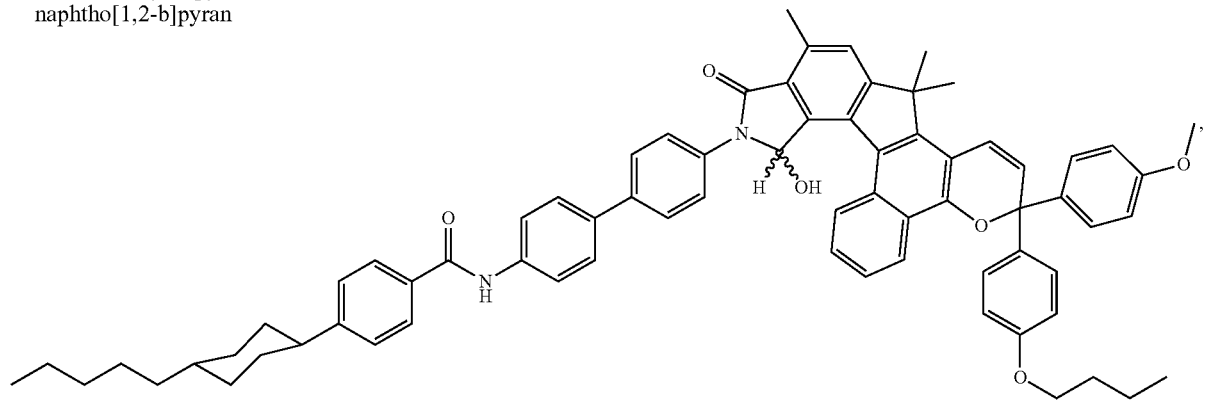

(I-B)-(12) 3-(4-methoxyphenyl)-10-(4'-(4-(trans-4-pentyl-cyclohexyl)benzamido)-[1,1'-biphenyl])-12-(2-(2-phenylpropan-2-yl))-14,14-dimethyl-9,11-dioxo-3-phenyl-3,9,11,14-tetrahydropyrrolo[3',4':4,5]indeno[2',3':3,4]naphtho[1,2-b]pyran

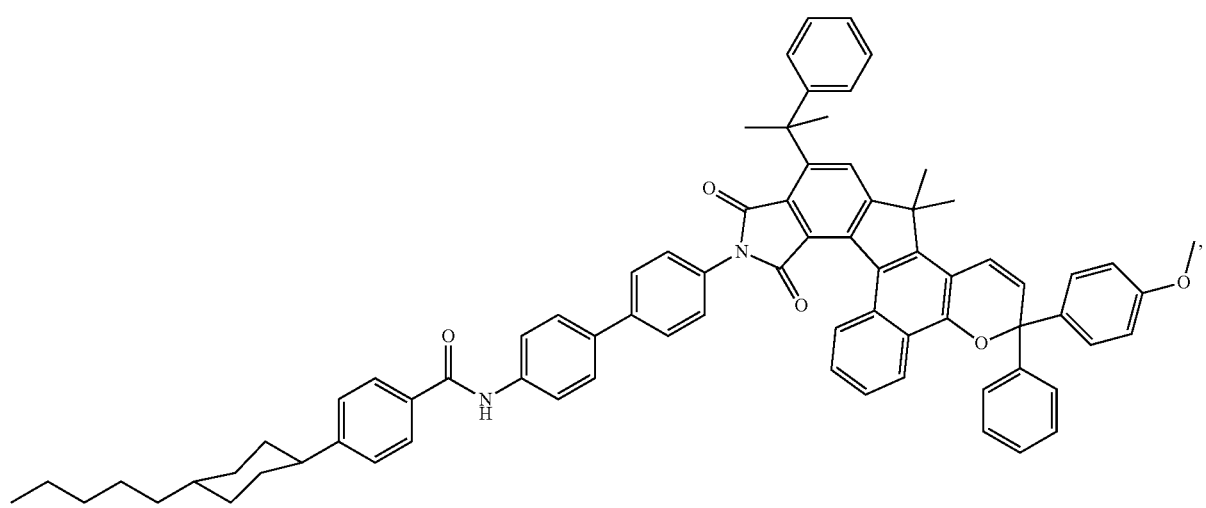 [SMILES: CCCCCC1CCC(c2ccc(C(=O)Nc3ccc(-c4ccc(N5C(=O)c6c(C(C)(C)c7ccccc7)cc7c(c6C5=O)-c5c(c6c(c8ccccc58)OC(c5ccccc5)(c5ccc(OC)cc5)C=C6)C7(C)C)cc4)cc3)cc2)CC1]

(I-B)-(13) 3-(4-butoxyphenyl)-3-(4-fluorophenyl)-6-methoxy-14,14-dimethyl-9,11-dioxo-3,9,11,14-tetrahydrofuro[3',4':4,5]indeno[2',3':3,4]naphtho[1,2-b]pyran

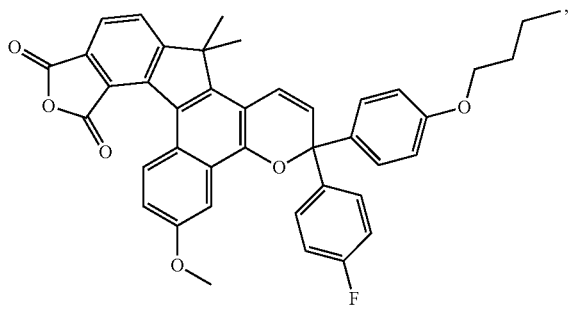 [SMILES: CCCCOc1ccc(C2(c3ccc(F)cc3)C=Cc3c4c(c5ccc(OC)cc5c3O2)-c2c(ccc3c2C(=O)OC3=O)C4(C)C)cc1]

(I-B)-(14): 3-(4-butoxyphenyl)-3-(4-fluorophenyl)-13,15,15-dimethyl-12-oxo-3,9,10,11,12,13,15-hexahydrobenzo[4,5]indeno[2',3':3,4]naphtho[1,2-b]pyran

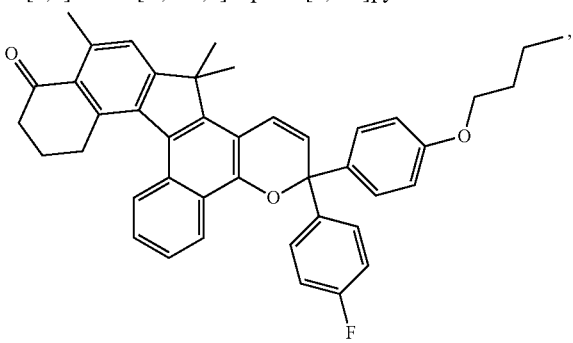

(I-B)-(15) 3-(4-butoxyphenyl)-3-(4-fluorophenyl)-15,17,17-trimethyl-9,14-dioxo-3,9,14,17-tetrahydro naphtho[2',3',4,5]indeno[2',3':3,4]naphtho[1,2-b]pyran

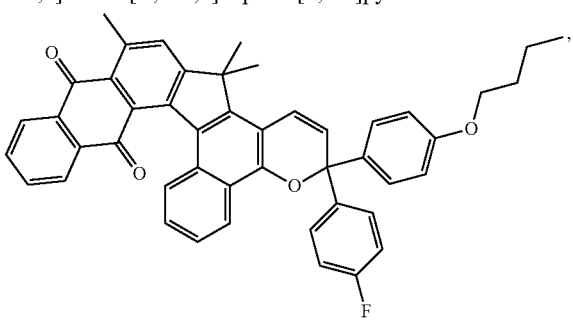

(I-B)-(16) 3-(4-butoxyphenyl)-3-(4-fluorophenyl)-13,15,15-dimethyl-9,12-dioxo-3,9,12,15-tetrahydrobenzo[4,5]indeno[2',3':3,4]naphtho[1,2-b]pyran

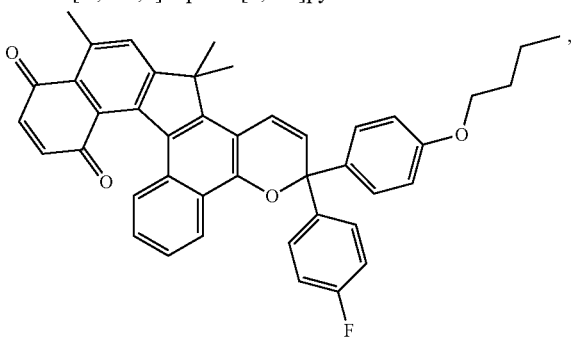

and (I-B)-(17) 3-(4-butoxyphenyl)-3-(4-fluorophenyl)-12-nitro-14-oxo-15,17,17-trimethyl-3,14,17-trihydrochromeno[2',3',4,5]indeno[2',3':3,4]naphtho[1,2-b]pyran

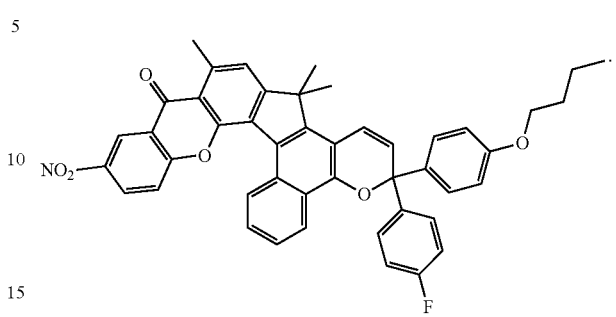

The present invention also relates to photochromic articles that include one or more photochromic compounds according to the present invention, such as represented by Formula (I-A) and Formula (I-B). The photochromic articles are, with some embodiments, prepared by art-recognized methods, such as by imbibition methods, cast-in-place methods, coating methods, in-mold coating methods, over-mold methods, and lamination methods.

With some embodiments, the photochromic articles are selected from ophthalmic articles, display articles, windows, mirrors, and active liquid crystal cell articles, and passive liquid crystal cell articles.

In accordance with some further embodiments, the photochromic articles of the present invention are selected from ophthalmic articles, and the ophthalmic articles are selected from corrective lenses, non-corrective lenses, contact lenses, intra-ocular lenses, magnifying lenses, protective lenses, and visors.

With some additional embodiments, the photochromic articles of the present invention are selected from display articles, and the display articles are selected from screens, monitors, and security elements.

With some embodiments, the photochromic indeno-fused ring pyran compounds of the present invention, such as represented by Formula (I-A), are prepared by reacting an intermediate compound represented by the following Formula (Int-1) with a propargyl alcohol represented by the following Formula (XI):

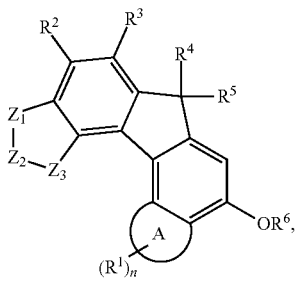

(Int-1)

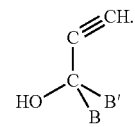

(XI)

With reference to Formula (Int-1), n, $R^1$-$R^5$, and $Z_1$-$Z_3$ are each as described herein with reference to Formula (I-A).

With further reference to Formula (Int-1), $R^6$ is selected from hydrogen, —C(O)—$R_{19}$ and —S(O)(O)$R_{19}$, wherein $R_{19}$ is selected from hydrocarbyl and halohydrocarbyl. With some embodiments, $R_{19}$ (of $R_6$) is selected from $C_1$-$C_{20}$ linear or branched alkyl and $C_1$-$C_{20}$ linear or branched perfluoroalkyl. With some further embodiments, $R_{19}$ (of $R_6$) is selected from $C_1$-$C_{10}$ linear or branched alkyl and $C_1$-$C_{10}$ linear or branched perfluoroalkyl. With reference to Formula (XI), B and B' are as described herein with reference to Formula (I-A).

With some embodiments, the photochromic indeno-fused ring pyran compounds of the present invention, such as represented by Formula (I-A), are formed by reacting or coupling the propargyl alcohol represented by Formula XI and the intermediated compound represented by Formula (Int-1), in the presence of a catalytic amount of a protonic acid, such as dodecyl benzene sulfonic acid (DBSA) or para-toluene sulfonic acid (pTSA), in a suitable solvent, such as a haloalkyl (e.g., trichloromethane), under an inert atmosphere (e.g., a nitrogen sweep), and at a temperature range of from 0° C. to the boiling point of the solvent, such as from 0° C. to 55° C., or from 10° C. to 45° C., or from 20° C. to 25° C.

With some embodiments, the photochromic indeno-fused ring pyran compound represented by Formula (I-B) is prepared by reacting an intermediate compound represented by the following Formula (Int-2) with the propargyl alcohol represented by Formula (XI):

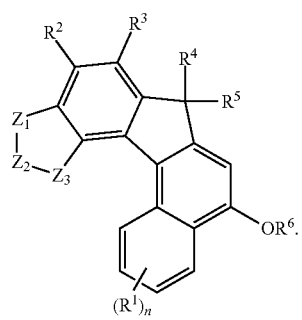

(Int-2)

With reference to Formula (Int-2), n is selected from 1-4, and $R^1$-$R^6$, and $Z_1$-$Z_3$ are as described herein with reference to Formulas (I-A), (I-B), and (Int-1).

With some more embodiments, the photochromic indeno-fused ring pyran compounds of the present invention, such as represented by Formula (I-A) and Formula (I-B), after formation thereof, can be subjected to one or more additional chemical reactions for purposes of modifying one or more of the groups thereof, such as the $R^1$, $R^2$, $R^3$, $R^4$, $R^5$, $Z_1$, $Z_2$, $Z_3$, B and/or B' groups. Examples of modified groups include, but are not limited to, lengthening groups. Examples of additional chemical reactions that the photochromic indeno-fused ring pyran compound represented by Formula (I-A) and Formula (I-B) can be subjected to include, but are not limited to, Friedel-Crafts reactions, palladium-catalyzed cross couplings, cyanation chemistries, etherifications, C—H bond activation chemistries, borylation chemistries, esterifications, amidations, condensations, oxidation chemistries and reduction chemistries. Non-limiting embodiments of the present invention, in which the photochromic indeno-fused ring pyran compound represented by Formula (I-A) and Formula (I-B) are subsequently modified are provided in Examples 5, 6, 7, 8, 9, and 10 further herein. In Examples 5, 6, and 7, reduction reactions were used to reduce carbonyl groups. In Examples 8 and 9 a Suzuki coupling reaction was used to build the lengthening group.

The intermediate compounds, that can be used to prepare the photochromic indeno-fused ring pyran compounds of the present invention, are themselves prepared, with some embodiments, by reacting together a dienophile and a lactone compound that includes a diene, in the presence of a catalyst (as will be described in further detail herein), and a carboxylic acid anhydride, when $R_6$ of Formulas (Int-1) and (Int-2) is —C(O)—$R_{19}$. For purposes of non-limiting illustration, the intermediate compounds, such as represented by Formula (Int-1), can be prepared in accordance with the general Scheme-(1) of FIG. 1. With reference to Scheme-1 of FIG. 1, the intermediate compound represented by Formula (Int-1), is prepared, with some embodiments, by reaction of a diene represented by the following Formula (II-A) with a lactone compound represented by the following Formula (III-A) in the presence of a catalyst, and a carboxylic acid anhydride represented by the following Formula (IV):

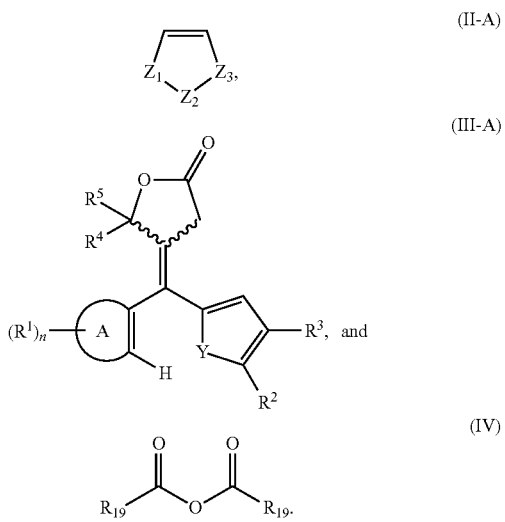

With reference to the above Formulas (II-A), (III-A), and (IV), Ring-A, $Z_1$, $Z_2$, $Z_3$, $R^1$-$R^5$, and $R_{19}$ are each as described herein with reference to Formulas (I-A) and (Int-1). The wavy bonds ( ∼∼∼∼ ) of Formula (III-A) indicate that the positions of the Ring-(A) and the five member ring (including Y, $R^2$ and $R^3$) can be switched relative to the double bond extending from the junction of the two wavy bonds, and as such, Formula (III-A) represents both structural isomers relative to the double bond. See, for example, Formula (III-A') and Formula (III-A") as follows.

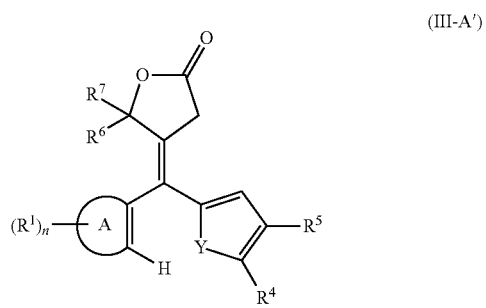

-continued

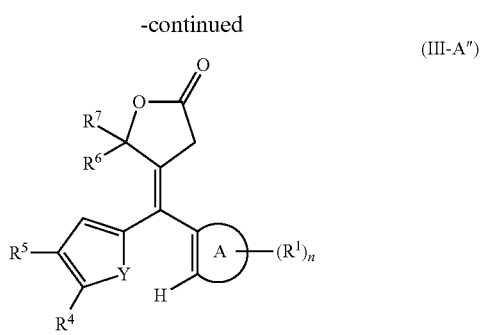

(III-A″)

With reference to Scheme-(1) of FIG. 1, Y of the lactone compound represented by Formula (III-A) is selected from O, S, and N($R_{18}$), where $R_{18}$ is selected from hydrogen, hydrocarbyl, and substituted hydrocarbyl. While not intending to be bound by any theory, it is believed that the dienophile represented by Formula (II-A) and the cyclic diene moiety (that includes Y, $R^2$ and $R^3$) of the lactone represented by Formula (III-A) react together by a Diels-Alder reaction.

With further reference to Scheme-(1) of FIG. 1, the group Y of the lactone compound, such as represented by Formula (III-A), is not present in or otherwise incorporated into the structure of the intermediate compound represented by Formula (Int-1). With some embodiments, during the course of the reaction represented by Scheme-1 of FIG. 1, Y of the lactone compounds, such as represented by Formula (III-A), forms: $H_2O$ (when Y is O); $SH_2$ (when Y is S); or $NH(R_{18})$ (when Y is $N(R_{18})$). While not intending to be bound by any theory, the conversion of Y of the lactone, such as represented by Formula (III-A), to $H_2O$, $SH_2$, or $NH(R_{18})$ is believed to occur during an aromatization step of the reaction.

Figure 2:
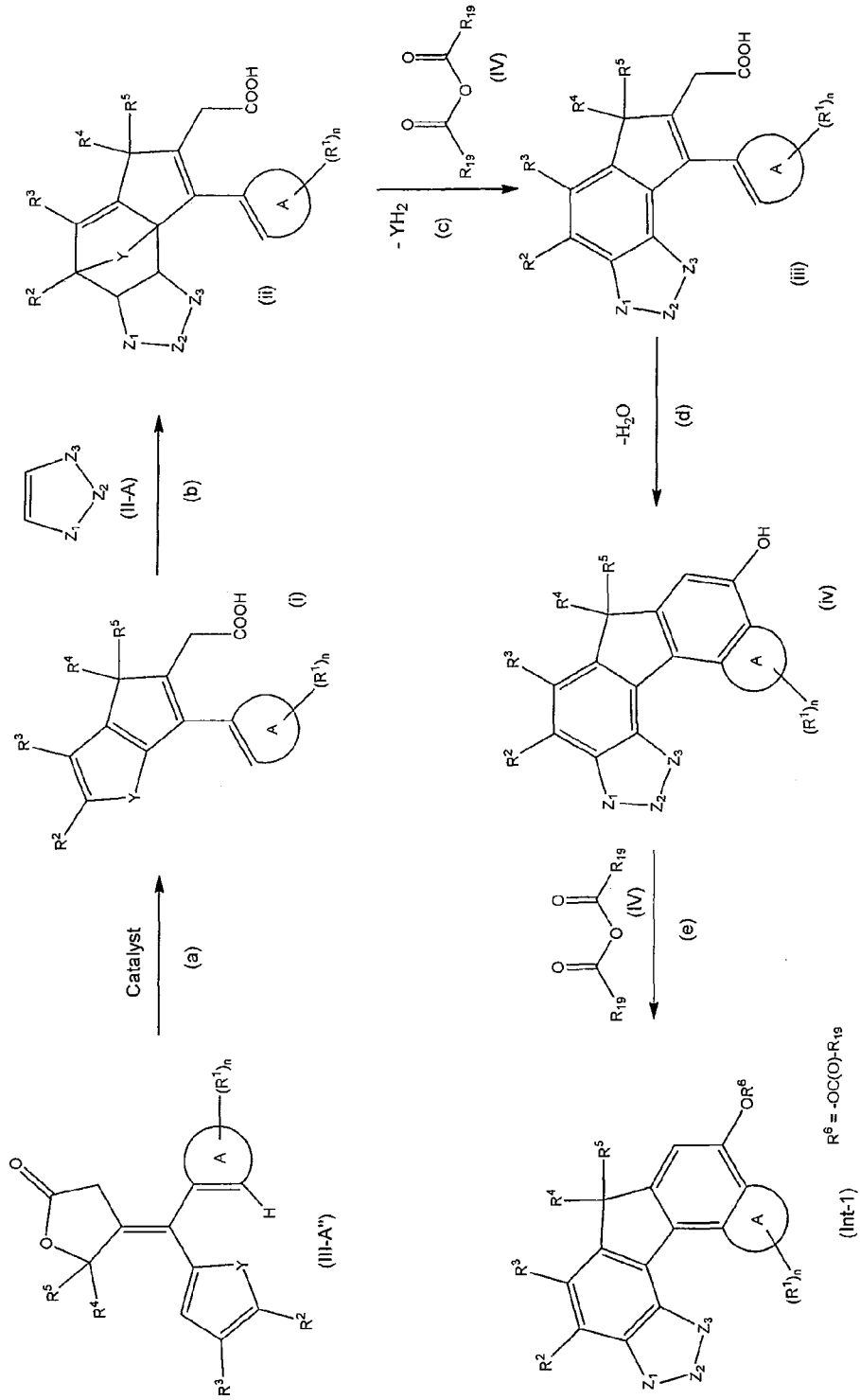
FIG. 2 is an illustrative representative scheme, Scheme-(2), of a method for preparing an intermediate compound from which the photochromic indeno-fused ring pyran compounds of the present invention can be prepared, with some embodiments.
Figure 3:
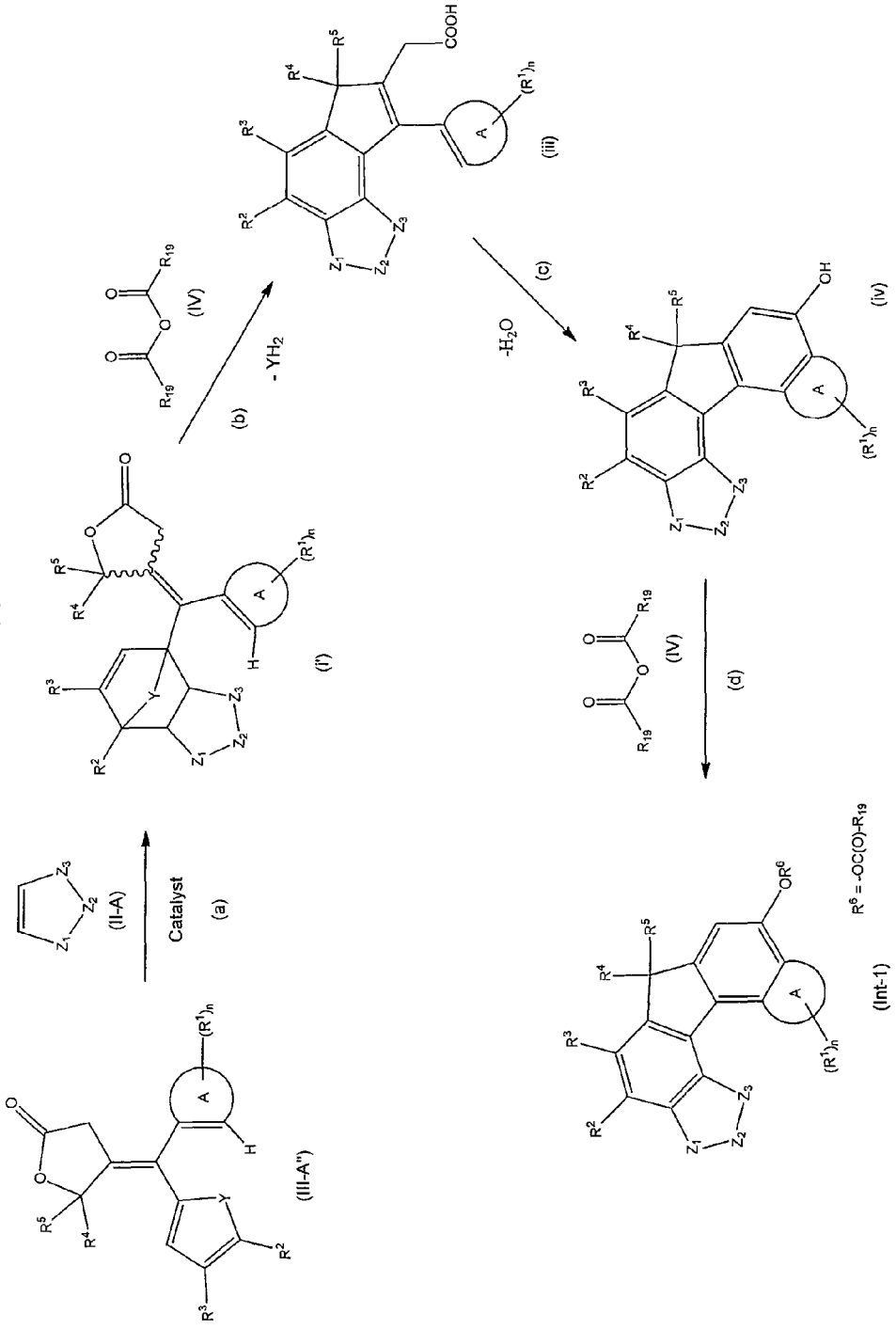
FIG. 3 is an illustrative representative scheme, Scheme-(3), of a method for preparing an intermediate compound from which the photochromic indeno-fused ring pyran compounds of the present invention can be prepared, with some embodiments.

While not intending to be bound by any theory and for purposes of non-limiting illustration, and based on the evidence presently at hand, the method by which the intermediate compounds are prepared, as represented by Scheme-1 of FIG. 1, and in accordance with some embodiments, is believed to proceed more particularly by one or both of the pathways as represented by the Scheme-(2) of FIG. 2 and/or Scheme-(3) of FIG. 3 of the drawings.

With reference to the pathway represented by Scheme-(2) of FIG. 2, in step (a), the lactone isomer represented by Formula (III-A″) is converted to Intermediate-(i) in the presence of a catalyst, as will be described in further detail herein. In Scheme-(2), the catalyst, the dienophile represented by Formula (II-A), and the carboxylic acid anhydride represented by Formula (IV) are together present with the lactone isomer represented by Formula (III-A″) at the beginning of the reaction, but are depicted as having a more prominent or direct role at different steps throughout the reaction scheme. In step (b), Intermediate-(i) and the dienophile represented by Formula (II-A) react together by what is believed to be a Diels-Alder reaction so as to form Intermediate-(ii). In step (c), which is an aromatization step, Intermediate-(ii) and the carboxylic acid anhydride represented by Formula (IV) together form Intermediate-(iii). During step (c), there is the concurrent formation of $YH_2$. In step (d) intermediate (iii) by intramolecular rearrangement is converted to intermediate (iv) with the loss of one molecule of $H_2O$. In step (e) Intermediate-(iv) and the carboxylic acid anhydride represented by Formula (IV) together form the intermediate compound represented by Formula (Int-1).

With reference to the pathway represented by Scheme-(3) of FIG. 3, in step (a) via a Diels-Alder reaction, the lactone isomer represented by Formula (III-A″) is converted to Intermediate-(i′) in the presence of the dienophile represented by Formula (II-A) and catalyst, as will be described in further detail herein. In Scheme-(3), the catalyst, the dienophile represented by Formula (II-A), and the carboxylic acid anhydride represented by Formula (IV) are together present with the lactone isomer represented by Formula (III-A′) at the beginning of the reaction, but are depicted as having a more prominent or direct role at different steps throughout the reaction scheme. In step (b), which is an aromatization step, Intermediate-(i′) together with the carboxylic acid anhydride represented by Formula (IV) is converted to Intermediate-(iii). During the course of step (b) of Scheme-(3) there is the concurrent formation of $YH_2$. In step (c), Intermediate (iii) by intramolecular rearrangement is converted to Intermediate (iv) with the loss of one molecule of $H_2O$. In step (d), Intermediate-(iv) and the carboxylic acid anhydride represented by Formula (IV) together form the intermediate compound represented by Formula (Int-1).

With further reference to Scheme-(2) of FIG. 2 and Scheme-(3) of FIG. 3, and without intending to be bound by any theory, it is believed that the structural isomer of the lactone compound represented by Formula (III-A′) also participates, though indirectly, in the illustrated reaction scheme by being converted to the structural isomer represented by Formula (III-A″). For purposes of illustration, and not intending to be bound by any theory, the lactone structural isomers represented by Formulas (III-A′) and (III-A″) are believed to rearrange from one to the other as represented by Scheme-4 of FIG. 4, in the presence of acid catalyst (which is not depicted in Scheme-4 of FIG. 4).

Figure 4:
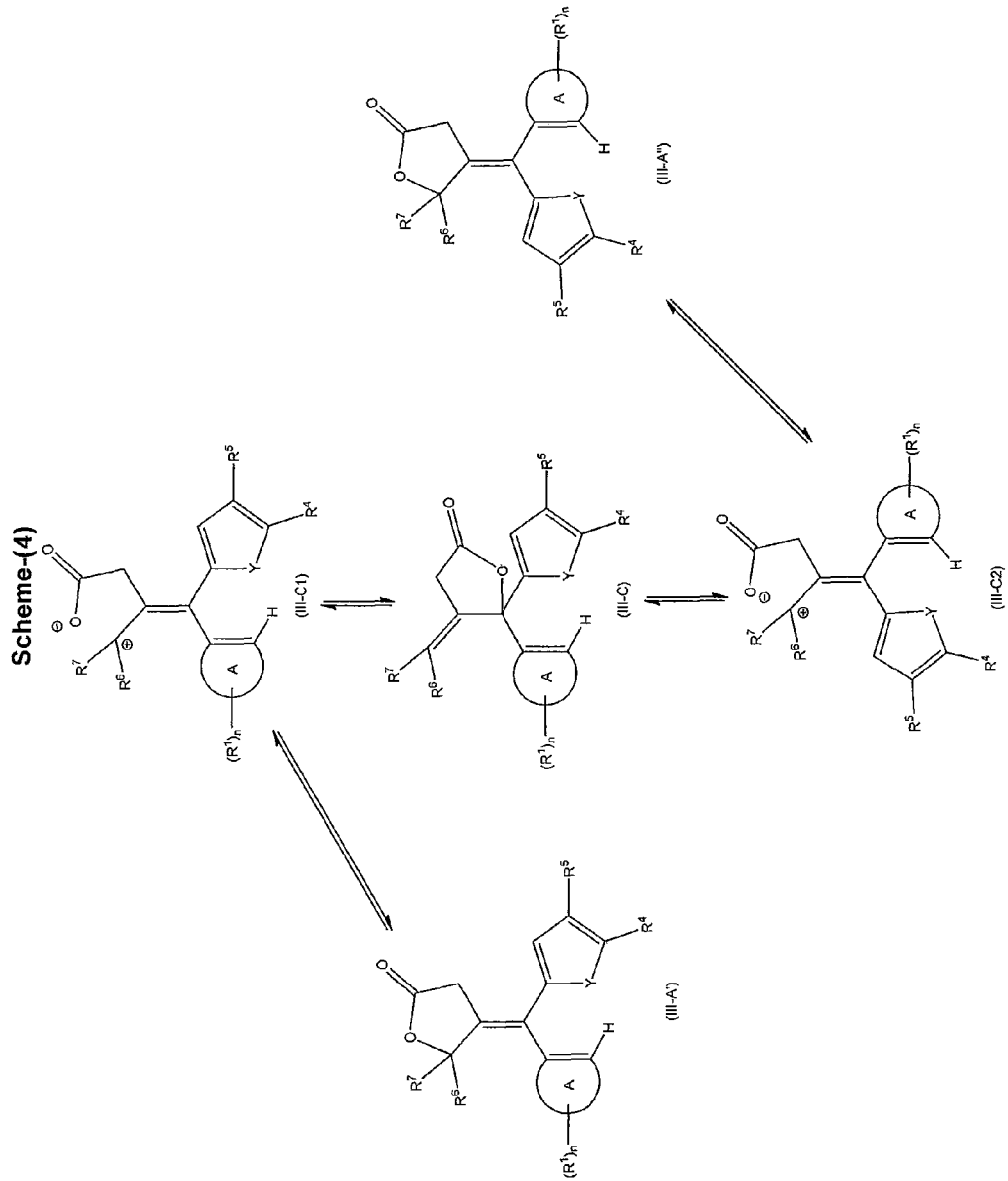
FIG. 4 is an illustrative representative scheme, Scheme-(4), of various equilibriums by which structural isomers of the lactone compounds represented by Formulas (III-A') and (III-A") are converted from one to the other, with some embodiments.

With reference to Scheme-4 of FIG. 4, the lactone compound represented by Formula (III-A′) is in equilibrium with the open-ringed ionic isomer represented by Formula (IIII-C1), which is in equilibrium with the spiro-lactone isomer represented by Formula (III-C), which is in equilibrium with the ring-opened ionic isomer represented by Formula (III-C2), which is in equilibrium with the lactone compound represented by Formula (III-A″). As such, by way of the structural isomers represented by Formulas (III-C1), (III-C), and (III-C2), the lactone structural isomers represented by Formulas (III-A′) and (III-A″) are converted from one to the other. As the lactone structural isomer represented by Formula (III-A″) is reacted/consumed in the reaction represented by Scheme-2 of FIG. 2 or Scheme-3 of FIG. 3, the lactone structural isomer represented by Formula (III-A′) is converted to the structural isomer represented by Formula (III-A″) as the effective equilibrium there-between is correspondingly shifted to replace the structural isomer represented by Formula (III-A″) as it is consumed in the reaction.

In accordance with some embodiments, the intermediate compounds, that can be used to prepare the photochromic indeno-fused ring pyran compounds of the present invention, are themselves prepared in the presence of a catalyst that is selected from at least one Lewis acid represented by the following Formula (V) and Formula (VI),

(V)

and

(VI)

Independently for each of Formula (V) and Formula (VI), M represents a metal, y is the valence of the metal, $R_{20}$ for each y is independently selected from hydrocarbyl and halohydrocarbyl, and X for each y is independently selected from halogen. More particularly, and with reference to the Lewis acid represented by Formula (VI), $X^-$ for each y is independently a halogen anion. More particularly, and independently for each of Formula (V) and Formula (VI), $M^{y+}$ represents a metal cation, and y is the valence of the metal cation.

With some further embodiments: the metal M of Formula (V) and Formula (VI) is in each case independently selected from Bi, B, Al, Hf, Sc, Cu, Yb, Ti, Sn, Fe, Zn, Ag, Y, In, Nb and Mg; $R_{20}$ of Formula (V) is selected from $C_1$-$C_{10}$ linear or branched alkyl, and $C_1$-$C_{10}$ linear or branched perfluoroalkyl; and X of Formula (VI) is selected from F, Cl, I, and Br.

In accordance with some additional embodiments, the catalyst is selected from one or more Lewis acids represented by Formula (V), in which M is Bi, y is 3, and $R_{20}$ is selected from $C_1$-$C_{10}$ linear or branched perfluoroalkyl, such as trifluoromethane.

The catalyst, with some embodiments, is present in an amount of at least 0.001 percent by moles, based on moles of the lactone compound represented by Formula (III-A), such as from 0.001 to 99 percent by moles, or from 0.01 to 30 percent by moles, in each case based on moles of the lactone compound represented by Formula (III-A).

The lactone compounds that can be used to prepare the intermediate compounds, such as represented by Formulas (Int-1) and (Int-2), are prepared by art-recognized procedures with some embodiments. For purposes of non-limiting illustration, and with reference to Scheme-5 of FIG. 5, the lactone compound represented by Formula (III-A) is prepared, in accordance with some embodiments, by reacting an acid ester represented by Formula (1) with a metal hydride reducing agent that is defined herein to include an organo metal hydride reducing agent, or a nucleophile represented by at least one of Formula (2) and/or Formula (3). The wavy bonds ( ∼∼∼ ) of Formula (1) indicate that the positions of the Ring-(A) and the five member ring (including Y, $R^2$ and $R^3$) can be switched relative to the double bond extending from the junction of the two wavy bonds, and as such, Formula (1) represents both structural isomers relative to the double bond.

Figure 5:
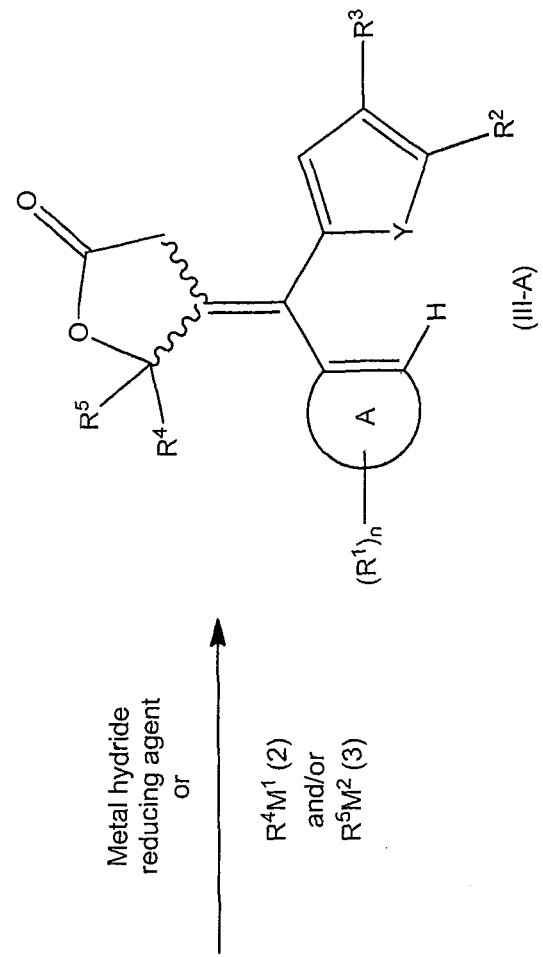
FIG. 5 is an illustrative representative scheme, Scheme-(5), of a method of preparing a lactone compound that is used, with some embodiments, to prepare an intermediate compound from which the photochromic indeno-fused ring pyran compounds of the present invention can be prepared, with some embodiments.
Figure 5:
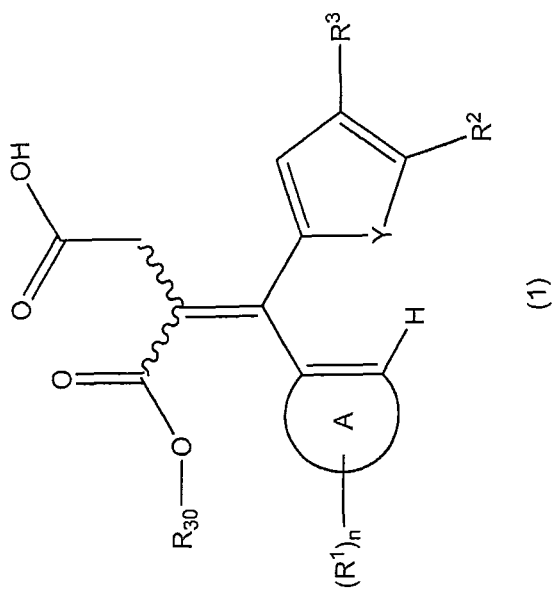

With further reference to Scheme-5 of FIG. 5, the metal hydride reducing agent is typically used when $R^4$ and $R^5$ are each hydrogen. The metal hydride reducing agent can, with some embodiments, be selected from sodium borohydride and lithium aluminum hydride, or an organo metal hydride reducing agent. The organo metal hydride reducing agent can be one or more di($C_1$-$C_{20}$ alkyl) aluminum hydride reducing agents, such as one or more di($C_1$-$C_6$ alkyl) aluminum hydride reducing agents, examples of which include, but are not limited to, diethyl aluminum hydride and diisobutyl aluminum hydride.

With reference to Formulas (2) and (3) of Scheme-5 of FIG. 5, $M^1$ and $M^2$ are each independently selected from Si($R^{31}$)$_3$, where each $R^{31}$ is independently selected from $C_1$-$C_8$ alkyl, or $M^1$ and $M^2$ each independently represent a counterion that includes a metal selected from Mg, Li, Mn, Cu, Zn, Al, Ti, Ln, and combinations thereof. With some embodiments, $R_{30}$ of the acid ester represented by Formula (1) is selected from hydrocarbyl and substituted hydrocarbyl. With some further embodiments, $R_{30}$ of the acid ester represented by Formula (1) is selected from linear or branched $C_1$-$C_{20}$ alkyl, such as linear or branched $C_1$-$C_6$ alkyl (such as ethyl, with some embodiments).

According to some embodiments, and with further reference to Scheme-5 of FIG. 5, $M^1$ and $M^2$ of Formulas (2) and (3) also include a halogen, and can be represented by $(M^1X)^+$ and $(M^2X)^+$, in which X is a halogen. Each of $M^1$ and $M^2$ of Formulas (2) and (3) can each be selected from $(MgX)^+$, in which X is selected from halogen, such as Cl, Br and I, examples of which include, but are not limited to, $(MgCl)^+$, $(MgBr)^+$ and $(MgI)^+$.

With some embodiments, the nucleophiles represented by Formulas (2) and (3) of Scheme-5 of FIG. 5, are each Grignard reagents, and the reaction represented by Scheme-5 is a Grignard reaction, which is conducted under Grignard reaction conditions. The reaction represented by Scheme-5 is typically conducted in the presence of an appropriate solvent, such as tetrahydrofuran (THF), and under conditions of ambient pressure (e.g., approximately 1 atm), under an inert atmosphere (e.g., under a nitrogen sweep), such as from −30° C. to 60° C., or from −20° C. to 45° C., or from −10° C. to 30° C., and optionally with reflux.

The reaction of the acid ester represented by Formula (1) with the nucleophile represented by Formulas (2) and/or (3), of Scheme-5, is with some embodiments, conducted in the presence of metal salts. Examples of metal salts that can be present include, but are not limited to, aluminum chloride ($AlCl_3$), tin chloride, zinc chloride, bismuth triflate, alkali metal halides, anhydrous alkaline metal halides, rate earth metal salts, e.g., lanthanide halides, such as lanthanum III chloride, and lanthanide triflate, and combinations thereof. Examples of alkali metal halides that can be present include, but are not limited to, sodium halides and/or potassium halides, such as sodium chloride (NaCl) and/or potassium chloride (KCl). Examples of alkaline metal halides that can be present include, but are not limited to, anhydrous calcium halides, anhydrous lithium halides and/or anhydrous magnesium halides, such as calcium chloride, lithium chloride and magnesium chloride. The metal salt is typically present in an amount of from 0.1 molar percent to 600 molar percent, or from 1.0 to 100 molar percent, or from 10 to 50 molar percent, based on 100 molar percent of the starting materials. The molar percent is defined herein as the percentage of the number of moles of the metal salt per liter of solute based on the total moles per liter of solute of the acid ester represented by Formula (1) and the nucleophiles represented by Formulas (2) and (3) in Scheme-5.

In accordance with some embodiments, the lactone compounds represented by Formula (III-A) (including Formulas (III-A') and (III-A")), after formation thereof, can be subjected to one or more additional chemical reactions for purposes of modifying one or more of the groups thereof, such as the $R^1$, $R^4$, $R^5$, $R^6$, and/or $R^7$ groups. Examples of modified groups include, but are not limited to, lengthening groups, such as group L (or L groups) as described previously herein with reference to Formula (II). With some embodiments, the groups of the lactone compounds represented by Formula (III-A) are subsequently modified because the modified groups would not survive formation of the lactone itself. Examples of additional chemical reactions that the lactone compounds represented by Formula (III-A) can be subjected to include, but are not limited to, Friedel-Crafts reactions, palladium-catalyzed cross couplings, cyanation chemistries, etherifications, C—H bond activation chemistries, borylation chemistries, esterifications, amidations, oxidation chemistries, and reduction chemistries. For purposes of non-limiting illustration, the modification of lactone compounds represented by Formula (III-A) is shown in Examples 3 and 4 further herein, in which the starting lactones were converted in-situ to modified lactones having new substituents, such as but not limited to, 9-(2-phenylpropan-2-yl), before other reactions were undertaken.

The acid ester represented by Formula (1) of Scheme-5 can be prepared in accordance with art-recognized methods. With some embodiments, the acid ester represented by Formula (1) is prepared by a reaction between a ketone represented by Formula (4) and a succinic acid diester represented by Formula (5), as represented by Scheme-6 of FIG. 6.

Figure 6:
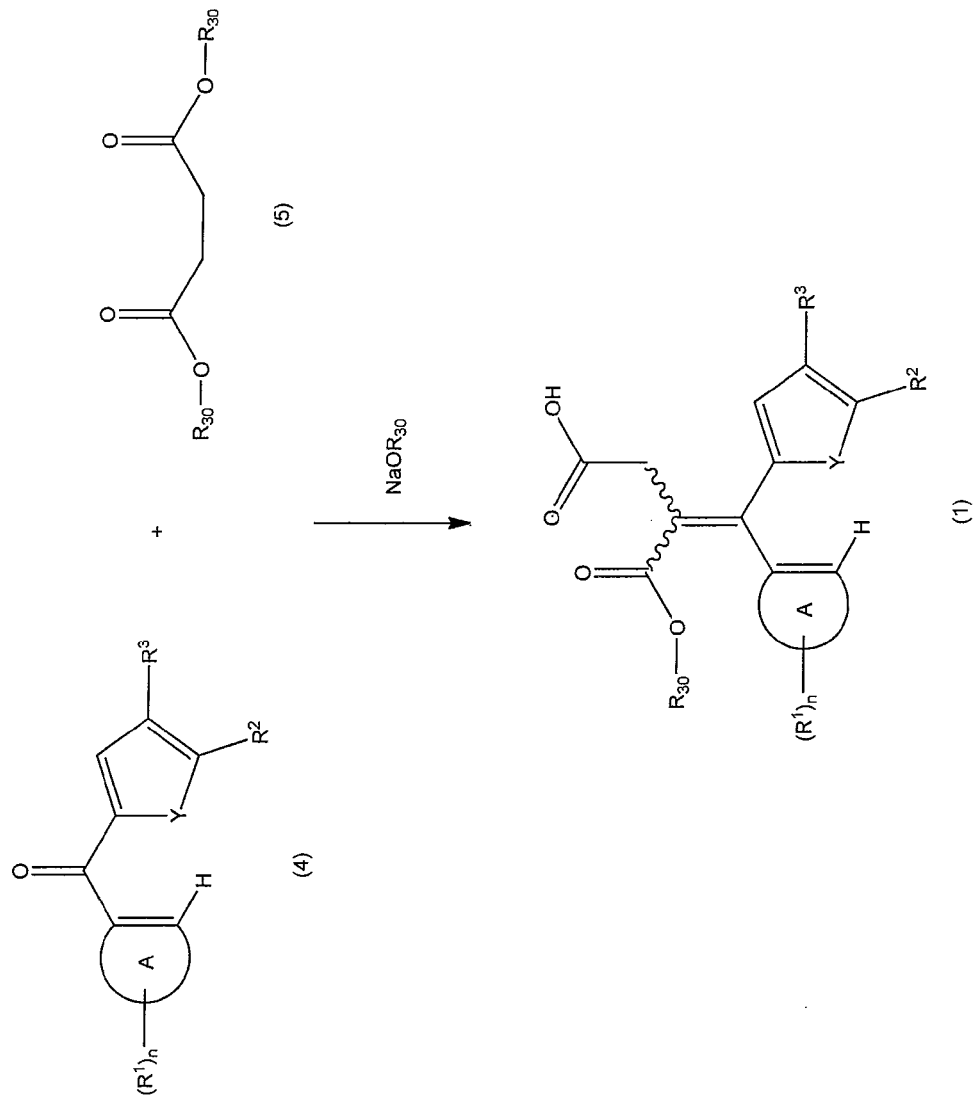
FIG. 6 is an illustrative representative scheme, Scheme-(6), of a method of preparing an acid ester precursor of the lactone compound depicted in Scheme-(5).

With reference to Scheme-6 of FIG. 6, the ketone represented by Formula (4) is reacted with a succinic acid diester represented by Formula (5), in which each $R_{30}$ is as described previously herein (e.g., each $R_{30}$ can be ethyl), in the presence of a strong base, such as an alkali metal alkoxide, such as $NaOR_{30}$ (e.g., sodium ethoxide). The reaction of Scheme-6 is conducted under appropriate conditions, such as under reflux at a temperature of the boiling point of the solvent, under an inert atmosphere, and in the presence of an appropriate solvent, such as tetrahydrofuran or toluene. Workup of the reaction represented by Scheme-6 is conducted, with some embodiments, in accordance with art-recognized procedures.

With further reference to Schemes-(5) and (6) of FIGS. 5 and 6, Ring-A, n, $R^1$-$R^5$, and Y, are each as described herein with reference to Formulas (I-A) and (III-A).

As previously discussed herein, B and B' of the photochromic compounds of the present invention can, with some embodiments, each independently be an aryl group that is mono-substituted with a reactive substitutent or a compatibilizing substituent. If the photochromic compounds of the present invention include multiple reactive substituents and/or multiple compatiblizing substituents, each reactive substituent and each compatiblizing substituent can be independently chosen.

The reactive substituent and the compatibilizing substituent are each independently represented, with some embodiments, in each case by one of the following representative formulas:

-A'-D-E-G-J   (XX);

-A'-D-J   (XXI);

-A'-G-J   (XXII);

-G-E-G-J   (XXIII);

-D-G-J   (XXIV);

-G-J   (XXV);

-D-E-G-J   (XXVI);

-D-J   (XXVII);

and

-A'-J   (XXVIII).

With reference to formulas (XX) through (XXVIII), non-limiting examples of groups that -A'- can represent according to various non-limiting embodiments disclosed herein include —O—, —C(=O)—, —CH$_2$—, —OC(=O)— and —NHC(=O)—, provided that if -A'-represents —O—, -A'- forms at least one bond with -J.

Non-limiting examples of groups that -D- can represent according to various non-limiting embodiments include a diamine residue or a derivative thereof, wherein a first amino nitrogen of the diamine residue can form a bond with -A'-, or a substituent or an available position on the photochromic indeno-fused ring pyran compound, and a second amino nitrogen of the diamine residue can form a bond with -E-, -G- or -J; and an amino alcohol residue or a derivative thereof, wherein an amino nitrogen of the amino alcohol residue can form a bond with -A'-, or a substituent or an available position on the photochromic indeno-fused ring pyran compound, and an alcohol oxygen of the amino alcohol residue can form a bond with -E-, -G- or -J. Alternatively, according to various non-limiting embodiments, the amino nitrogen of the amino alcohol residue can form a bond with -E-, -G- or -J, and the alcohol oxygen of the amino alcohol residue can form a bond with -A'-, or a substituent or an available position on the photochromic indeno-fused ring pyran compound.

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. More particular, illustrative and non-limiting examples of diamine residues that can be used in conjunction with various non-limiting embodiments of the present invention include the following:

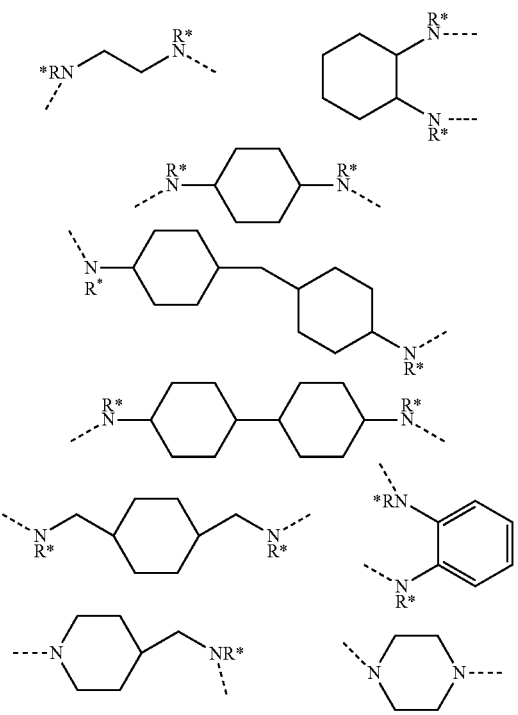

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. More particular, illustrative and non-limiting examples of amino alcohol residues that can be used in conjunction with various non-limiting embodiments present invention include the following:

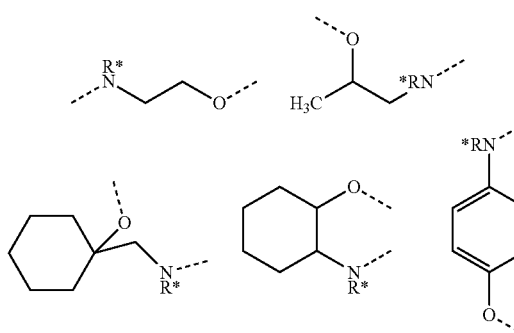

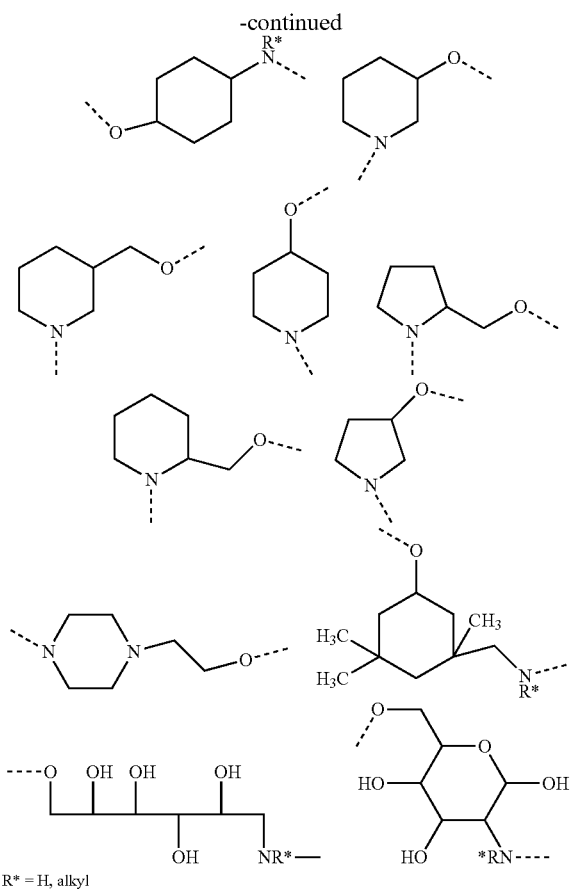

R* = H, alkyl

With continued reference to formulas (XX) through (XX-VIII) above, according to various non-limiting embodiments, -E- can represent a dicarboxylic acid residue or a derivative thereof, wherein a first carbonyl group of said dicarboxylic acid residue can form a bond with -G- or -D-, and a second carbonyl group of the dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. More particular, illustrative and non-limiting examples of dicarboxylic acid residues that can be used in conjunction with various non-limiting embodiments of the present invention include the following:

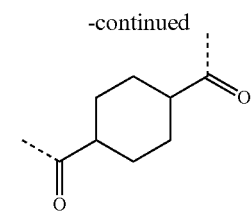

According to various non-limiting embodiments of the present invention, -G- can represent a group represented by the following general formula, -[(OC$_2$H$_4$)$_x$(OC$_3$H$_6$)$_y$(OC$_4$H$_8$)$_z$]-O- in which x, y and z are each independently chosen and range from 0 to 50, and a sum of x, y, and z ranges from 1 to 50; a polyol residue or a derivative thereof, wherein a first polyol oxygen of the polyol residue can form a bond with -A'-, -D-, -E-, or a substituent or an available position on the photochromic indeno-fused pyran compound, and a second polyol oxygen of the polyol can form a bond with -E- or -J; or a combination thereof, wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$(OC$_4$H$_8$)$_z$]-O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particular, illustrative and non-limiting examples of polyols from which the polyol residues that -G- can represent can be formed, according to various non-limiting embodiments, include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XX) through (XX-VIII), according to various non-limiting embodiments, -J can represent a group —K, wherein —K represents a group such as, but not limited to, —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H, and —SO$_3$H, wherein subscript "w" ranges from 1 to 18. According to other non-limiting embodiments, -J can represent hydrogen that forms a bond with an oxygen or a nitrogen of linking group to form a reactive moiety such as —OH or —NH. For example, according to various non-limiting embodiments, -J can represent hydrogen, provided that if -J represents hydrogen, -J is bonded to an oxygen of -D- or -G-, or a nitrogen of -D-.

According to still further non-limiting embodiments, -J can represent a group -L' or residue thereof, wherein -L' can represent a reactive moiety. For example, according to various non-limiting embodiments disclosed herein -L' can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

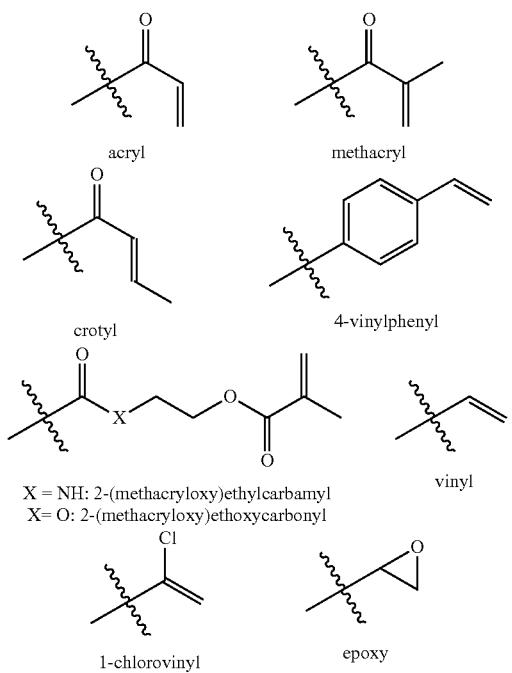

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by q-(OH)$_a$ and the residue of the polyol can be represented by the formula —O-q-(OH)$_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J can be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J can be produced by acidic condensation of one or more of the polyol hydroxyl groups with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. Further, although not limiting herein, if -G- represents a polyol residue and -J represents a group -L' chosen from acryl, methacryl, 2-(methacryloxy)ethylcarbamyl and epoxy, -L' can be added by condensation of the polyol residue with acryloyl chloride, methacryloyl chloride, 2-isocyanatoethyl methacrylate or epichlorohydrin, respectively.

The present invention is more particularly described in the following examples, which are intended as illustrative only, since numerous modifications and variations therein will be apparent to those skilled in the art.

EXAMPLES

Part 1 describes the preparation of indeno-fused ring pyran compounds in Examples 1-11. Part 2 describes the testing of some of the photochromic properties of the indeno-fused ring pyran compounds. Part 3 describes the testing of the dichroic properties of some of the indeno-fused ring pyran compounds.

Part 1

Preparation of Examples 1-11

In the following examples, the synthetic procedures for preparing naphthopyran compounds according to the present invention are described.

Example 1

Step 1

Into a flask containing benzoyl chloride (206 g) and dichloromethane (2 L) was added aluminum chloride (200 g) while stirring. After 30 minutes at ambient temperature the flask was placed in a water bath and a condenser was connected through which 2-methylfuran (210 mL) was added dropwise over 30 minutes. The resulting mixture was stirred for 7 hours then carefully poured into cold water (3 L). The organic layer was collected, washed with water and concentrated to afford (5-methylfuran-2-yl)(phenyl)methanone as an oily product (220 g).

Step 2

The product of Step 1 (220 g), dimethyl succinate (242 mL) and toluene (2.5 L) were added to a reaction flask equipped with a mechanical stirrer, a solid addition funnel and a Nitrogen blanket. Potassium t-butoxide (176 g) was added through the solid addition funnel and the mixture was stirred at room temperature for 3 hours. The resulting mixture was poured into water (2 L) and the aqueous layer was collected. The toluene layer was extracted with 200 ml water. The aqueous layers were combined and washed with toluene. Aqueous HCl (3N) was added to the water solution to adjust the pH to 5. The resulting solution was extracted with ethyl acetate. The ethyl acetate layer was then washed with brine (500 mL) and concentrated. The residue was then purified through a silica gel plug eluting with a mixture of 1/1 toluene/ethyl acetate, collecting the fractions containing the product. After evaporation of the solvents, a dense oily material was obtained (203 g).

Step 3

Anhydrous lanthanum (III) chloride (91 g) was ground to very fine powder then mixed with lithium chloride (47 g) and dry THF (1.5 L) in a 5 L three-neck flask equipped with a mechanical stirrer and an addition funnel. The mixture was refluxed until completely dissolved. The product from Step 2 (54 g) was dissolved in the mixture, then cooled to −5° C. A solution of 3 M methyl magnesium chloride in dry THF (375 mL) was placed in the addition funnel. The first 100 mL of the Grignard was added to the mixture slowly, observing gas bubbles and an exotherm. After reducing the temperature back to −5° C., the remainder of the Grignard was added over 3 minutes. After stirring 30 minutes at −5° C., the ice bath was removed and the mixture was stirred at room temperature for one hour. The reaction mixture was then poured into a flask containing cold water (350 mL) and the pH adjusted to 4 using 12 M HCl (25 mL). The water layer was discarded and the organic layer was washed twice with brine and concentrated to dry. The resulting solid was re-dissolved in toluene and purified through a silica gel plug eluting with toluene. The clear solution was concentrated to dryness to obtain a dark oily product (41 g). $^1$H NMR showed that the product had a structure consistent with ~1/1 mixture of E/Z isomers of beta-((5-methylfuran-2-yl)(phenyl)methylene)-gamma, gamma-dimethyl-gamma-butyrolactone.

Step 4

The product from step 3 (5 g) and N-(4-bromophenyl) maleimide (5 g) were dissolved in acetic anhydride (50 mL) followed by addition of bismuth triflate (0.8 g). The reaction mixture was heated at 70° C. for 3 hours. The solvent was then removed by evaporation, and the resulting residue re-dissolved in dichloromethane and washed with water (100 mL). The organic layer was collected and purified through a silica gel plug eluting with a mixture of 5/1 hexanes/ethyl acetate, collecting the fractions containing the product. Removal of solvent yielded a solid product (9 g). $^1$H NMR showed that the product had a structure consistent with 11-(4-bromophenyl)-10,12-dioxo-7,7,9-trimethyl-7,10,11,12-tetrahydropyrrolo[3',4':4,5]indeno[3,2-a]naphthalen-5-yl acetate.

Step 5

The product from Step 4 (3 g) was dissolved in ethanol (70 mL) and 12 M HCl (aq, 0.2 mL) was added. The mixture was refluxed for 1 hour then cooled to ambient temperature. The solvent was removed by evaporation. The resulting residue was dissolved in dichloromethane (100 mL), washed once with water (100 mL) and concentrated to dryness to yield a solid product (2.6 g). $^1$H NMR showed that the product had a structure consistent with 11-(4-bromophenyl)-10,12-dioxo-7,7,9-trimethyl-7,10,11,12-tetrahydropyrrolo[3',4':4,5]indeno[3,2-a]naphthalene-5-ol. This procedure was repeated to produce enough product for the next step.

Step 6

The product from Step 5 (3 g) was dissolved in 1,2-dichloroethane (150 mL). To the flask was added 1-(4-butoxyphenyl)-1-phenylprop-2-yn-1-ol (2 g) and a few crystals of p-toluenesulfonic acid. The mixture was stirred at room temperature for three hours. The reaction mixture was washed once with water (50 mL) and the organic residue was purified by silica gel chromatography eluting with 4/1 hexanes/ethyl acetate, collecting the fractions containing the product. After evaporation of the solvents, the product was further purified using a CombiFlash® Rf from Teledyne ISCO, yielding yellow crystals (0.9 g). $^1$H NMR analysis indicated that the product had a structure consistent with 10-(4-bromophenyl)-3-(4-butoxyphenyl)-12,14,14-trimethyl-9,11-dioxo-3-phenyl-3,9,11,14-tetrahydropyrrolo[3',4':4,5]indeno[2',3':3,4] naphtho[1,2-b]pyran.

Example 2

The procedure from Example 1 was followed except that 1-(4-butoxyphenyl)-1-(4-methoxyphenyl)prop-2-yn-1-ol was used in place of 1-(4-butoxyphenyl)-1-phenylprop-2-yn-1-ol in Step 6, yielding a yellow solid. $^1$H NMR analysis indicated that the product had a structure consistent with 10-(4-bromophenyl)-3-(4-butoxyphenyl)-3-(4-methoxyphenyl)-12,14,14-trimethyl-9,11-dioxo-3-phenyl-3,9,11,14-tetrahydropyrrolo[3',4':4,5]indeno[2',3':3,4]naphtho[1,2-b]pyran.

Example 3

Step 1

To a stirred mixture of benzoyl chloride (120 g), furan (100 mL) and dichloromethane (1 L) at 0° C. was added aluminum chloride (130 g) over one hour. The mixture was stirred at room temperature for two hours then poured slowly into water (1 L). The mixture was passed through Celite to remove the resulting brown precipitate. The organic layer was collected and concentrated. The crude product was purified by silica gel chromatography eluting with 2/8 ethyl acetate/hexane to yield a viscous oil (50 g). $^1$H NMR showed that the product had a structure consistent with furan-2-yl(phenyl)methanone.

Step 2

The product of Step 1 (50 g), dimethyl succinic ester (70 g) and toluene (1000 mL) were placed in a three-neck 3 L flask equipped with a mechanical stirrer. Potassium t-butoxide (42 g) was added in batches over a 30 minute period. An exothermic reaction was observed along with the formation of a large amount of precipitate. After a one hour hold, water (1000 mL) was added and the mixture transferred to a separatory funnel. The aqueous phase was collected and washed twice with toluene (200 mL). The pH was adjusted to ~2 using 3N HCl, resulting in the separation of a large amount of oil. To the mixture was added ethyl acetate (500 mL). After stirring at ambient temperature for 10 minutes, the organic layer was collected, washed with brine and dried over MgSO$_4$. After concentration, the crude product was purified through a silica gel plug with the use of a gradient of 10/90 to 60/40 ethyl acetate/hexane as the eluent. A viscous oil (58 g) was obtained. ¹H NMR showed that the obtained product had a structure consistent with ~1/1 Z/E mixture of 4-(furan-2-yl)-3-(methoxycarbonyl)-4-phenyl-but-3-enoic acid.

Step 3

A stock solution was prepared by mixing anhydrous lanthanum (III) chloride powder (147 g) and lithium chloride (76.2 g) in dry THF (2 L) and stirring for 3 days. The product of Step 2 (20 g) was dissolved in the stock solution (500 mL) and cooled to 0° C. A solution of 3M methyl magnesium chloride in THF (116 mL) was placed in the addition funnel. The first 30% of the Grignard was added slowly to the mixture, during which an exotherm was observed. Upon restoring the temperature to 0° C., the remainder of the Grignard was added over one minute. After stirring one hour at 0° C. and an additional hour at room temperature, the mixture was poured into ice water (0.5 L), and the pH adjusted to ~3 using 12N HCl (~70 ml). The mixture turned clear with formation of two layers. The aqueous layer was discarded. The recovered organic layer was washed with brine three times and then concentrated to dry. The crude product was purified through a silica gel plug with the use of toluene as eluent to yield a viscous oil (15 g). ¹H NMR showed that the product had a structure consistent with a mixture of ~1/1 E/Z isomers of beta-((phenyl)(furan-2-yl)methylene)-gamma,gamma-dimethyl-gamma-butyrolactone.

Step 4

To a solution of N-(4-bromophenyl)maleimide (2.5 g) in acetic anhydride (20 ml) was added the product from Step 3 (3 g), 2-phenylpropan-2-ol (2 g) and bismuth triflate (0.3 g). The mixture was stirred at room temperature for 72 hours followed by removal of solvent. The residue was dissolved in ethanol (70 mL) and 12 M HCl (aq, 0.2 mL) was added. The mixture was refluxed for one hour, cooled to ambient temperature and the solvent was removed. The residue was purified by column separation using a CombiFlash Rf to yield a viscous yellow oil (5 g). ¹H NMR showed that the product had a structure consistent with 11-(4-bromophenyl)-10,12-dioxo-7,7-dimethyl-9-(2-phenylpropan-2-yl)-7,10,11,12-tetrahydropyrrolo[3',4':4,5]indeno[3,2-a]naphthalen-5-ol.

Step 5

The procedure from Step 6 of Example 1 was used except that the product from Step 4 of this Example was used in place of the product from Step 5 of Example 1 and 1-(4-methoxyphenyl)-1-phenylprop-2-yn-1-ol was used in place of 1-(4-butoxyphenyl)-1-phenylprop-2-yn-1-ol. ¹H NMR analysis showed the product had a structure consistent with 10-(4-bromophenyl)-3-(4-methoxyphenyl)-14,14-dimethyl-9,11-dioxo-3-phenyl-12-(2-phenylpropan-2-yl)-3,9,11,14-tetrahydropyrrolo[3',4':4,5]indeno[2',3':3,4]naphtho[1,2-b]pyran.

Example 4

The procedures from Example 3 were followed except that maleic anhydride was used in place of N-(4-bromophenyl) maleimide in Step 4. ¹H NMR analysis showed the product had a structure consistent with 3-(4-methoxyphenyl)-14,14-dimethyl-9,11-dioxo-3-phenyl-12-(2-(2-phenylpropan-2-yl))-3,9,11,14-tetrahydrofuro[3',4':4,5]indeno[2',3':3,4]naphtho[1,2-b]pyran.

Example 5

The product from Example 4 (0.7 g) was dissolved in dry THF (40 mL). A THF solution of lithium aluminum hydride (2 M, 0.4 ml) was added slowly into the mixture. Two minutes after the addition was complete, the reaction mixture was poured into saturated aqueous ammonium chloride (20 mL) and extracted with ethyl acetate. The organic phase was recovered and the solvent was evaporated. The residue was purified by silica gel chromatography eluting with 5/1 hexanes/ethyl acetate. A yellow solid (0.5 g) was obtained. ¹H NMR analysis indicated that the product had a structure consistent with 3-(4-methoxyphenyl)-14,14-dimethyl-11-oxo-3-phenyl-12-(2-(2-phenylpropan-2-yl))-3,9,11,14-tetrahydrofuro[3',4':4,5]indeno[2',3':3,4]naphtho[1,2-b]pyran.

Example 6

The product from Example 1 (0.8 g) was dissolved in dry THF (25 mL). A THF solution of Lithium aluminum hydride (2 M, 0.7 ml) was added at ambient temperature. Five minutes after the addition was complete, the reaction mixture was poured into a flask containing 10% HCl (10 ml), then extracted with ethyl acetate (100 mL). The organic layer was washed once with brine (50 mL) then concentrated. The residue was purified by silica gel chromatography eluting with 10/1 hexanes/ethyl acetate to yield a solid product (0.2 g). ¹H NMR analysis indicated that the product had a structure consistent with 10-(4-bromophenyl)-3-(4-butxyphenyl)-12,14,14-trimethyl-11-oxo-3-phenyl-3,9,11,14-tetrahydropyrrolo[3',4':4,5]indeno[2',3':3,4]naphtho[1,2-b]pyran.

Example 7

The product from Example 2 (1.3 g) was dissolved in dry THF (25 mL). Sodium borohydride (0.33 g) was added while stirring at ambient temperature. After 10 hours the reaction mixture was poured in a flask containing 10% HCl (10 ml) then extracted with ethyl acetate (100 mL). The organic layer was washed once with brine (50 mL) and concentrated. The residue was purified using a CombiFlash Rf to yield pale yellow crystals (0.7 g). ¹H NMR analysis indicated that the product had a structure consistent with 10-(4-bromophenyl)-9-hydroxy-3-(4-butoxyphenyl)-3-(4-methoxyphenyl)-12,14,14-trimethyl-11-oxo-3,9,11,14-tetrahydropyrrolo[3',4':4,5]indeno[2',3':3,4]naphtho[1,2-b]pyran Example 8

Step 1

A solution containing the product from Step 4 of Example 1 (1 g), 4-(trans-4-pentylcyclohexyl)-N-(4-(4,4,5,5-tetramethyl-1,3,2-dioxaborolan-2-yl)phenyl)benzamide (1 g) and K₂CO₃ (1.5 g) in 1,2-dimethoxyethane (70 mL) and water (30 mL) was stirred and sparged with Nitrogen for 10 minutes, followed by addition of bis(triphenylphosphine)palladium (II)dichloride (0.13 g). The reaction mixture was heated to reflux for 8 hours, followed by extraction with ethyl acetate (100 mL). The organic phase was collected and concentrated. The residue was purified through a silica gel plug to yield a solid product (1.2 g). ¹H NMR showed that the product had a structure consistent with 11-(4'-(4-(trans-4-pentylcyclohexyl)benzamido)-[1,1'-biphenyl])-10,12-dioxo-7,7,9-trimethyl-7,10,11,12-tetrahydropyrrolo[3',4':4,5]indeno[3,2-a]naphthalen-5-ol.

Step 2

The procedure from Step 6 of Example 1 was followed except that the product from Step 1 of this example was used in place of the product from Step 5 of Example 1 and 1-(4-methoxyphenyl)-1-phenylprop-2-yn-1-ol was used in place of 1-(4-butoxyphenyl)-1-phenylprop-2-yn-1-ol. $^1$H NMR analysis showed the product had a structure consistent with 3-(4-methoxyphenyl)-14,14-dimethyl-9,11-dioxo-3-phenyl-12-(2-(2-phenylpropan-2-yl))-3,9,11,14-tetrahydrofuro[3',4':4,5]indeno[2',3':3,4]naphtho[1,2-b]pyran.

Example 9

A solution containing product from Example 7 (1 g), 4-((trans)-4-pentylcyclohexyl)-N-(4-(4,4,5,5-tetramethyl-1,3,2-dioxaborolan-2-yl)phenyl)benzamide (0.7 g) and Na$_2$CO$_3$ (0.8 g) in 1,2-dimethoxyethane (70 mL) and water (30 mL) was stirred for 10 minutes while sparging with Nitrogen. Then bis(triphenylphosphine)palladium(II)dichloride (0.15 g) was added and the reaction mixture was heated to reflux for 85 minutes. The mixture was extracted with ethyl acetate (100 mL) and the solvents removed by evaporation. The residue was purified through a silica gel plug eluting with 5/1 hexanes/ethyl acetate. The fractions containing the product were collected and further purified by using a CombiFlash Rf from Teledyne ISCO and recrystallization from acetone/methanol to yield a solid (0.5 g). $^1$H NMR analysis indicated that the product had a structure consistent with 3-(4-butoxyphenyl)-9-hydroxy-3-(4-methoxyphenyl)-10-(4'-(4-(trans-4-pentylcyclohexyl)benzamido)-[1,1'-biphenyl])-12,14,14-trimethyl-11-oxo-3,9,11,14-tetrahydropyrrolo[3',4':4,5]indeno[2',3':3,4]naphtho[1,2-b]pyran.

Example 10

The procedures from Example 9 were followed except the product from Example 4 was used in place of the product from Example 8. $^1$H NMR analysis indicated that the product had a structure consistent with 3-(4-methoxyphenyl)-14,14-dimethyl-9,11-dioxo-10-(4'-(4-(trans-4-pentylcyclohexyl)benzamido)-[1,1'-biphenyl])-3-phenyl-12-(2-phenylpropan-2-yl)-3,9,11,14-tetrahydropyrrolo[3',4':4,5]indeno[2',3':3,4]naphtho[1,2-b]pyran.

Example 11

The procedures from Example 1 were followed except that N-phenylmaleimide was used in place of N-(4-bromophenyl)maleimide in Step 4 and 1-(4-methoxyphenyl)-1-phenylprop-2-yn-1-ol was used in place of 1-(4-butoxyphenyl)-1-phenylprop-2-yn-1-ol in Step 6. $^1$H NMR analysis showed the product had a structure consistent with 10-phenyl-3-(4-methoxyphenyl)-12,14,14-trimethyl-9,11-dioxo-3-phenyl-3,9,11,14-tetrahydropyrrolo[3',4':4,5]indeno[2',3':3,4]naphtho[1,2-b]pyran.

Part 2

Photochromic Property Testing

Part 2A

Test Square Preparation

Testing was done with the compounds described in Examples in the following manner. A quantity of compound calculated to yield a 1.5×10$^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven, programmed to ramp from 40° C. to 95° C. over a 5 hour period, maintain the temperature at 95° C. for 3 hours, ramp down to 60° C. over a 2 hour period and then hold at 60° C. for 16 hours. After curing, the mold was opened, and the polymer sheet was cut into 2 inch (5.1 cm) test squares using a diamond blade saw.

Part 2B

Response Testing

Prior to response testing on an optical bench, the test squares from Part 2A were conditioned by exposing them to 365 nm ultraviolet light for 10 minutes at a distance of about 14 cm from the source in order to pre-activate the photochromic compounds in samples. The UVA irradiance at the sample surface was measured with a Licor Model Li-1800 spectroradiometer and found to be 22.2 Watts per square meter. The samples were then placed under a halogen lamp (500 W, 120V) for 10 minutes at a distance of 36 cm from the lamp in order to bleach, or inactivate, the photochromic compounds in the samples. The illuminance at the sample was measured with a Licor spectroradiometer and found to be 21.9 Klux. The samples were then kept in a dark environment for at least 1 hour prior to testing in order to cool and fade back to a ground state.

The optical bench was fitted with a Newport Model #67005 300-watt Xenon arc lamp, and Model 69911 power supply, Vincent Associates (model VS25S2ZM0R3 with VMM-D4 controller) high-speed computer controlled shutter, a Schott 3 mm KG-2 band-pass filter, which removed short wavelength radiation, neutral density filter(s) to attenuate light from the Xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 72±2° F. for photochromic response testing. A Newport Model 689456 Digital Exposure Timer was used to control the intensity of the Xenon arc lamp during activation of the sample.

A broadband light source for monitoring response measurements was positioned in a perpendicular manner to a surface of the cell assembly. Increased signal of shorter visible wavelengths was obtained by collecting and combining separately filtered light from a 100-Watt Tungsten halogen lamp (controlled by a Lambda UP60-14 constant voltage power supply) with a split-end, bifurcated fiber optical cable. Light from one side of the Tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing. After passing through the sample, the light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer. Adjustment of the output of the filtered Xenon arc lamp was accomplished by increasing or decreasing the current to the lamp through the controller and/or by adding or removing neutral density filters in the light path. The test samples were exposed to the activation light at 31° normal to the surface while being perpendicular to the monitoring light.

Samples were activated in the 73° F. (22.8° C.) controlled water cell for 30 minutes, then allowed to fade under room light conditions until the change in optical density of the activated sample faded to ¼ of its highest dark (saturated) state or for a maximum of 30 minutes of fade.

Change in optical density ($\Delta$OD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: $\Delta$OD=log(% Tb/% Ta), where % Tb is the percent transmittance in the bleached state, % Ta is the percent transmittance in the activated state and the logarithm is to the base 10.

The $\lambda_{max\text{-}vis}$ in the visible light range is the wavelength in the visible spectrum at which the maximum absorption of the activated form of the photochromic compound occurs. The $\lambda_{max\text{-}vis}$ was determined by testing the photochromic test square in a Varian Cary 4000 UV-Visible spectrophotometer or comparable equipment.

The $\Delta$OD/Min, which represents the sensitivity of the photochromic compound's response to UV light, was measured over the first five (5) seconds of UV exposure, then expressed on a per minute basis. The saturation optical density ($\Delta$OD at saturation) was taken under identical conditions except UV exposure was continued for a total of 30 minutes. The fade half-life (T ½) is the time interval in seconds for the $\Delta$OD of the activated form of the photochromic compound in the test squares to reach one half the $\Delta$OD measured after thirty minutes, or after saturation or near-saturation was achieved, at room temperature after removal of the source of activating light, e.g., by closing the shutter. Results are listed in Table 1.

TABLE 1

Photochromic Performance Test Results

| Example # | $\lambda_{max\text{-}vis}$ (nm) | Sensitivity ($\Delta$OD/Min) | $\Delta$OD at saturation | T ½ (sec) |
|---|---|---|---|---|
| 2  | 572 | 0.39 | 0.27 | 52  |
| 4  | 554 | 1.32 | 0.85 | 58  |
| 5  | 547 | 0.64 | 0.81 | 133 |
| 10 | 550 | 1.35 | 1.06 | 97  |
| 11 | 551 | 1.36 | 1.12 | 101 |

Part 3

Dichroic Property Testing

Part 3A

Liquid Crystal Cell Preparation

The average dichroic ratio of each of the compounds of Examples was determined according to the CELL METHOD described as follows.

A cell assembly having the following configuration was obtained from Design Concepts, Inc. Each of the cell assemblies was formed from two opposing glass substrates that are spaced apart with a glass bead spacer having a diameter of 20 microns +/−1 micron. The inner surfaces of each of the glass substrates had oriented polyimide coating thereon to provide for the alignment of a liquid crystal mate rial as discussed below. Two opposing edges of the glass substrates were sealed with an epoxy sealant, leaving the remaining two edges open for filling.

The gap between the two glass substrates of the cell assembly was filled with a liquid crystal solution containing the one of the compounds of Examples 8, 10 and 11. The liquid crystal solution was formed by mixing the following components in the weight percents listed below with heating, if necessary, to dissolve the test material.

| Material | Weight Percent |
|---|---|
| Licristal ™ E7 | 97-99.5 |
| Example Compound | 0.5-3 |

Part 3B

Liquid Crystal Cell Testing

An optical bench was used to measure the optical properties of the cell and derive the dichroic ratios for each of the Test Materials. The filled cell assembly was placed on the optical bench with an activating light source (an Oriel Model 66011 300-Watt Xenon arc lamp fitted with a Vincent Associates (model VS25S2ZM0R3 with VMM-D4 controller) high-speed computer controlled shutter that momentarily closed during data collection so that stray light would not interfere with the data collection process, a Schott 3 mm KG-1 band-pass filter, which removed short wavelength radiation, neutral density filter(s) for intensity attenuation and a condensing lens for beam collimation) positioned at a 30° to 35° angle of incidence a surface of the cell assembly.

A broadband light source for monitoring response measurements was positioned in a perpendicular manner to a surface of the cell assembly. Increased signal of shorter visible wavelengths was obtained by collecting and combining separately filtered light from a 100-Watt Tungsten halogen lamp (controlled by a Lambda UP60-14 constant voltage power supply) with a split-end, bifurcated fiber optical cable. Light from one side of the Tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing.

Polarization of the light source was achieved by passing the light from the single end of the cable through a Moxtek, Proflux Polarizer held in a computer driven, motorized rotation stage (Model M-061-PD from Polytech, PI). The monitoring beam was set so that the one polarization plane (0°) was perpendicular to the plane of the optical bench table and the second polarization plane (90°) was parallel to the plane of the optical bench table. The samples were run in air, at room temperature (73° F.±0.3° F. or better (22.8° C.±0.1° C.)) maintained by the lab air conditioning system or a temperature controlled air cell.

To conduct the measurements, the cell assembly and the coating stack were exposed to 6.7 W/m² of UVA from the activating light source for 5 to 15 minutes to activate the Test Material. An International Light Research Radiometer (Model IL-1700) with a detector system (Model SED033 detector, B Filter, and diffuser) was used to verify exposure prior to each test. Light from the monitoring source that was polarized to the 0° polarization plane was then passed through the coated sample and focused on a 1" integrating sphere, which was connected to an Ocean Optics S2000 spectrophotometer using a single function fiber optic cable. The spectral information, after passing through the sample, was collected using Ocean Optics SpectraSuite and PPG propriety software. While the photochromic-dichroic material was activated, the position of the polarizer was rotated back and forth to polarize the light from the monitoring light source to the 90° polarization plane and back. Data was collected for approximately 10 to 300 seconds at 5-second intervals during activation. For each test, rotation of the polarizers was adjusted to collect data in the following sequence of polarization planes: 0°, 90°, 90°, 0°, etc.

Absorption spectra were obtained and analyzed for each cell assembly using the Igor Pro software (available from WaveMetrics). The change in the absorbance in each polarization direction for each cell assembly was calculated by subtracting out the 0 time (i.e., unactivated) absorption measurement for the cell assembly at each wavelength tested. Average absorbance values were obtained in the region of the activation profile where the response of the Examples 8, 10 and 11 was saturated or nearly saturated (i.e., the regions where the measured absorbance did not increase or did not increase significantly over time) for each cell assembly by averaging absorbance at each time interval in this region. The average absorbance values in a predetermined range of wavelengths corresponding $\lambda_{max-vis}$+/−5 nm were extracted for the 0° and 90° polarizations, and the dichroic ratio for each wavelength in this range was calculated by dividing the larger average absorbance by the small average absorbance. For each wavelength extracted, 5 to 100 data points were averaged. The average dichroic ratio for the Test Material was then calculated by averaging these individual dichroic ratios.

For the Examples listed in Table 2 the above-described procedure was run at least twice. The tabled value for the Average Dichroic Ratio represents an average of the results obtained from the runs measured at the wavelength indicated. The results of these tests are present in Table 2 below.

TABLE 2

| Dichroic Ratio (DR) Test Data | | |
|---|---|---|
| Example # | Wavelength (nm) | Dichroic Ratio |
| 8 | 555 | 6.0 |
| 10 | 555 | 5.9 |
| 11 | 557 | 3.1 |

The present invention has been described with reference to specific details of particular embodiments thereof. It is not intended that such details be regarded as limitations upon the scope of the invention except insofar as to the extent that they are included in the accompanying claims.

What is claimed is:
1. A photochromic compound represented by Formula (I-A),

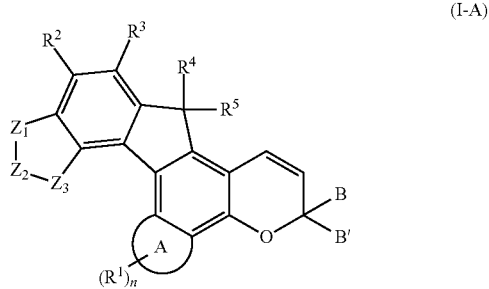

wherein,
Ring-A is selected from aryl and fused ring aryl,
n is selected from 1 to 8,
$R^1$, for each n, is in each case independently selected from hydrogen, hydrocarbyl and substituted hydrocarbyl each optionally and independently interrupted with at least one of —O—, —S—, —C(O)—, —C(O)O—, —S(O)—, —SO$_2$—, —N═N—, —N($R_{11}$')— where $R_{11}$' is selected from hydrogen, hydrocarbyl or substituted hydrocarbyl, —Si(OR$_8$')$_w$(R$_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more thereof; halogen; cyano; —O-R$_{10}$' or —S-R$_{10}$' or —C(O)—R$_{10}$' or —C(O)—OR$_{10}$', wherein each R$_{10}$' is independently selected from hydrogen, hydrocarbyl or substituted hydrocarbyl; perhalohydrocarbyl; and —C(O)—N(R$_{11}$')(R$_{12}$') or —N(R$_{11}$')R$_{12}$', wherein R$_{11}$' and R$_{12}$' are each independently selected from hydrogen, hydrocarbyl or substituted hydrocarbyl, or R$_{11}$' and R$_{12}$' together form a ring structure optionally including at least one heteroatom,
$R^2$ and $R^3$ are each independently selected from hydrogen, hydrocarbyl, substituted hydrocarbyl, halogen, —C(O)—N($R_{14}$)($R_{15}$), —N($R_{14}$)($R_{15}$), —SR$_{16}$, and —OR$_{16}$, where R$_{14}$ and R$_{15}$ are each independently selected from hydrogen, hydrocarbyl, and substituted hydrocarbyl, or $R_{14}$ and $R_{15}$ together form a ring, and each $R_{16}$ is independently selected from hydrocarbyl and substituted hydrocarbyl, $R^4$ and $R^5$ are each independently selected from hydrogen, hydrocarbyl, and substituted hydrocarbyl, each optionally and independently interrupted with —O—, —S—, —N($R_{11}$')—, where $R_{11}$' is selected from hydrogen, hydrocarbyl or substituted hydrocarbyl, $Z_1$ and $Z_3$ are each independently selected from O, C(O) and C($R_a$)($R_b$), where $R_a$ and $R_b$ are each independently selected from hydrogen, hydroxyl, and $C_1$-$C_{20}$ linear or branched alkyl, provided that at least one of $Z_1$ and $Z_3$ is C(O), $Z_2$ is selected from O, S, divalent hydrocarbyl, and N—$R_{13}$, where $R_{13}$ is selected from hydrogen, hydrocarbyl and substituted hydrocarbyl each optionally and independently interrupted with at least one of —O—, —S—, —C(O)—, —C(O)O—, —S(O)—, —SO$_2$—, —N=N—, —N($R_{11}$')— where $R_{11}$' is selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more thereof, or $Z_2$ defines an optionally substituted fused ring, and B and B' are each independently selected from, hydrogen, hydrocarbyl and substituted hydrocarbyl each optionally and independently interrupted with at least one of —O—, —S—, —C(O)—, —C(O)O—, —S(O)—, —SO$_2$—, —N=N—, —N($R_{11}$')— where $R_{11}$' is selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more thereof.

2. The photochromic compound of claim 1 wherein, Ring-A, for Formula (I-A), is selected from aryl;

$R^1$, for Formula (I-A), for each n is independently selected from,
hydrogen;
halogen selected from fluoro, bromo, iodo, and chloro;
$C_1$-$C_{20}$ linear or branched alkyl;
$C_3$-$C_{10}$ cycloalkyl;
substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy;
—O—$R_{10}$' or —S-$R_{10}$', wherein each $R_{10}$' independently is hydrogen, $C_1$-$C_{20}$ alkyl, phenyl($C_1$-$C_{20}$)alkyl, mono($C_1$-$C_{20}$)alkyl substituted phenyl($C_1$-$C_{20}$)alkyl, mono($C_1$-$C_2$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_2$)alkyl substituted $C_3$-$C_{10}$ cycloalkyl;
—N($R_{11}$')$R_{12}$' or —C(O)—N($R_{11}$')($R_{12}$'), wherein $R_{11}$' and $R_{12}$' are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}$' and $R_{12}$' come together with the nitrogen atom to form a $C_3$-$C_{20}$ hetero-bicycloalkyl ring or a $C_4$-$C_{20}$ hetero-tricycloalkyl ring;

a nitrogen containing ring represented by graphic formula XIIA,

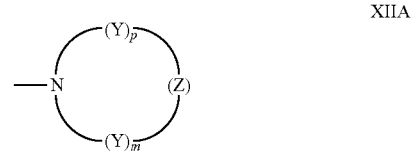

wherein each —Y— is independently chosen for each occurrence from CH$_2$, —CH($R_{13}$')—, —C($R_{13}$')$_2$—, —CH(aryl)-, —C(aryl)$_2$-, and —C($R_{13}$')(aryl)-, and Z is —Y—, —O—, —S—, —S(O)—, —SO$_2$—, —NH—, —N($R_{13}$')—, or —N(aryl)-, wherein each $R_{13}$' is independently $C_1$-$C_{20}$ alkyl, each aryl is independently phenyl or naphthyl, m is an integer 1, 2 or 3, and p is an integer 0, 1, 2, or 3 and provided that when p is 0, Z is —Y—;

a group represented by one of the following graphic formulas XIIB or XIIC,

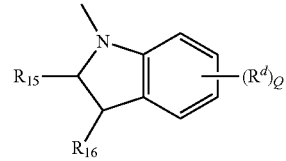

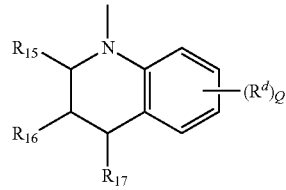

wherein $R_{15}$, $R_{16}$, and $R_{17}$ are each independently hydrogen, $C_1$-$C_{20}$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_{20}$ alkyl, $C_1$-$C_{20}$ alkoxy, or phenyl($C_1$-$C_{20}$)alkyl; or two adjacent $R^1$ groups together form a group represented by one of XIID and XIIE:

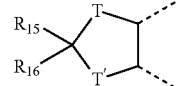

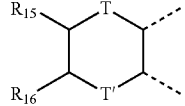

wherein T and T' are each independently oxygen or the group —NR$_{11}$'—, where R$_{11}$', R$_{15}$, and R$_{16}$ are as set forth above;

R$^2$ and R$^3$, for Formula (I-A), are each independently selected from, hydrogen, halogen selected from F, Cl, Br, and I, C$_1$-C$_{20}$ linear or branched alkyl;

C$_3$-C$_{10}$ cycloalkyl;

substituted or unsubstituted phenyl, the phenyl substituents being selected from hydroxyl, halogen, carbonyl, C$_1$-C$_{20}$ alkoxycarbonyl, cyano, halo(C$_1$-C$_{20}$)alkyl, C$_1$-C$_{20}$ alkyl or C$_1$-C$_{20}$ alkoxy;

—C(O)N(R$_{14}$)(R$_{15}$) or —N(R$_{14}$)(R$_{15}$), where R$_{14}$ and R$_{15}$ are each independently selected from, hydrogen, C$_1$-C$_{20}$ linear or branched alkyl;

C$_3$-C$_{10}$ cycloalkyl; and substituted or unsubstituted phenyl, the phenyl substituents being selected from halogen, halo(C$_1$-C$_{20}$)alkyl, C$_1$-C$_{20}$ alkyl or C$_1$-C$_{20}$ alkoxy; or R$_{14}$ and R$_{15}$ together form a ring; and —OR$_{16}$ or —SR$_{16}$, where each R$_{16}$ is independently selected from, C$_1$-C$_{20}$ linear or branched alkyl;

C$_3$-C$_{10}$ cycloalkyl; and substituted or unsubstituted phenyl, the phenyl substituents being selected from halogen, halo(C$_1$-C$_{20}$)alkyl, C$_1$-C$_{20}$ alkyl or C$_1$-C$_{20}$ alkoxy;

R$^4$ and R$^5$, for Formula (I-A), are each independently selected from, (i) hydrogen, C$_1$-C$_{20}$ alkyl, C$_1$-C$_{20}$ haloalkyl, C$_3$-C$_{10}$ cycloalkyl, allyl, benzyl, or mono-substituted benzyl, said benzyl substituents being chosen from halogen, C$_1$-C$_{20}$ alkyl or C$_1$-C$_{20}$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, C$_1$-C$_{20}$ alkyl or C$_1$-C$_{20}$ alkoxy;

(iii) mono-substituted phenyl, said substituent located at the para position being —(CH$_2$)$_t$— or —O—(CH$_2$)$_t$—, wherein t is the integer 1, 2, 3, 4, 5 or 6, said substituent being connected to an aryl group which is a member of a photochromic material; and (iv) the group —CH(R$^{10}$)G, wherein R$^{10}$ is hydrogen, C$_1$-C$_6$ alkyl or the unsubstituted, mono- or di-substituted aryl groups phenyl or naphthyl, and G is —CH$_2$OR$^{11}$, wherein R$^{11}$ is hydrogen, C$_1$-C$_{20}$ alkyl, C$_1$-C$_{20}$ alkoxy(C$_1$-C$_{20}$)alkyl, phenyl(C1-C20)alkyl, mono(C$_1$-C$_{20}$)alkoxy substituted phenyl(C$_1$-C$_{20}$) alkyl, or the unsubstituted, mono- or di-substituted aryl groups phenyl or naphthyl, each of said phenyl and naphthyl group substituents being C$_1$-C$_{20}$ alkyl or C$_1$-C$_{20}$ alkoxy; or (v) R$^4$ and R$^5$ together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom, said spiro-carbocyclic ring and spiro-heterocyclic ring being annellated with 0, 1 or 2 benzene rings, said substituents being hydrogen or C$_1$-C$_{20}$ alkyl; and B and B' are each independently:

an aryl group that is mono-substituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently:

hydroxyl, a group —C(=O)R$_{21}$, wherein R$_{21}$ is —OR$_{22}$, —N(R$_{23}$)R$_{24}$, piperidino, or morpholino, wherein R$_{22}$ is allyl, C$_1$-C$_{20}$ alkyl, phenyl, mono (C1-C20)alkyl substituted phenyl, mono(C1-C20) alkoxy substituted phenyl, phenyl(C1-C20)alkyl, mono(C1-C20)alkyl substituted phenyl(C$_1$-C$_{20}$) alkyl, mono(C$_1$-C$_{20}$)alkoxy substituted phenyl(C$_1$-C20)alkyl, C$_1$-C$_{20}$ alkoxy(C$_2$-C$_{20}$)alkyl or C$_1$-C$_{20}$ haloalkyl, R$_{23}$ and R$_{24}$ are each independently C$_1$-C$_{20}$ alkyl, C$_5$-C$_{10}$ cycloalkyl, phenyl or substituted phenyl, the phenyl substituents being C$_1$-C$_{20}$ alkyl or C$_1$-C$_{20}$ alkoxy, and said halo substituent is chloro or fluoro, aryl, mono(C$_1$-C$_{20}$)alkoxyaryl, di(C$_1$-C$_{20}$)alkoxyaryl, mono(C$_1$-C$_{20}$)alkylaryl, di(C$_1$-C$_{20}$)alkylaryl, haloaryl, C$_3$-C$_{10}$ cycloalkylaryl, C$_3$-C$_{10}$ cycloalkyl, C$_3$-C$_{10}$ cycloalkyloxy, C$_3$-C$_{10}$ cycloalkyloxy(C1-C20)alkyl, C$_3$-C$_{10}$ cycloalkyloxy(C1-C20)alkoxy, aryl(C$_1$-C$_{20}$)alkyl, aryl(C$_1$-C$_{20}$)alkoxy, aryloxy, aryloxy(C1-C20) alkyl, aryloxy(C$_1$-C$_{20}$)alkoxy, mono- or di(C$_1$-C$_{20}$)alkylaryl(C$_1$-C$_{20}$)alkyl, mono- or di-(C$_1$-C$_{20}$) alkoxyaryl(C$_1$-C$_{20}$)alkyl, mono- or di-(C$_1$-C$_{20}$) alkylaryl(C$_1$-C$_{20}$)alkoxy, mono- or di-(C$_1$-C$_{20}$) alkoxyaryl(C$_1$-C$_{20}$)alkoxy, amino, mono- or di-(C$_1$-C$_{20}$)alkylamino, diarylamino, piperazino, N—(C$_1$-C$_{20}$)alkylpiperazino, N-arylpiperazino, aziridino, indolino, piperidino, morpholino, thiomorpholino, tetrahydroquinolino, tetrahydroisoquinolino, pyrrolidyl, C$_1$-C$_{20}$ alkyl, C$_1$-C$_{20}$ haloalkyl, C$_1$-C$_{20}$ alkoxy, mono(C$_1$-C$_{20}$)alkoxy (C$_1$-C$_{20}$)alkyl, acryloxy, methacryloxy, or halogen;

an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being C$_1$-C$_{20}$ alkyl, C$_1$-C$_{20}$ alkoxy, phenyl, or halogen;

a group represented by one of:

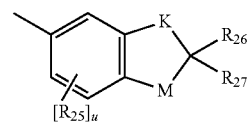

and

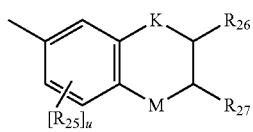

wherein K is —CH$_2$— or —O—, and M is —O— or substituted nitrogen, provided that when M is substituted nitrogen, K is —CH$_2$—, the substituted nitrogen substituents being hydrogen, C$_1$-C$_{20}$ alkyl, or C$_1$-C$_{20}$ acyl, each R$_{25}$ being independently chosen for each occurrence from C$_1$-C$_{20}$ alkyl, C$_1$-C$_{20}$ alkoxy, hydroxy, and halogen, R$_{26}$ and R$_{27}$ each being independently hydrogen or C$_1$-C$_{20}$ alkyl, and u is an integer ranging from 0 to 2; or a group represented by:

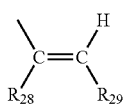

wherein R$_{28}$ is hydrogen or C$_1$-C$_{20}$ alkyl, and R$_{29}$ is an unsubstituted, mono-, or di-substituted group chosen from naphthyl, phenyl, furanyl, and thienyl, wherein the substituents are C$_1$-C$_{20}$ alkyl, C$_1$-C$_{20}$ alkoxy, or halogen; or B and B' taken together form one of a fluoren-9-ylidene, mono-, or di-substituted fluoren-9-ylidene, each of said fluoren-9-ylidene substituents being independently chosen from C$_1$-C$_{20}$ alkyl, C$_1$-C$_{20}$ alkoxy, and halogen.

3. The photochromic compound of claim 2 wherein, Ring-A, for Formula (I-A), is C$_6$-aryl, R$^1$, for Formula (I-A), for each n is independently selected from hydrogen, C$_1$-C$_6$ linear or branched alkyl, C$_3$-C$_7$ cycloalkyl, C$_1$-C$_8$ haloalkyl, fluoro, chloro, bromo, iodo, and —O—R$_{10}$', R$^2$ and R$^3$, for Formula (I-A), are each independently selected from
hydrogen,
C$_1$-C$_6$ linear or branched alkyl;
C$_3$-C$_7$ cycloalkyl; and
substituted or unsubstituted phenyl, the phenyl substituents being selected from halogen, halo(C$_1$-C$_6$)alkyl, C$_1$-C$_6$ alkyl or C$_1$-C$_6$ alkoxy;

R$^4$ and R$^5$, for Formula (I-A), are each independently selected from hydrogen, C$_1$-C$_8$ alkyl, C$_1$-C$_8$ haloalkyl, and C$_3$-C$_7$ cycloalkyl, or R$^4$ and R$^5$ together form a spiro substituent selected from a substituted or unsubstituted spiro-carbocyclic ring containing 3 to 6 carbon atoms; and B and B' are each independently selected from phenyl, and phenyl substituted with at least one of fluoro, C$_1$-C$_6$ alkyl, C$_1$-C$_6$ alkoxy, morpholino, piperidino, and pyrrolidino.

4. The photochromic compound of claim 1 wherein,
Z$_2$ is N—R$_{13}$, and R$_{13}$ is a group L represented by Formula (II), and
optionally at least one R$^1$ independently for each n, is selected from said group L represented by Formula (II).

-[S$_1$]$_c$-[Q$_1$-[S$_2$]$_d$]$_d$-[Q$_2$-[S$_3$]$_e$]$_e$-[Q$_3$-[S$_4$]$_f$]$_f$-S$_5$—P       Formula (II)

wherein:

(a) Q$_1$, Q$_2$, and Q$_3$ for each occurrence, are independently selected from a divalent group selected from optionally substituted aryl, optionally substituted heteroaryl, optionally substituted cycloalkyl, and optionally substituted heterocycloalkyl;

wherein the aryl substituents, heteroaryl substituents, cycloalkyl substituents, and heterocycloalkyl substituents are each independently selected from P, liquid crystal mesogens, halogen, poly(C$_1$-C$_{18}$ alkoxy), C$_1$-C$_{18}$ alkoxycarbonyl, C$_1$-C$_{18}$ alkylcarbonyl, C$_1$-C$_{18}$ alkoxycarbonyloxy, aryloxycarbonyloxy, perfluoro(C$_1$-C$_{18}$) alkoxy, perfluoro(C$_1$-C$_{18}$)alkoxycarbonyl, perfluoro (C$_1$-C$_{18}$)alkylcarbonyl, perfluoro(C$_1$-C$_{18}$)alkylamino, di-(perfluoro(C$_1$-C$_{18}$)alkyl)amino, perfluoro(C$_1$-C$_{18}$) alkylthio, C$_1$-C$_{18}$ alkylthio, C$_1$-C$_{18}$ acetyl, C$_3$-C$_{10}$ cycloalkyl, C$_3$-C$_{10}$ cycloalkoxy, straight-chain C$_1$-C$_{18}$ alkyl, and branched C$_1$-C$_{18}$ alkyl;

wherein said straight-chain C$_1$-C$_{18}$ alkyl and branched C$_1$-C$_{18}$ alkyl are mono-substituted with a group selected from cyano, halogen, and C$_1$-C$_{18}$ alkoxy; or wherein said straight-chain C$_1$-C$_{18}$ alkyl and branched C$_1$-C$_{18}$ alkyl are poly-substituted with at least two groups independently selected from halogen, -M(T)$_{(v-1)}$ and -M(OT)$_{(v-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M;

(b) c, d, e, and f are each independently chosen from an integer of 1 to 20; and each S$_1$, S$_2$, S$_3$, S$_4$, and S$_5$ is independently chosen for each occurrence from a spacer unit selected from:

(i) optionally substituted alkylene, optionally substituted haloalkylene, —Si(CH$_2$)$_g$—, and —(Si [(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from C$_1$-C$_{18}$ alkyl, C$_3$-C$_{10}$ cycloalkyl and aryl;

(ii) —N(Z)—, —C(Z)=C(Z)—, —C(Z)=N—, —C(Z')$_2$—C(Z')$_2$—, and a single bond, wherein Z for each occurrence is independently selected from hydrogen, C$_1$-C$_{18}$ alkyl, C$_3$-C$_{10}$ cycloalkyl and aryl, and Z' for each occurrence is independently selected from C$_1$-C$_{18}$ alkyl, C$_3$-C$_{10}$ cycloalkyl and aryl; and (iii) —O—, —C(=O)—, —C≡C—, —N=N—, —S—, —S(=O)—, —(O=)S(=O)—, —(O=)S (=O)O—, —O(O=)S(=O)O— and straight-chain or branched C$_1$-C$_{24}$ alkylene residue, said C$_1$-C$_{24}$ alkylene residue being unsubstituted, mono-substituted by cyano or halogen, or poly-substituted by halogen, provided that when two spacer units comprising heteroatoms are linked together the spacer units are linked so that heteroatoms are not directly linked to each other, the bond between R$_{13}$ and the nitrogen atom of N—R$_{13}$ is free of two heteroatoms linked to each other, and the bond between S$_5$ and P is free of two heteroatoms linked to each other;

(c) P for each occurrence is independently selected from hydroxy, amino, C$_2$-C$_{18}$ alkenyl, C$_2$-C$_{18}$ alkynyl, azido, silyl, siloxy, silylhydride, (tetrahydro-2H-pyran-2-yl) oxy, thio, isocyanato, thioisocyanato, acryloyloxy, methacryloyloxy,       2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$) alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, mainchain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound; and (d) d', e' and f are each independently chosen from 0, 1, 2, 3, and 4, provided that the sum of d'+e'+f is at least 1.

5. The photochromic compound of claim 4 wherein, for said group L represented by Formula (II), (a) $Q_1$, $Q_2$, and $Q_3$ for each occurrence, are independently selected from optionally substituted aryl and optionally substituted cycloalkyl, (b) each $S_1$, $S_2$, $S_3$, $S_4$, and $S_5$ is independently chosen for each occurrence from a spacer unit selected from, (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl, and (iii) —O—, —C(=O)—, —C≡C—, —N=N—, —S—, —S(=O)—, and straight-chain or branched $C_1$-$C_{12}$ alkylene residue, said $C_1$-$C_{12}$ alkylene residue being unsubstituted, mono-substituted by cyano or halogen, or poly-substituted by halogen, and (c) P for each occurrence is independently selected from hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$-$C_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$)alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$) alkoxy, $C_1$-$C_8$ alkoxy($C_1$-$C_8$)alkoxy, nitro, poly($C_1$-$C_8$) alkyl ether, ($C_1$-$C_8$)alkyl($C_1$-$C_8$)alkoxy($C_1$-$C_8$)alkyl, polyethyleneoxy, polypropyleneoxy, ethylene, acryloyl, acryloyloxy($C_1$-$C_{18}$)alkyl, methacryloyl, methacryloyloxy($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, and vinyl ester.

6. The photochromic compound of claim 5 wherein, for said group L represented by Formula (II), (b) each $S_1$, $S_2$, $S_3$, $S_4$, and $S_5$ is independently chosen for each occurrence from a spacer unit selected from, (ii) —N(Z)—, —C(Z)=C(Z)—, and a single bond, wherein Z for each occurrence is independently selected from hydrogen, $C_1$-$C_8$ alkyl, C3-C6 cycloalkyl and aryl, and (iii) —O—, —C(=O)—, —C≡C—, and straight-chain or branched $C_1$-$C_6$ alkylene residue, said $C_1$-$C_6$ alkylene residue being unsubstituted, mono-substituted by cyano or halogen, or poly-substituted by halogen, and (c) P for each occurrence is independently selected from hydrogen, hydroxy, amino, $C_2$-$C_8$ alkenyl, $C_2$-$C_8$ alkynyl, and aryl.

7. The photochromic compound of claim 1 wherein $Z_1$ and $Z_3$ are each C(O).

8. The photochromic compound of claim 1 wherein said photochromic compound is represented by Formula (I-B),

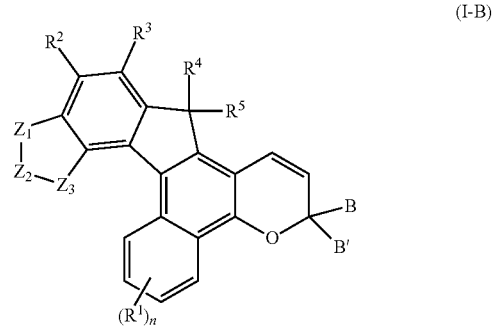

(I-B)

wherein n is selected from 1 to 4.

9. The photochromic compound of claim 4, wherein each group L is independently selected from, L(1) 4-[4-(4-butyl-cyclohexyl)-phenyl]-cyclohexyloxy

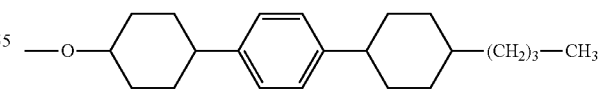

L(2) 4''-butyl-[1,1';4',1'']tercyclohexan-4-yloxy

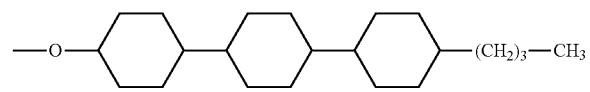

L(3) 4-[4-(4-butyl-phenyl)-cyclohexyloxycarbonyl]-phenoxy

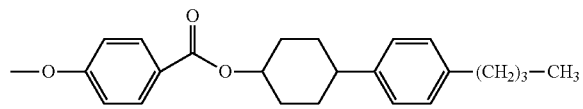

L(4) 4'-(4-butyl-benzoyloxy)-biphenyl-4-carbonyloxy

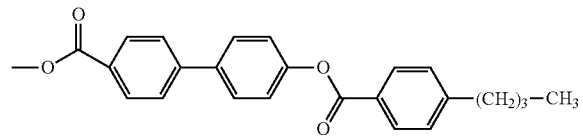

L(5) 4-(4-pentyl-phenylazo)-phenylcarbamoyl

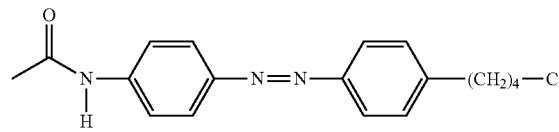

L(6) 4-(4-dimethylamino-phenylazo)-phenylcarbamoyl

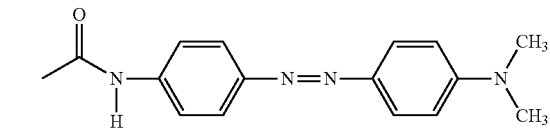 [SMILES: CC(=O)Nc1ccc(N=Nc2ccc(N(C)C)cc2)cc1]

L(7) {4-[5-(4-propyl-benzoyloxy)-pyrimidin-2-yl]-phenyl}ester

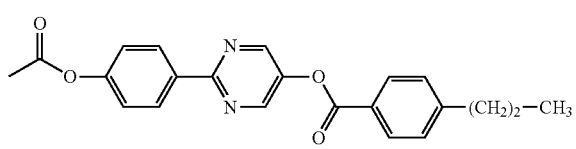

L(8) {4-[2-(4'-methyl-biphenyl-4-carbonyloxy)-1,2-diphenyl-ethoxycarbonyl]-phenyl}ester

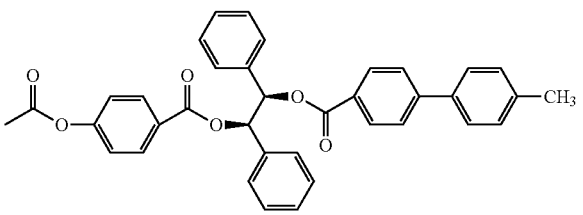 [SMILES: CC(=O)Oc1ccc(C(=O)O[C@H](c2ccccc2)[C@H](OC(=O)c2ccc(-c3ccc(C)cc3)cc2)c2ccccc2)cc1]

L(9) [4-(1,2-diphenyl-2-{3-[4-(4-propyl-benzoyloxy)-phenyl]-acryloyloxy}-ethoxycarbonyl)-phenyl]ester

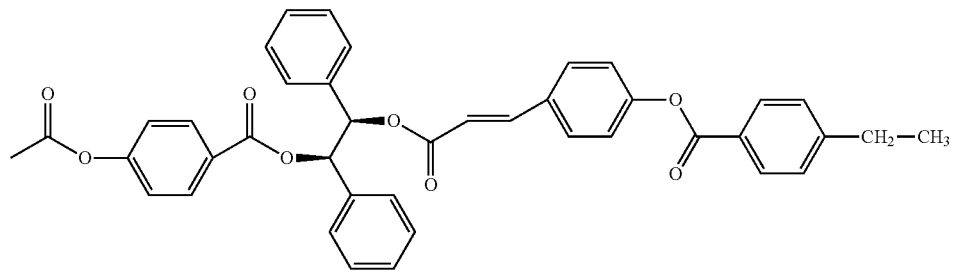 [SMILES: CCc1ccc(C(=O)Oc2ccc(/C=C/C(=O)O[C@H](c3ccccc3)[C@H](OC(=O)c3ccc(OC(C)=O)cc3)c3ccccc3)cc2)cc1]

L(10) 4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl]-piperazin-1-yl

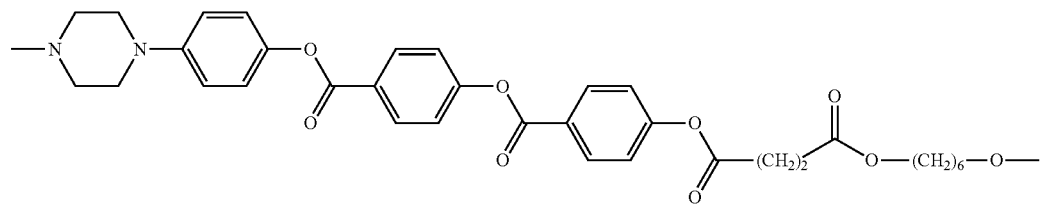

-continued

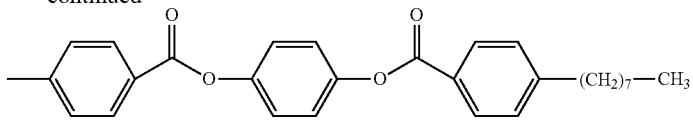

L(11) {4-[4-(4-{4-[4-(4-nonyl-benzoyloxy)-benzoyloxy]-benzoyloxy}-benzoyloxy)-phenyl]-piperazin-1-yl}

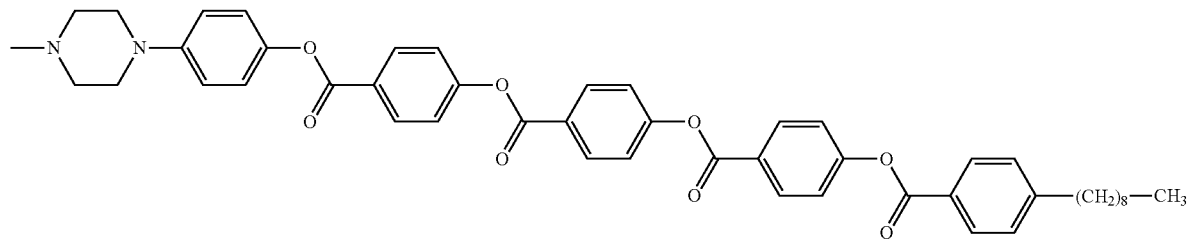

L(12) 4-(4'-propyl-biphenyl-4-ylethynyl)-phenyl

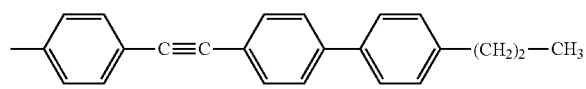

L(13) 4-(4-fluoro-phenoxycarbonyloxy)-piperidin-1-yl

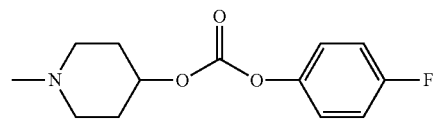 [SMILES: CN1CCC(OC(=O)Oc2ccc(F)cc2)CC1]

L(14) 2-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-indan-5-yl

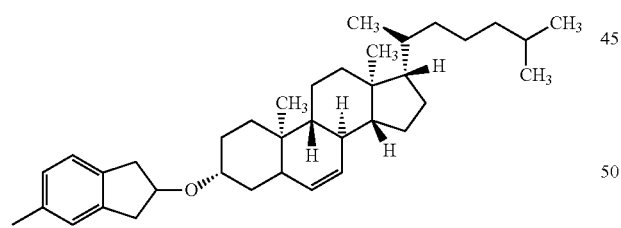

L(15) 4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl

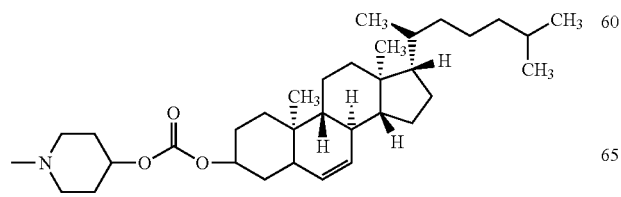

L(16) 4-(biphenyl-4-carbonyloxy)-piperidin-1-yl

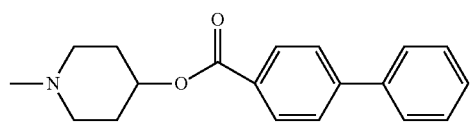

L(17) 4-(naphthalene-2-carbonyloxy)-piperidin-1-yl

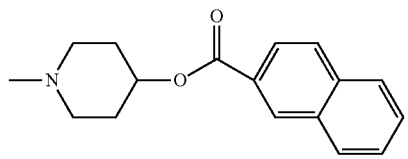 [SMILES: CN1CCC(OC(=O)c2ccc3ccccc3c2)CC1]

L(18) 4-hydroxy-piperidin-1-yl

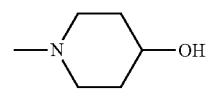

L(19) 4-(4-phenylcarbamoyl-phenylcarbamoyl)-piperidin-1-yl

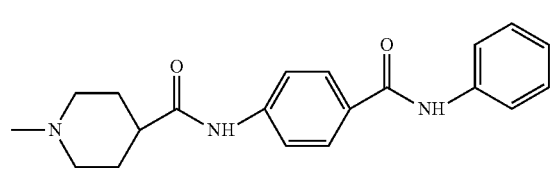 [SMILES: CN1CCC(C(=O)Nc2ccc(C(=O)Nc3ccccc3)cc2)CC1]

L(20) 4-(4-(4-phenylpiperidin-1-yl)-benzoyloxy)-piperidin-1-yl

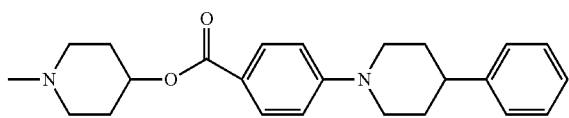

L(21) 4-butyl-[1,1';4',1'']terphenyl-4-yl

L(22) 4-(4-pentadecafluoroheptyloxy-phenylcarbamoyl)-benzyloxy

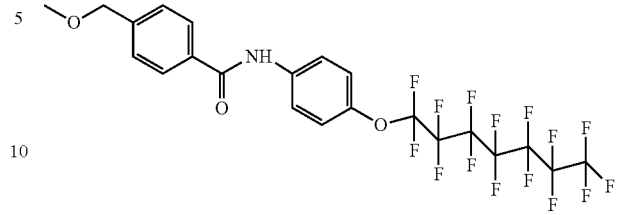

L(23) 4-(3-piperidin-4-yl-propyl)-piperidin-1-yl

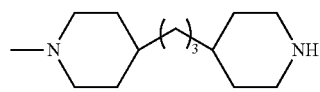

L(24) 4-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-benzoyloxy}-phenoxycarbonyl)-phenoxymethyl

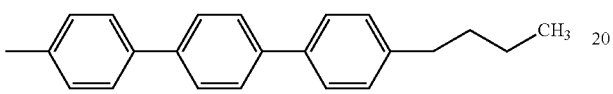

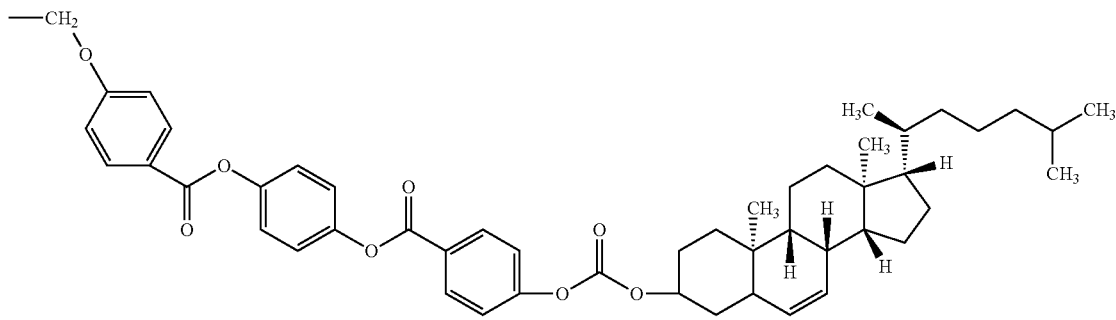

L(25) 4-[4-(4-cyclohexyl-phenylcarbamoyl)-benzyloxy]-piperidin-1-yl

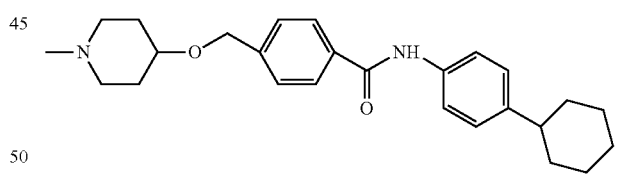

L(26) 4-[4-(4-cyclohexyl-phenylcarbamoyl)-benzoyloxy]-piperidin-1-yl

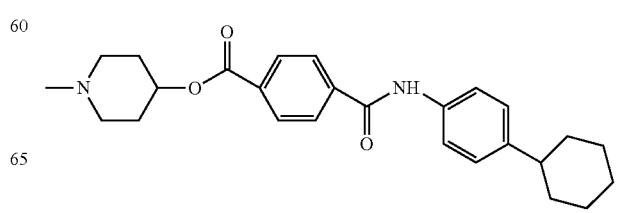

L(27) N-{4-[(4-pentyl-benzylidene)-amino]-phenyl}-acetamidyl

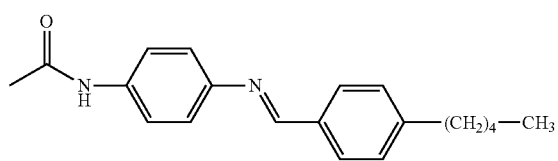

L(28) 4-(3-piperidin-4-yl-propyl)-piperidin-1-yl

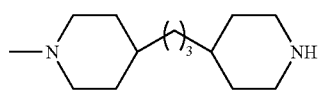

L(29) 4-(4-hexyloxy-benzoyloxy)-piperidin-1-yl]

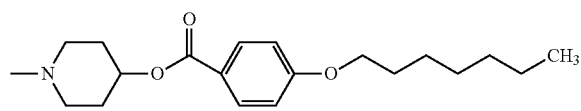 [SMILES: CCCCCCCOc1ccc(C(=O)OC2CCN(C)CC2)cc1]

L(30) 4-(4'-hexyloxy-biphenyl-4-carbonyloxy)-piperidin-1-yl

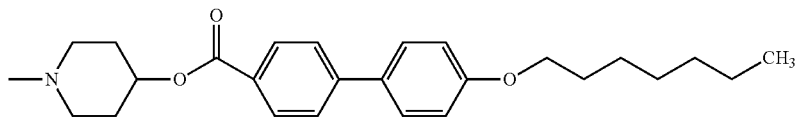 [SMILES: CCCCCCCOc1ccc(-c2ccc(C(=O)OC3CCN(C)CC3)cc2)cc1]

L(31) 4-(4-butyl-phenylcarbamoyl)-piperidin-1-yl

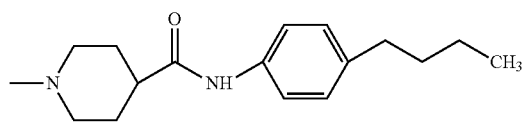

L(32a) 1-methyl-4-((4'-(((1-methylpiperidin-4-yl)oxy)carbonyl)-[1,1'-biphenyl]-4-carbonyl)oxy)piperidin-1-yl

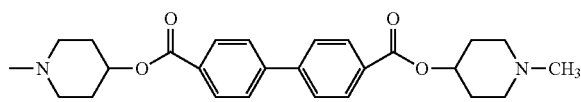

L(32b) bis(1-yl-piperidin-4-yl) [1,1'-biphenyl]-4,4'-dicarboxylate (which links two separate photochromic PC groups)

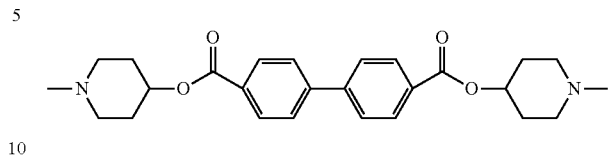

L(33) 4-(4-(9-(4-butylphenyl)-2,4,8,10-tetraoxaspiro[5.5]undec-3-yl)phenyl)piperazin-1-yl

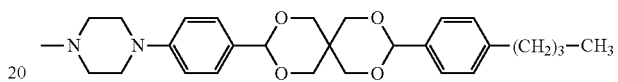

L(34) 4-(6-(4-butylphenyl)carbonyloxy-(4,8-dioxabicyclo[3.3.0]oct-2-yl))oxycarbonyl)phenyl

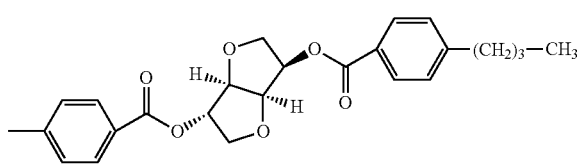

L(35) 1-{4-[5-(4-butyl-phenyl)-[1,3]dioxan-2-yl]-phenyl}-4-methyl-piperazin-1-yl

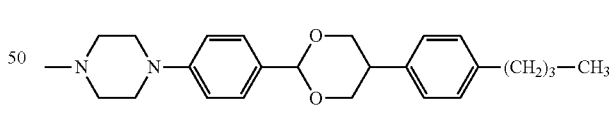

L(36) 4-(7-(4-propylphenylcarbonyloxy)bicyclo[3.3.0]oct-2-yl)oxycarbonyl)phenyl

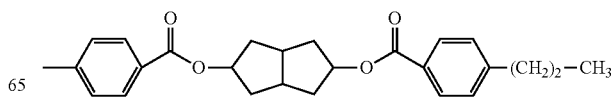

L(37) 4-[17-(1,5-dimethyl-hexyl)-10,13-dimethyl-2,3,4,
7,8,9,10,11,12,13,14,15,16,17-tetradecahydro-1H-cy-
clopenta[a]phenanthren-3-yloxycarbonyloxy
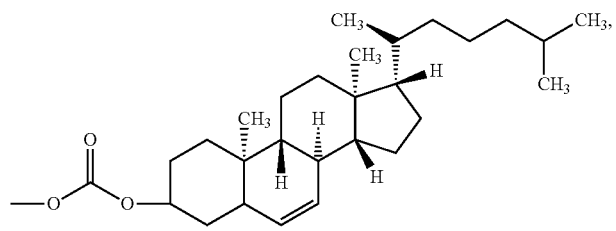
L(a)
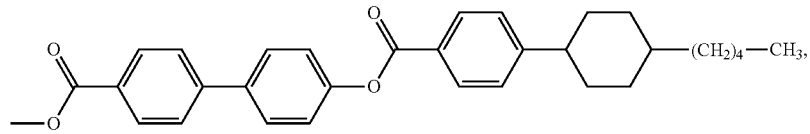
L(b)
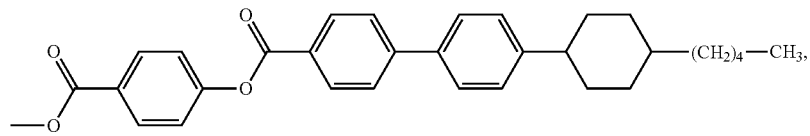
L(c)
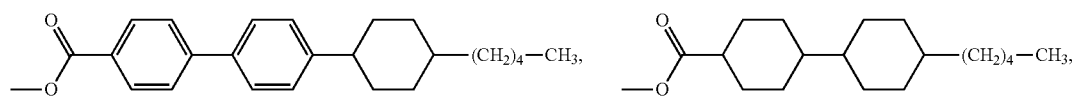
L(d)
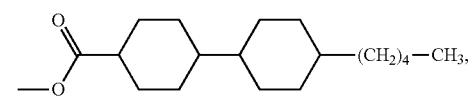
L(e)
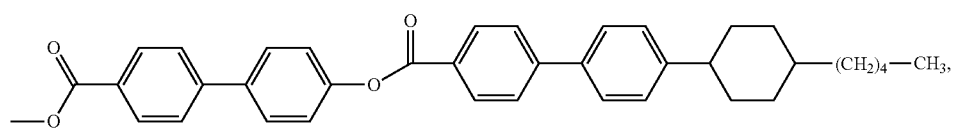
L(f)
L(g)
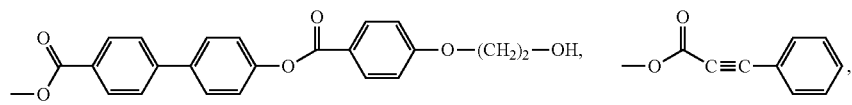
L(h)
L(i)
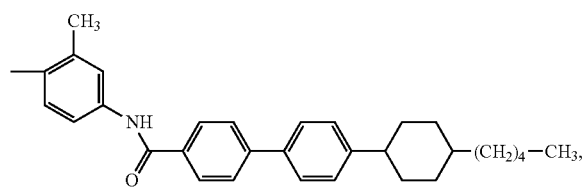
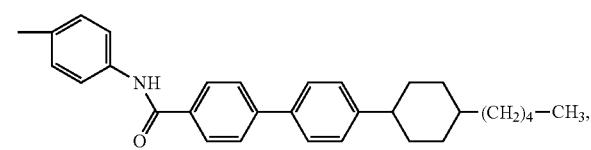
L(j)
L(k)
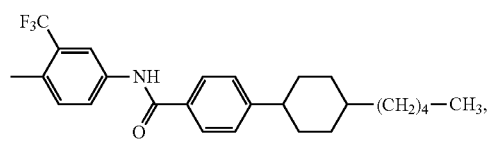
L(l)
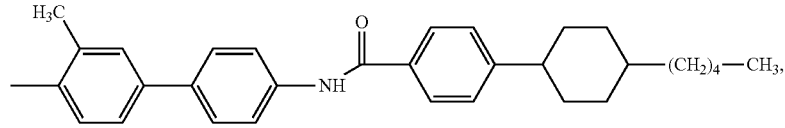
L(m)
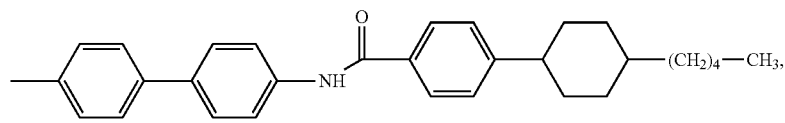

-continued
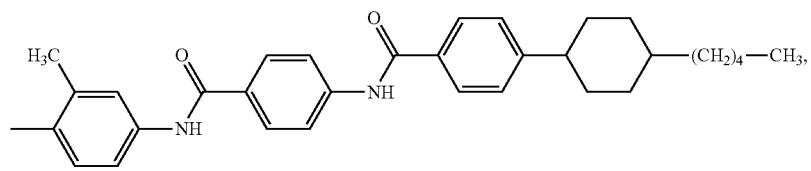
L(n)
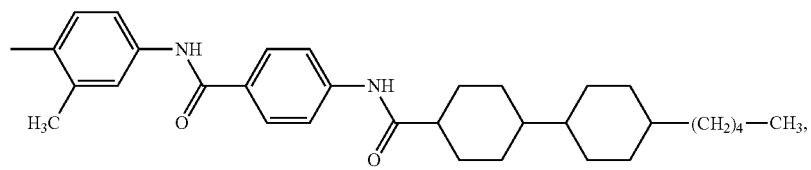
L(o)
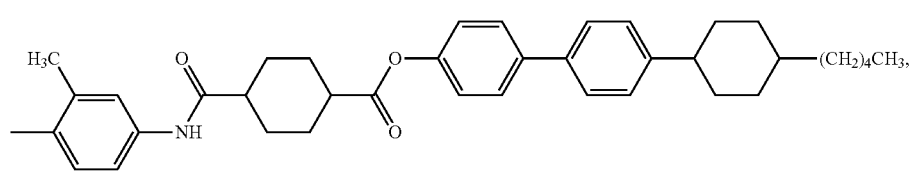
L(p)
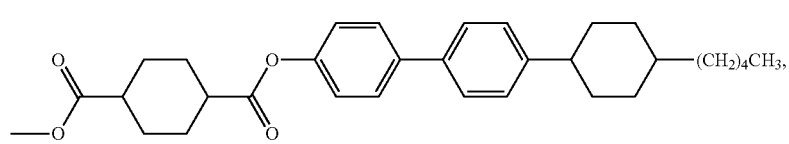
L(q)
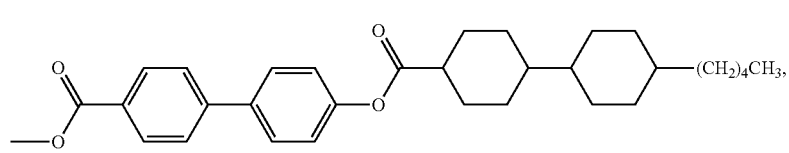
L(r)
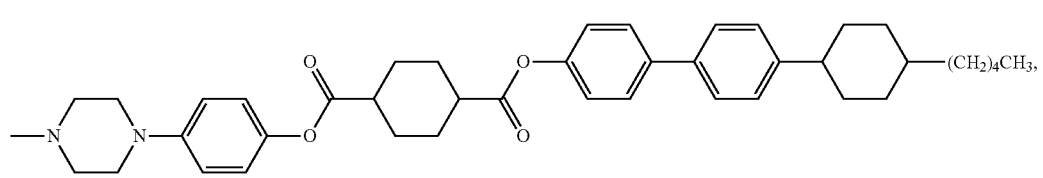
L(s)
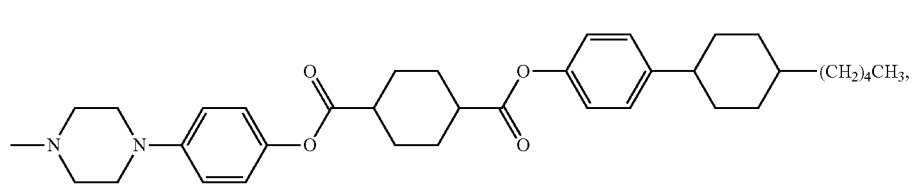
L(t)
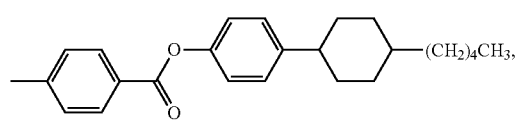
L(u)
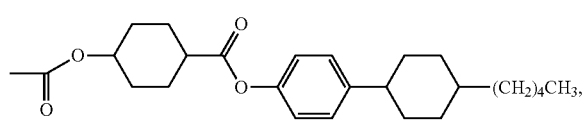
L(v)
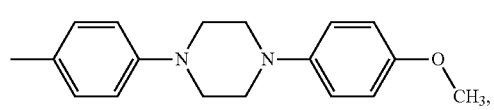
L(w)
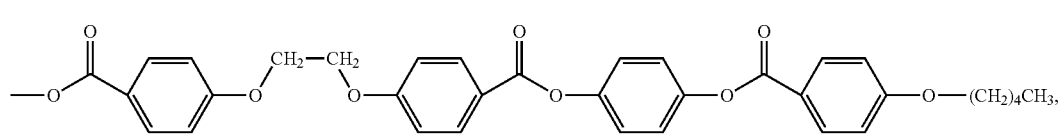
L(x)

-continued

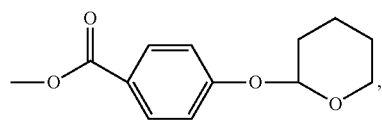 L(y)

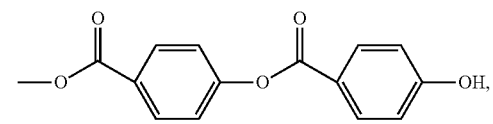 L(z)

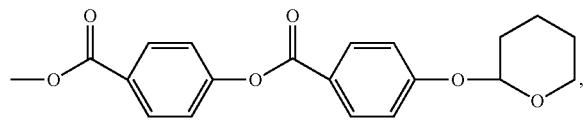 L(aa)

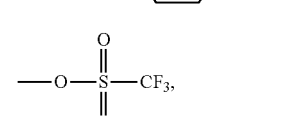 L(ab)

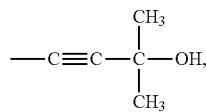 L(ac)

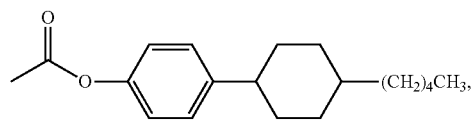 L(ad)

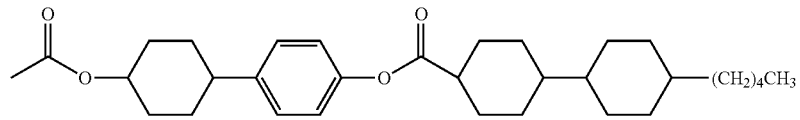 L(ae)

L(af)

L-DC-(a) (4-trans-(4-pentylcyclohexyl)benzamido)phenyl,
L-DC-(b) (4-(4-trans-(4-pentylcyclohexyl)phenoxy)carbonyl)phenyl,
L-DC-(c) 4-(4-(4-trans-(4-pentylcyclohexyl)phenyl)benzamido)phenyl,
L-DC-(d) 4-((trans-(4'-pentyl-[1,1'-bi(cyclohexan)]-4-yl)oxy)carbonyl)phenyl,
L-DC-(e) 4-(4'-(4-pentylcyclohexyl)-[1,1'-biphenyl]-4-ylcarboxamido)phenyl,
L-DC-(f) 4-((4'-(4-pentylcyclohexyl)-[1,1'-biphenyl]-4-carbonyl)oxy)benzamido,
L-DC-(g) 4-(4'-(4-pentylcyclohexyl)-[1,1'-biphenyl]-4-carbonyl)piperazin-1-yl,
L-DC-(h) 4-(4-(4-trans-(4-pentylcyclohexyl)phenyl)benzamido)-2-(trifluoromethyl)phenyl,
L-DC-(i) 2-methyl-4-trans-(4-((4'-trans-(4-pentylcyclohexyl)biphenyl-4-yloxy)carbonyl)cyclohexanecarboxamido)phenyl,
L-DC-(j) 4'-(4'-pentylbi(cyclohexane-4-)carbonyloxy)biphenylcarbonyloxy,
L-DC-(k) 4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl, and
L-DC-(l) 4-((S)-2-methylbutoxy)phenyl)-10-(4-(((3R,3aS,6S,6aS)-6-(4'-trans-(4-pentylcyclohexyl)biphenylcarbonyloxy)hexahydrofuro[3,2-b]furan-3-yloxy)carbonyl)phenyl, provided that $R_{13}$ of N—$R_{13}$ is only selected from L(5), L(6), L(7), L(8), L(9), L(12), L(14), L(21), L(24), L(27), L(34), L(36), L(h), L(i), L(j), L(l), L(m), L(n), L(n), L(o), L(p), L(u), L(v), L(w), L(ac), L(ae), L(af), L-DC-(a), L-DC-(b), L-DC-(c), L-DC-(d), L-DC-(e), L-DC-(h), L-DC-(i), and L-DC-(l).

10. The photochromic compound of claim 8 wherein said photochromic compound represented by Formula (I-B) is selected from at least one of:

(I-B)-(1) 3-(4-methoxyphenyl)-12,14,14-trimethyl-9,11-dioxo-3-phenyl-3,9,11,14-tetrahydrofuro[3',4':4,5]indeno[2',3':3,4]naphtho[1,2-b]pyran

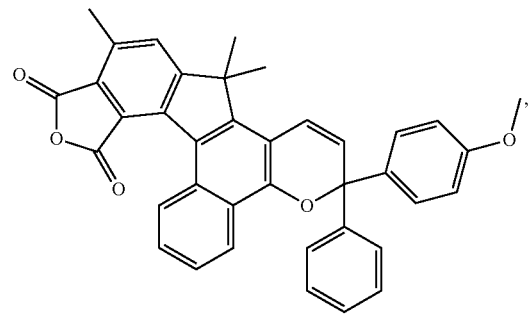 [SMILES: COc1ccc(C2(c3ccccc3)C=Cc3c4c(c5ccccc5c3O2)-c2c(cc(C)c3c2C(=O)OC3=O)C4(C)C)cc1]

(I-B)-(2) 3-(4-butoxyphenyl)-6-fluoro-3-(4-fluorophenyl)-14,14-dimethyl-9,11-dioxo-3,9,11,14-tetrahydrofuro[3',4':4,5]indeno[2',3':3,4]naphtho[1,2-b]pyran

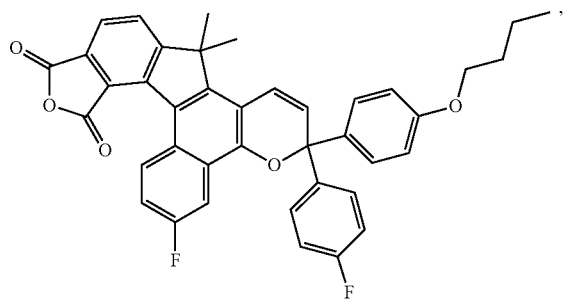 [SMILES: CCCCOc1ccc(C2(c3ccc(F)cc3)C=Cc3c4c(c5ccc(F)cc5c3O2)-c2c(ccc3c2C(=O)OC3=O)C4(C)C)cc1]

(I-B)-(3) 3-(4-methoxyphenyl)-14,14-dimethyl-9,11-dioxo-3-phenyl-12-(2-(2-phenylpropan-2-yl))-3,9,11,14-tetrahydrofuro[3',4':4,5]indeno[2',3':3,4]naphtho[1,2-b]pyran

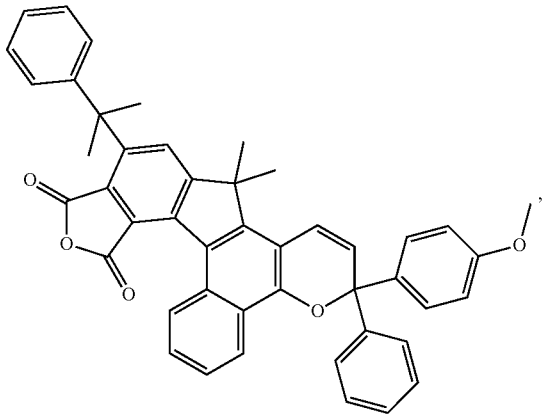 [SMILES: COc1ccc(C2(c3ccccc3)C=Cc3c4c(c5ccccc5c3O2)-c2c(cc(C(C)(C)c3ccccc3)c3c2C(=O)OC3=O)C4(C)C)cc1]

(I-B)-(4) 3-(4-methoxyphenyl)-14,14-dimethyl-11-oxo-3-phenyl-12-(2-(2-phenylpropan-2-yl))-3,9,11,14-tetrahydrofuro[3',4':4,5]indeno[2',3':3,4]naphtho[1,2-b]pyran

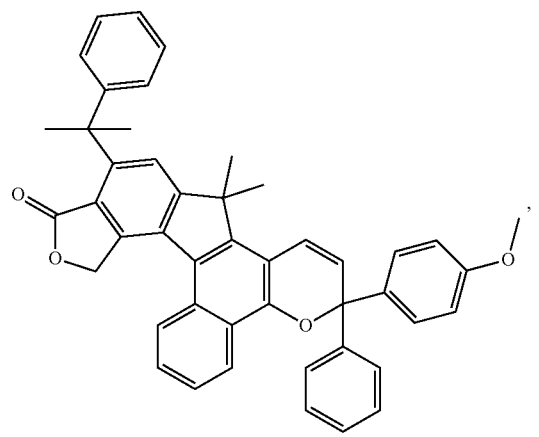 [SMILES: COc1ccc(C2(c3ccccc3)C=Cc3c4c(c5ccccc5c3O2)-c2c(cc(C(C)(C)c3ccccc3)c3c2COC3=O)C4(C)C)cc1]

(I-B)-(5) 10-(4-bromophenyl)-3-(4-methoxyphenyl)-12,14,14-trimethyl-9,11-dioxo-3-phenyl-3,9,11,14-tetrahydropyrrolo[3',4':4,5]indeno[2',3':3,4]naphtho[1,2-b]pyran

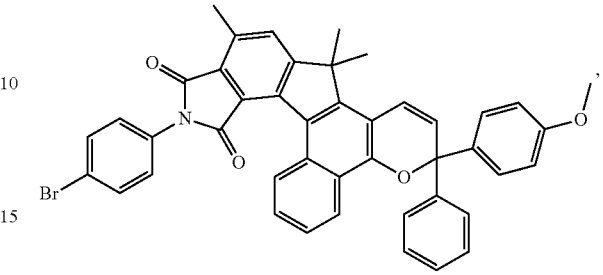

(I-B)-(6) 10-(4-bromophenyl)-3-(4-butoxyphenyl)-3-(4-methoxyphenyl)-12,14,14-trimethyl-9,11-dioxo-3-phenyl-3,9,11,14-tetrahydropyrrolo[3',4':4,5]indeno[2',3':3,4]naphtho[1,2-b]pyran

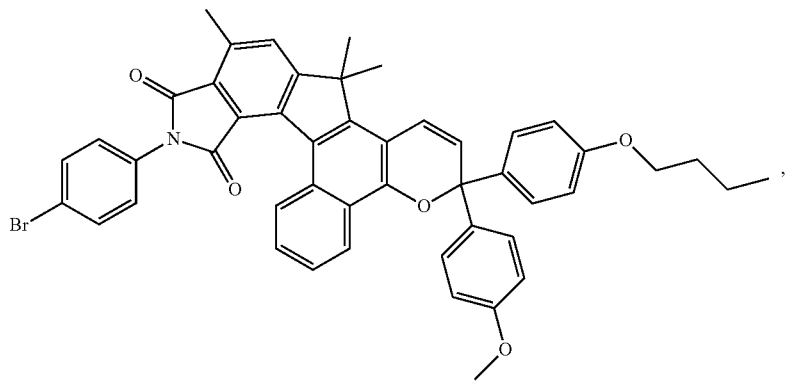 [SMILES: CCCCOc1ccc(C2(c3ccc(OC)cc3)C=Cc3c4c(c5ccccc5c3O2)-c2c(cc(C)c3c2C(=O)N(c2ccc(Br)cc2)C3=O)C4(C)C)cc1]

(I-B)-(7): 10-(4-bromophenyl)-3-(4-methoxyphenyl)-14,14-dimethyl-9,11-dioxo-3-phenyl-12-(2-(2-phenylpropan-2-yl))-3,9,11,14-tetrahydropyrrolo[3',4':4,5]indeno[2',3':3,4]naphtho[1,2-b]pyran

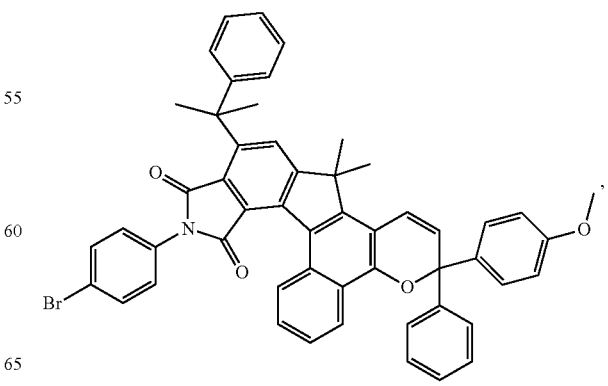

(I-B)-(8) 10-(4-bromophenyl)-9-hydroxy-3-(4-methoxyphenyl)-12,14,14-trimethyl-11-oxo-3-phenyl-3,9,11,14-tetrahydropyrrolo[3',4':4,5]indeno[2',3':3,4]naphtho[1,2-b]pyran

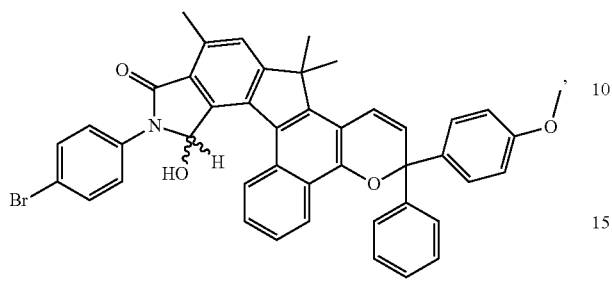

(I-B)-(9) 10-(4-bromophenyl)-3-(4-methoxyphenyl)-12,14,14-trimethyl-11-oxo-3-phenyl-3,9,11,14-tetrahydropyrrolo[3',4':4,5]indeno[2',3':3,4]naphtho[1,2-b]pyran

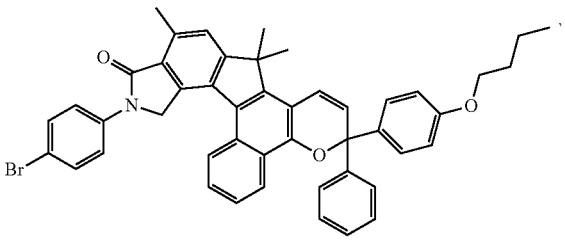 [SMILES: CCCCOc1ccc(C2(c3ccccc3)C=Cc3c4c(c5ccccc5c3O2)-c2c(cc(C)c3c2CN(c2ccc(Br)cc2)C3=O)C4(C)C)cc1]

(I-B)-(10) 3-(4-methoxyphenyl)-10-(4'-(4-(trans-4-pentylcyclohexyl)benzamido)-[1,1'-biphenyl])-12,14,14-trimethyl-9,11-dioxo-3-phenyl-3,9,11,14-tetrahydropyrrolo[3',4':4,5]indeno[2',3':3,4]naphtho[1,2-b]pyran

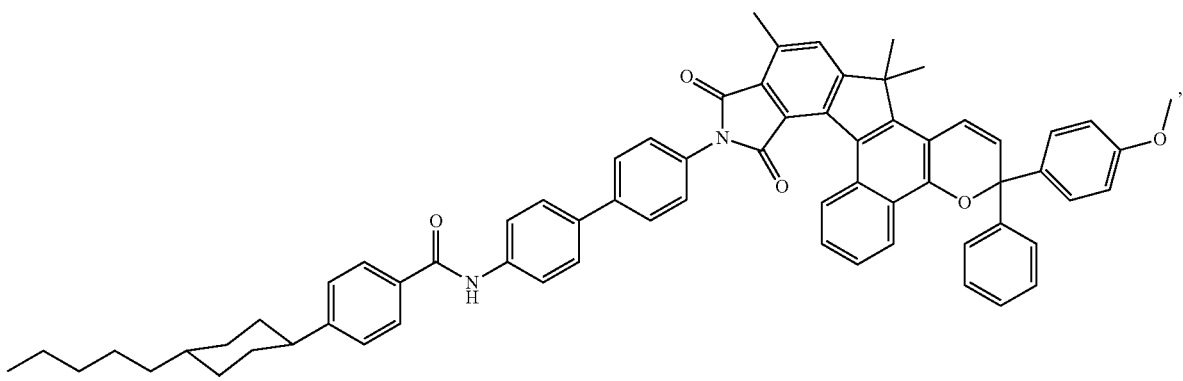 [SMILES: CCCCCC1CCC(c2ccc(C(=O)Nc3ccc(-c4ccc(N5C(=O)c6c(C)cc7c(c6C5=O)-c5c(c6c(c8ccccc58)OC(c5ccccc5)(c5ccc(OC)cc5)C=C6)C7(C)C)cc4)cc3)cc2)CC1]

(I-B)-(11) 3-(4-butoxyphenyl)-9-hydroxy-3-(4-methoxyphenyl)-10-(4'-(4-(trans-4-pentylcyclohexyl)benzamido)-[1,1'-biphenyl])-12,14,14-trimethyl-11-oxo-3,9,11,14-tetrahydropyrrolo[3',4':4,5]indeno[2', 3':3,4]naphtho[1,2-b]pyran

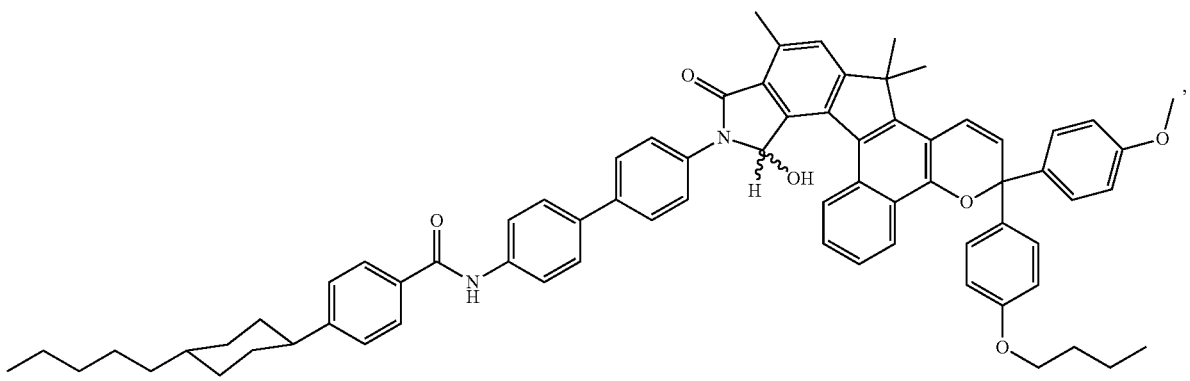

(I-B)-(12)  3-(4-methoxyphenyl)-10-(4'-(4-(trans-4-pentylcyclohexyl)benzamido)-[1,1'-biphenyl])-12-(2-(2-phenylpropan-2-yl))-14,14-dimethyl-9,11-dioxo-3-phenyl-3,9,11,14-tetrahydropyrrolo[3',4':4,5]indeno[2',3':3,4]naphtho[1,2-b]pyran

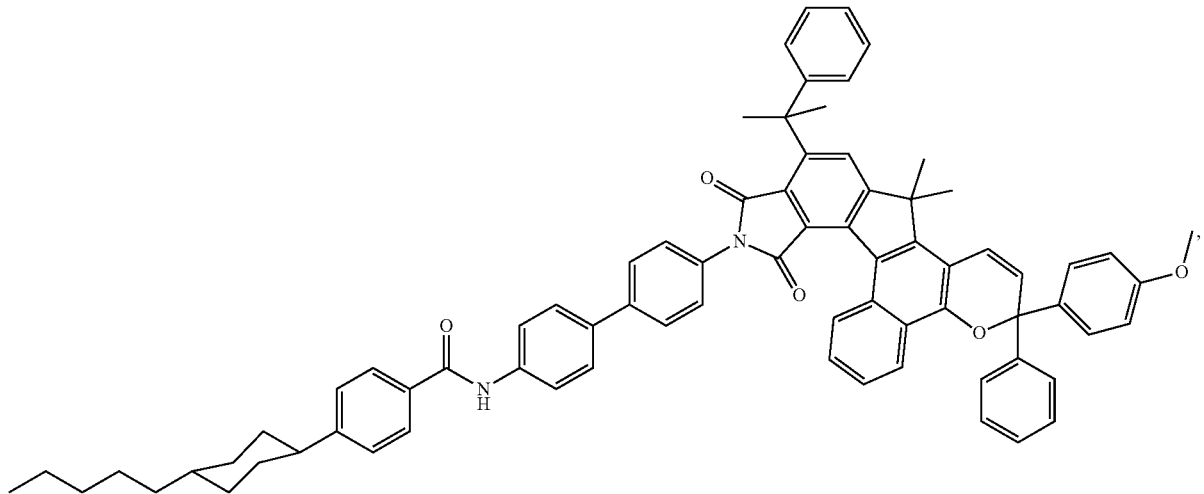 [SMILES: CCCCCC1CCC(c2ccc(C(=O)Nc3ccc(-c4ccc(N5C(=O)c6c(C(C)(C)c7ccccc7)cc7c(c6C5=O)-c5c(c6c(c8ccccc58)OC(c5ccccc5)(c5ccc(OC)cc5)C=C6)C7(C)C)cc4)cc3)cc2)CC1]

(I-B)-(13)  3-(4-butoxyphenyl)-3-(4-fluorophenyl)-6-methoxy-14,14-dimethyl-9,11-dioxo-3,9,11,14-tetrahydrofuro[3',4':4,5]indeno[2',3':3,4]naphtho[1,2-b]pyran (I-B)-(15)  3-(4-butoxyphenyl)-3-(4-fluorophenyl)-15,17,17-trimethyl-9,14-dioxo-3,9,14,17-tetrahydro naphtho[2',3':4,5]indeno[2',3':3,4]naphtho[1,2-b]pyran

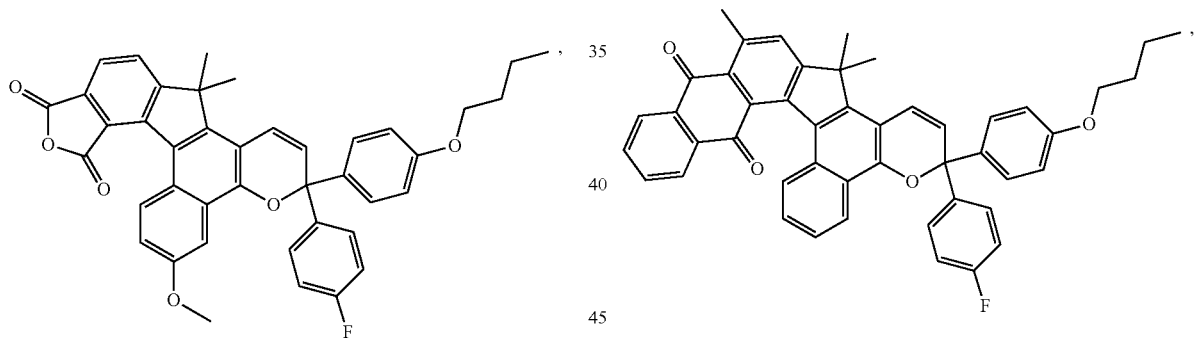

(I-B)-(14):  3-(4-butoxyphenyl)-3-(4-fluorophenyl)-13,15,15-dimethyl-12-oxo-3,9,10,11,12,13,15-hexahydrobenzo[4,5]indeno[2',3':3,4]naphtho[1,2-b]pyran (I-B)-(16)  3-(4-butoxyphenyl)-3-(4-fluorophenyl)-13,15,15-dimethyl-9,12-dioxo-3,9,12,15-tetrahydrobenzo[4,5]indeno[2',3':3,4]naphtho[1,2-b]pyran

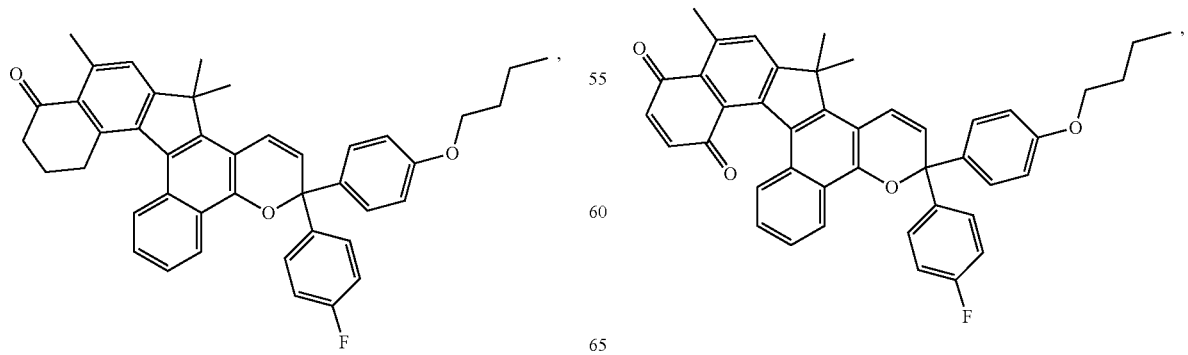

and (I-B)-(17) 3-(4-butoxyphenyl)-3-(4-fluorophenyl)-12-nitro-14-oxo-15,17,17-trimethyl-3,14,17-trihydrochromeno[2',3',4,5]indeno[2',3':3,4]naphtho[1,2-b]pyran

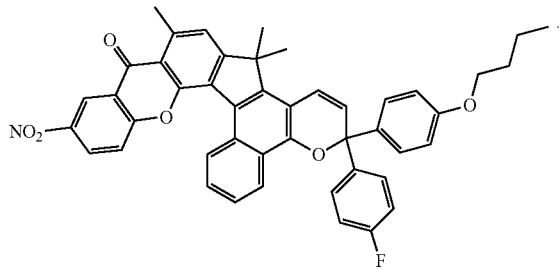 [SMILES: CCCCOc1ccc(C2(c3ccc(F)cc3)C=Cc3c4c(c5ccccc5c3O2)-c2c(cc(C)c3c(=O)c5cc([N+](=O)[O-])ccc5oc23)C4(C)C)cc1]

11. The photochromic compound of claim 4 wherein said photochromic compound is a photochromic-dichroic compound.

12. A photochromic article comprising the photochromic compound of claim 1.

13. The photochromic article of claim 12 wherein said photochromic article is selected from ophthalmic articles, display articles, windows, mirrors, and active liquid crystal cell articles, and passive liquid crystal cell articles.

14. The photochromic article of claim 13, wherein said photochromic article is selected from ophthalmic articles, and said ophthalmic articles are selected from corrective lenses, non-corrective lenses, contact lenses, intra-ocular lenses, magnifying lenses, protective lenses, and visors.

15. The photochromic article of claim 13, wherein said photochromic article is selected from display articles, and said display articles are selected from screens, monitors, and security elements.

* * * * *